(12) United States Patent
Federico

(10) Patent No.: US 11,559,571 B2
(45) Date of Patent: Jan. 24, 2023

(54) NUCLEOTIDE SEQUENCE EXPRESSING AN EXOSOME-ANCHORING PROTEIN FOR USE AS VACCINE

(71) Applicant: ISTITUTO SUPERIORE DI SANITÀ, Rome (IT)

(72) Inventor: Maurizio Paolo Maria Federico, Rome (IT)

(73) Assignee: ISTITUTO SUPERIORS DI SANITÀ, Rome (IT)

( * ) Notice: Subject to any disclaimer, the term of this patent is extended or adjusted under 35 U.S.C. 154(b) by 72 days.

(21) Appl. No.: 16/341,042

(22) PCT Filed: Oct. 11, 2017

(86) PCT No.: PCT/IT2017/000223
§ 371 (c)(1),
(2) Date: Apr. 10, 2019

(87) PCT Pub. No.: WO2018/069947
PCT Pub. Date: Apr. 19, 2018

(65) Prior Publication Data
US 2020/0206329 A1  Jul. 2, 2020

(30) Foreign Application Priority Data

Oct. 11, 2016  (IT) .................. 102016000101794

(51) Int. Cl.
| A61K 39/12 | (2006.01) |
| C12N 15/62 | (2006.01) |
| C12N 15/63 | (2006.01) |
| A61K 39/00 | (2006.01) |
| A61K 9/00 | (2006.01) |

(52) U.S. Cl.
CPC ........ *A61K 39/0011* (2013.01); *A61K 9/0019* (2013.01); *A61K 39/00119* (2018.08); *A61K 39/001106* (2018.08); *A61K 39/001186* (2018.08); *A61K 39/001191* (2018.08); *C12N 15/62* (2013.01); *A61K 2039/53* (2013.01); *A61K 2039/572* (2013.01)

(58) Field of Classification Search
None
See application file for complete search history.

(56) References Cited

U.S. PATENT DOCUMENTS

| 2004/0234503 A1 | 11/2004 | Cerundolo et al. |
| 2013/0039942 A1 | 2/2013 | Kornbluth et al. |
| 2020/0325182 A1 | 10/2020 | Keller et al. |

FOREIGN PATENT DOCUMENTS

| CN | 112409496 A | 2/2021 |
| JP | 2011-517402 A | 6/2011 |
| WO | WO 2011/159814 A2 | 12/2011 |
| WO | WO 2015/161853 A1 | 4/2015 |
| WO | WO 2018/069947 A1 | 4/2018 |
| WO | WO 2018/122885 A1 | 7/2018 |

OTHER PUBLICATIONS

Maldonado et al. Intramuscular Therapeutic Vaccination Targeting HPV16 Induces T Cell Responses That Localize in Mucosal Lesions. Science Translational Medicine Jan. 29, 2014; vol. 6, Issue 221, pp. 221ra13.*
Di Bonito et al. HPV-E7 Delivered by Engineered Exosomes Elicits a Protective CD8+ T Cell-Mediated Immune Response. Viruses 2015, 7, 1079-1099.*
Bolhassani et al. Different spectra of therapeutic vaccine development against HPV infections, Human Vaccines, 2009, 5:10, 671-689.*
Madison et al. Exosomes: Implications in HIV-1 Pathogenesis. Viruses 2015, 7, 4093-4118.*
Arenaccio, C. et al., "Cell activation and HIV-1 replication in unstimulated CD4 T lymphocytes ingesting exosomes from cells expressing defective HIV-1," Retrovirology, 2014, vol. 11, 16 pages.
Arico, E. et al., "Chemo-immunotherapy induces tumor regression in a mouse model of spontaneous mammary carcinogenesis," Oncotarget, 2016, vol. 7, No. 37, pp. 59754-59765.
Bauer, S. et al., "Identification of H-2Kb binding and immunogenic peptides from human papilloma virus tumour antigens E6 and E7," Scand J Immunol, 1995, vol. 42, pp. 317-323.
Busam, K.J. et al., "Melan-A, a new melanocytic differentiation marker," Adv Anat Pathol, 1996, vol. 6, pp. 12-18.
Chairoungdua, A. et al., "Exosome release of beta-catenin: a novel mechanism that antagonizes Wnt signaling," J Cell Biol, 2010, vol. 190, pp. 1079-1091.
Chaput, N. et al., "Exosomes: immune properties and potential clinical implementations," Semin Immunopathol, 2011, vol. 33, pp. 419-440.
D'Aloja, P. et al., "gag, vif, and nef genes contribute to the homologous viral interference induced by a nonproducer human immunodeficiency virus type 1 (HIV-1) variant: identification of novel HIV 1-inhibiting viral protein mutants," J. Virol, 1998, vol. 72, No. 4308-4319.
Dai, S. et al., "Phase I clinical trial of autologous ascites-derived exosomes combined with GM-CSF for colorectal cancer," Mol Ther, 2008, vol. 16, pp. 782-790.
Di Bonito, P. et al., "Anti-tumor CD8+ T cell immunity elicited by HIV-1 based virus-like particles incorporating HPV-16 E7 protein," Virology, 2009, vol. 395, pp. 45-55.
Di Bonito, P. et al., "Antitumor HPV E7-specific CTL activity elicited by in vivo engineered exosomes produced through DNA inoculation," Int J Nanomedicine, 2017, vol. 12, pp. 4579-4591.
El Garch, H. et al., "A West Nile virus (WNV) recombinant canarypox virus vaccine elicits WNV-specific neutralizing antibodies and cell-mediated immune responses in the horse," Vet Immunol, 2008, vol. 123, pp. 230-239.

(Continued)

*Primary Examiner* — Nianxiang Zou
(74) *Attorney, Agent, or Firm* — Fenwick & West LLP

(57) ABSTRACT

The present invention concerns a nucleotide sequence expressing a fusion protein, said fusion protein comprising or consisting of an exosome-anchoring protein fused at its C-terminus with an antigen, or a DNA expression vector comprising said nucleotide sequence, for use as vaccine.

14 Claims, 23 Drawing Sheets

Figure 1:
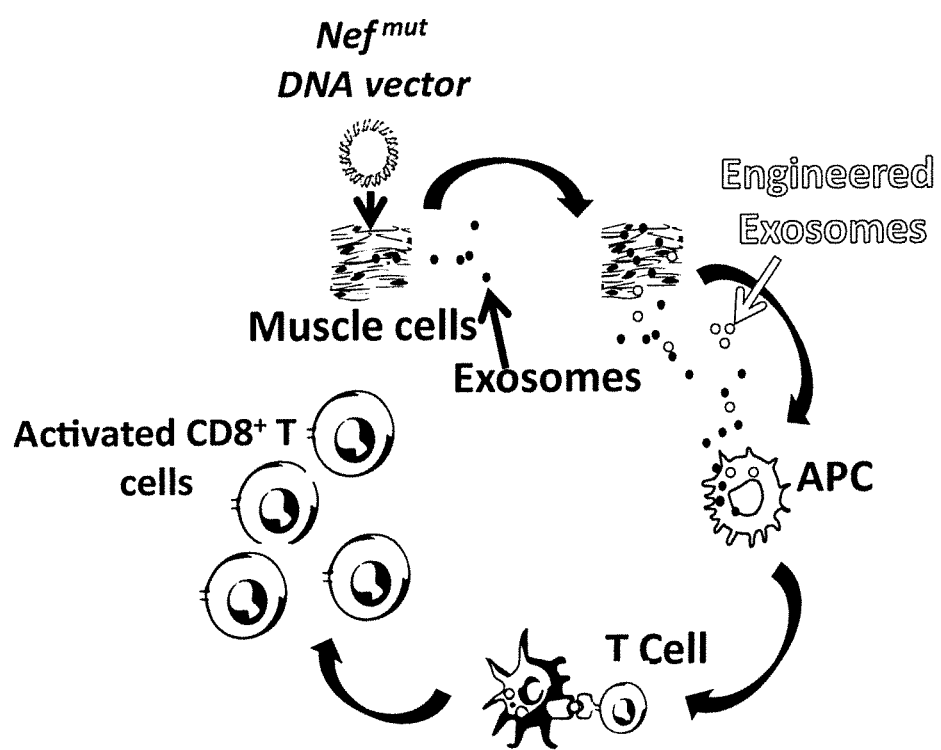

Specification includes a Sequence Listing.

(56) References Cited

OTHER PUBLICATIONS

Escudier, B. et al., "Vaccination of metastatic melanoma patients with autologous dendritic cells (DC) derived-exosomes: results of the first phase I clinical trial," J. Transl Med, 2005, vol. 3, No. 10, 13 pages.
Fry, E.A. et al., "Clinical applications of mouse models for breast cancer engaging HER2/neu," Integr Cancer Sci Ther, 2016, vol. 3, No. 5, pp. 593-603.
Gritzapis, A.D. et al., "Vaccination with human HER-W/neu (435-443) CTL peptide induces effective antitumor immunity against HER-W/neu-expressing tumor cells in vivo," Cancer Res, 2006, vol. 66, No. 10, pp. 5452-5460.
Guescini, M. et al., "C2C12 myoblasts release micro-vesicles containing mtDNA and proteins involved in signal transduction," Exp Cell Res, 2010, vol. 16, pp. 1977-1984.
Halbert, C.L. et al., "The E7 gene of human papillomavirus type 16 is sufficient for immortalization of human epithelial cells," J. Virol, 1991, vol. 65, pp. 473-478.
Halstead, S.B. et al., "New Japanese encephalitis vaccines: alternatives to production in mouse brain," Expert Rev Vaccines, 2011, vol. 10, pp. 355-364.
Keppler, O.T. et al., "Rodent cells support key functions of the human immunodeficiency virus type 1 pathogenicity factor Nef," J. Virol, 2005, vol. 79, pp. 1655-1665.
Kogure, T. et al., "Intercellular nanovesicle-mediated microRNA transfer: a mechanism of environmental modulation of hepatocellular cancer cell growth," Hepatology, 2011, vol. 54, pp. 1237-1248.
Kosaka, N. et al., "Competitive interactions of cancer cells and normal cells via secretory microRNAs," J. Biol Chem, 2012, vol. 287, pp. 1397-1405.
Kosaka, N. et al., "Secretory mechanisms and intercellular transfer of microRNAs in living cells," J. Biol Chem, 2010, vol. 285, pp. 17442-17452.
Krohn, K. et al., "A DNA HIV-1 vaccine based on a fusion gene expressing non-structural and structural genes of consensus sequence of the A-C subtypes and the ancestor sequence of the F-H subtypes. Preclinical and clinical studies," Microbes and Infection, Nov. 2005, vol. 7, No. 14, pp. 1405-1413.
Liang, X. et al., "Development of HIV-1 Nef vaccine components: immunogenicity study of NEF mutants lacking myristoylation and dileucine motif in mice," Vaccine, 2002, vol. 20, pp. 413-421.
Massa, S. et al., "Antitumor activity of DNA vaccines based on the human papillomavirus-16 E7 protein genetically fused to a plan virus coat protein," Hum. Gene Ther, 2008, vol. 19, pp. 354-364.
Morse, M.A. et al., "A phase I study of dexosome immunotherapy in patients with advanced non-small cell lung cancer," J. Transl Med, 2005, vol. 3, No. 9, 8 pages.
Nanni, P. et al., "Combined allogeneic tumor cell vaccination and systemic interleukin 12 prevents mammary carcinogenesis in HER-2/neu transgenic mice," J Exp Med, 2001, vol. 194, pp. 1195-1205.
Nanni, P. et al., "Immunoprevention of mammary carcinoma in HER-2/neu transgenic mice is IFN-gamma and B cell dependent," J. Immunol, 2004, vol. 173, No. 4, pp. 2288-2296.
Ng, T. et al., "Equine vaccine for West Nile virus," Dev Biol, 2013, vol. 114, pp. 221-227.
Peretti, S. et al., "Cell death induced by the herpes simplex virus-1 thymidine kinase delivered by human immunodeficiency virus-1-based virus-like particles," Mol Ther, 2005, vol. 12, No. 6, pp. 1185-1196.
Quaglino, E. et al., "Electroporated DNA vaccine clears away multifocal mammary carcinomas in her-2/neu transgenic mice," Cancer Res, 2004, vol. 64, No. 8, pp. 2858-2864.
Quaglino, E. et al., "The adjuvant activity of BAT antibody enables DNA vaccination to inhibit the progression of established autochthonous Her-2/neu carcinomas in BALB/c mice," Vaccine, 2005, vol. 23, No. 25, pp. 3280-3287.

Rieu, S. et al., "Exosomes released during reticulocyte maturation bind to fibronectin via integrin alpha4beta1," Eur J Biochem, 2000, vol. 267, pp. 583-590.
Rivoltini, L. et al., "Induction of tumor-reactive CTL from peripheral blood and tumor-infiltrating lymphocytes of melanoma patients by in vitro stimulation with an immunodominant peptide of the human melanoma antigen MART-1," J. Immunol, 1995, vol. 154, pp. 2257-2265.
Rolla, S. et al., "Distinct and non-overlapping T cell receptor repertoires expanded by DNA vaccination in wild-type and HER-2 transgenic BALB/c mice," J. Immunol, 2006, vol. 177, No. 11, pp. 7626-7633.
Rolla, S. et al., "Protective immunity against neu-positive carcinomas elicited by electroporation of plasmids encoding decreasing fragments of rat neu extracellular domain," Hum Gene Ther, 2008, vol. 19, No. 3, pp. 229-239.
Romancino, D.P.et al., "Identification and characterization of the nano-sized vesicles released by muscle cells," FEB Lett, 2013, vol. 587, pp. 1379-1384.
Rovero, S. et al., "DNA vaccination against rat her-2/Neu p185 more effectively inhibits carcinogenesis than transplantable carcinomas in transgenic BALB/ca mice," J. Immunol, 2000, vol. 165, No. 9, pp. 5133-5142.
Schreiber, R.D. et al., "Cancer immunoediting: integrating immunity's roles in cancer suppression and promotion," Science, 2011, vol. 331, No. 6024, pp. 1565-1570.
Stuve, O. et al.., "DNA plasmid vaccination for multiple sclerosis," Arch Neurol, 2007, vol. 64, pp. 1385-1386.
Tan, A. et al., "The application of exosomes as a nanoscale cancer vaccine," Int J Nanomedicine, 2010, vol. 5, pp. 889-900.
Thery, C. et al., "Isolation and characterization of exosomes from cell culture supernatants and biological fluids," Curr Prot Cell Biol, 2006, pp. 3.22.1-3.22.29.
Trajkovic, K. et al., "Ceramide triggers budding of exosome vesicles into multivesicular endosomes," Science, 2008, vol. 319, pp. 1244-1247.
Van Der Burg, S.H. et al., "Vaccines for established cancer: overcoming the challenges posed by immune evasion," Nat Rev Cancer, 2016, vol. 16, No. 4, pp. 219-233.
Yuyama, K. et al., "Sphingolipid-modulated exosome secretion promotes clearance of amyloid-beta by microglia," J. Biol Chem, 2012, vol. 287, pp. 10977-10989.
PCT International Search Report & Written Opinion, International Application No. PCT/IT2017/000223, dated Feb. 20, 2018, 10 Pages.
Di Bonito, P., et al., "HPV-E7 Delivered by Engineered Exosomes Elicits a Protective CD8+ T Cell-Mediated Immune Response," Viruses, 2015, pp. 1079-1099, vol. 7.
Lattanzi, L., et al., "A strategy of antigen incorporation into exosomes: Comparing cross-presentation levels of antigens delivered by engineered exosomes and by lentiviral virus-like particles," Vaccine, 2012, pp. 7229-7237, vol. 30, No. 50.
Anticoli, S. et al., "An Exosome-Based Vaccine Platform Imparts Cytotoxic T Lymphocyte Immunity Against Viral Antigens," Biotechnology Journal, 2018, vol. 13, pp. 1700443.
Anticoli, S. et al., "Engineered exosomes emerging from muscle cells break immune tolerance to HER2 in transgenic mice and induce antigen-specific CTLs upon challenge by human dendritic cells," Journal of Molecular Medicine, 2018, vol. 96, pp. 211-221.
Arenaccio, C. et al., "The Multifaceted Functions of Exosomes in Health and Disease: An Overview," Exosomes in Cardiovascular Diseases, Adv Exp Med Biol, 2017, pp. 1-19.
Commandeur, S., et al., An Unbiased Genome-Wide *Mycobacterium tuberculosis* Gene Expression Approach to Discover Antigens Targeted by Human T Cells Expressed During Pulmonary Infection, Journal of Immunology, 2013, vol. 190, pp. 1659-1671.
Di Bonito, P. et al., "HPV-E7 Delivered by Engineered Exosomes Elicits a Protective CD8 T Cell-Mediated Immune Response," Viruses, 2015, vol. 7, pp. 1079-1099.
Di Bonito, P. et al., "Anti-Cancer Vaccine for HPV-Associated Neoplasms: Focus on a Therapeutic HPV Vaccine based on a Novel Tumor Antigen Delivery Method Using Endogenously Engineered Exosomes," Cancers, 2019, vol. 11, No. 128, pp. 1-15.

(56) References Cited

OTHER PUBLICATIONS

Ewer, K.J. et al., "Protective CD8 T-cell immunity to human malaria induced by chimpanzee adenovirus-MVA immunisation," Nature Communications, 2013, pp. 1-10.
Ferrantelli, F. et al., "DNA Vectors Generating Engineered Exosomes Potential CTL Vaccine Candidates Against AIDS, Hepatitis B, and Tumors," Molecular Biotechnology, 2018, vol. 60, pp. 773-782.
Kaufmann, S.H.E. et al., "Novel approaches to tuberculosis vaccine development," International Journal of Infectious Diseases, 2017, vol. 56, pp. 263-267.
Lewinsohn, D.A. et al., "Comprehensive definition of human immunodominant CD8 antigens in tuberculosis," npj Vaccines, 2017, vol. 2, No. 8, pp. 1-11.
Manfredi, F. et al., "Incorporation of Heterologous Proteins in Engineered Exosomes," Lentiviral Vectors and Exosomes as Gene and Protein Delivery Tools, Methods in Molecular Biology, 2016, vol. 1448, pp. 249-260.
Sedegah, M. et al., "Identification of minimal human MHC-restricted CD8 T-cell epitopes within the Plasmodium falciparum circumsporozoite protein (CSP)," Malaria Journal, 2013, vol. 12, No. 185, pp. 1-17.
Voss, G. et al., "Progress and challenges in TB vaccine development," F1000 Research, 2018, vol. 7, pp. 1-12.
Russian Patent Office, Office Action, RU Patent Application No. 2019114370, dated Mar. 1, 2021, 11 pages.
Tchevkina, E.M. et al., "Exosomes and transfer of (epi)genetic information by tumor cells," Advances in Molecular Oncology, vol. 2, No. 3, 2015, pp. 8-20 (with English abstract).
Japan Patent Office, Office Action, JP Patent Application No. 2019-540142, dated Sep. 3, 2021, eight pages.
Yang, B. et al., "DNA vaccine for cancer immunotherapy," Human Vaccines & Immunotherapeutics, vol. 10, Iss. 11, Jan. 27, 2015, pp. 3153-3164.
Zeelenberg, I.S. et al., "Targeting Tumor Antigens to Secreted Membrane Vesicles In vivo Induces Efficient Antitumor Immune Responses," Cancer Research, vol. 68, No. 4, Feb. 15, 2008, pp. 1228-1235.
Allard, S.D. et al., "Corrigendum to 'A phase I/IIa immunotherapy trial of HIV-1-infected patients with Tat, Rev and Nef expressing dendritic cells followed by treatment interruption' [Clin. Immunol. 142 (2012) 252-268]," Clinical Immunology, vol. 150, Iss. 1, Jan. 2014, pp. 88-89.
Best, S.R. et al., "Administration of HPV DNA vaccine via electroporation elicits the strongest CD8+ T cell immune responses compared to intramuscular injection and intradermal gene gun delivery," Vaccine, vol. 27, No. 40, Sep. 4, 2009, pp. 5450-5459.
Boczkowski, D. et al., "Dendritic Cells Pulsed with RNA are Potent Antigen-presenting Cells In Vitro and In Vivo," J. Exp. Med., vol. 184, Aug. 1996, pp. 465-472.
Cherney, K., "HIV Vaccine Trials and Progress for 2021," Healthline, Dec. 17, 2021, pp. 1-11, [Online] [Retrieved on Dec. 23, 2021] Retrieved from the Internet <URL: https://www.healthline.com/health/hiv/hiv-vaccine-2021>.
Gandhi, R.T. et al., "Immunization of HIV-1-Infected Persons With Autologous Dendritic Cells Transfected With mRNA Encoding HIV-1 Gag and Nef: Results of a Randomized, Placebo-Controlled Clinical Trial," J Acquir Immune Defic Syndr, vol. 71, No. 3, Mar. 1, 2016, pp. 246-253.
Heaton, P. M., "Challenges of Developing Novel Vaccines With Particular Global Health Importance," Frontiers in Immunology, vol. 11, Oct. 2020, pp. 1-13.
Leal, L. et al., "Phase I clinical trial of an intranodally administered mRNA-based therapeutic vaccine against HIV-1 infection," AIDS 2018, vol. 32, No. 17, Nov. 2018, pp. 2533-2545.
Nolen, S., "Most of the World's Vaccines Likely Won't Prevent Infection From Omicron," New York Times, Dec. 19, 2021, pp. 1-20, [Online] [Retrieved on Dec. 23, 2021] Retrieved from the Internet <URL: https://www.nytimes.com/2021/12/19/health/omicron-vaccines-efficacy.html>.

PCT International Search Report and Written Opinion, PCT Application No. PCT/EP2021/062075, dated Aug. 10, 2021, pp. 1-17.
PCT International Search Report and Written Opinion, PCT Application No. PCT/EP2021/061730, dated Jul. 29, 2021, pp. 1-17.
Rosa, S.S. et al., "mRNA vaccines manufacturing: Challenges and bottlenecks," Vaccine, vol. 39, Mar. 24, 2021, pp. 2190-2200.
Borysiewicz, L. K. et al. "A recombinant vaccinia virus encoding human papillomavirus types 16 and 18, E6 and E7 proteins as immunotherapy for cervical cancer." The Lancet, vol. 347, Jun. 1, 1996, pp. 1523-1527.
Braun, J. et al. "Presence of SARS-CoV-2-Reactive T Cells in COVID-19 Patients and Healthy Doctors." medRxiv Preprint, Apr. 22, 2020, pp. 1-12.
Cai, C. Y. et al. "Two Sorting Motifs, a Ubiquitination Motif and a Tyrosine Motif, Are Involved in HIV-1 and Simian Immunodeficiency Virus Nef-Mediated Receptor Endocytosis." The Journal of Immunology, vol. 186, No. 10, May 15, 2011, pp. 5807-5814.
Cargnelutti, D. E. et al. "Development of a Universal CTL-Based Vaccine for Influenza." Bioengineered, vol. 4, No. 6, Nov./Dec. 2013, pp. 374-378.
Chan, J. F-W. et al. "A Familial Cluster of Pneumonia Associated with the 2019 Novel Coronavirus Indicating Person-to-Person Transmission: A Study of a Family Cluster." The Lancet, vol. 395, No. 10223, Feb. 2020, pp. 514-523.
Chang, S-C. et al. "Longitudinal Analysis of Severe Acute Respiratory Syndrome (SARS) Coronavirus-Specific Antibody in SARS Patients." Clinical and Vaccine Immunology, vol. 12, No. 12, Dec. 1, 2005, pp. 1455-1457.
Channappanavar, R. et al. "Virus-Specific Memory CD8 T Cells Provide Substantial Protection from Lethal Severe Acute Respiratory Syndrome Coronavirus Infection." Journal of Virology, vol. 88, No. 19, Oct. 1, 2014, pp. 11034-11044.
Chen, C-H. et al. "Enhancement of DNA Vaccine Potency by Linkage of Antigen Gene to an HSP70 Gene." Cancer Research, vol. 60, No. 4, Feb. 15, 2000, pp. 1035-1042.
Chiozzini, C. et al. "N-Terminal Fatty Acids of NEF$^{MUT}$ are Required for the CD8+ T-Cell Immunogenicity of In Vivo Engineered Extracellular Vesicles." Vaccines, vol. 8, No. 2, May 22, 2020, pp. 1-10.
D'Aloja, P. et al. "Genetic and Functional Analysis of the Human Immunodeficiency Virus (HIV) Type 1-Inhibiting F12-HIV nef Allele." Journal of General Virology, vol. 82, No. 11, Nov. 1, 2001, pp. 2735-2745.
Dandekar, A. A. et al. "Immunopathogenesis of Coronavirus Infections: Implications for SARS." Nature Reviews Immunology, vol. 5, Dec. 2005, pp. 917-927.
De Oliveira, L. M. F. et al. "Design, Immune Response and Anti-Tumor Potential of an HPV16 E6E7 Multi-Epitope Vaccine." Plos One, vol. 10, No. 9, Sep. 21, 2015, pp. 1-13.
Fan, Y-Y. et al. "Characterization of SARS-CoV-Specific Memory T Cells from Recovered Individuals 4 Years after Infection." Archives of Virology, vol. 154, Jun. 13, 2009, pp. 1093-1099.
Ferrantelli, et al. "Long-Term Antitumor CD8+ T Cell Immunity Induced by Endogenously Engineered Extracellular Vesicles." Cancers, vol. 13, No. 9, May 8, 2021, pp. 1-18.
Ferrantelli, F. et al. "Simultaneous CD8+ T-Cell Immune Response Against SARS-Cov-2 S, M, and N Induced by Endogenously Engineered Extracellular Vesicles in Both Spleen and Lungs." Vaccines, vol. 9, Mar. 10, 2021, pp. 1-20.
Foster, J. L. et al. "Mechanisms of HIV-1 Nef Function and Intracellular Signaling." Journal of Neuroimmune Pharmacology, vol. 6, No. 2, Jun. 2011, pp. 230-246.
Gasper, D. J. et al. "Effective Respiratory CD8 T-Cell Immunity to Influenza Virus Induced by Intranasal Carbomer-Lecithin-Adjuvanted Non-replicating Vaccines." PLOS Pathogens, vol. 12, No. 12, Dec. 20, 2016, pp. 1-36.
Gattinger, P. et al. "Antibodies in Serum of Convalescent Patients Following Mild COVID-19 Do Not Always Prevent Virus-Receptor Binding." Allergy: European Journal of Allergy and Clinical Immunology, vol. 76, No. 3, Mar. 2021, pp. 878-883.
Green, L. A. et al. "Inhibition of HIV-1 Infection and Replication by Enhancing Viral Incorporation of Innate Anti-HIV-1 Protein A3G." Journal of Biological Chemistry, vol. 284, No. 20, May 15, 2009, pp. 13363-13372.

(56) References Cited

OTHER PUBLICATIONS

Grifoni, A. et al. "Targets of T Cell Responses to SARS-CoV-2 Coronavirus in Humans with COVID-19 Disease and Unexposed Individuals." Cell, vol. 181, No. 7, Jun. 25, 2020, pp. 1489-1501.
Guan, W. D. et al. "Characteristics of Traveler with Middle East Respiratory Syndrome, China, 2015." Emerging Infectious Diseases, vol. 21, No. 12, Dec. 2015, pp. 2278-2280.
Gupta, M. et al. "CD8-Mediated Protection Against Ebola Virus Infection is Perforin Dependent." The Journal of Immunology, vol. 174, No. 7, Apr. 1, 2005, pp. 4198-4202.
Hartenian, E. et al. "The Molecular Virology of Coronaviruses." Journal of Biological Chemistry, vol. 295, No. 37, Sep. 2020, pp. 12910-12934.
Hensley, L. E. et al. "Demonstration of Cross-Protective Vaccine Immunity Against an Emerging Pathogenic Ebolavirus Species." PLOS Pathogens, vol. 6, No. 5, May 2010, pp. 1-9.
Huang, J. et al. "Priming with SARS CoV S DNA and Boosting with SARS CoV S Epitopes Specific for $CD4^+$ and $CD8^+$ T Cells Promote Cellular Immune Responses." Vaccine, vol. 25, No. 39-40, Sep. 28, 2007, pp. 6981-6991.
Jang, Y. H. et al. "The Quest for a Truly Universal Influenza Vaccine." Frontiers in Cellular and Infection Microbiology, vol. 9, Article 344, Oct. 2019, pp. 1-24.
Johns Hopkins University. "Covid-19 Dashboard." Center for Systems Science and Engineering at Johns Hoping University, Jun. 7, 2022, 1 page, [Online] [Retrieved Jun. 7, 2022], Retrieved from the Internet <URL:https://coronavirus.jhu.edu/map.html>.
Kalluri, R. et al. "The Biology, Function, and Biomedical Applications of Exosomes." Science, vol. 367, No. 6478, Feb. 7, 2020, pp. 1-40.
Kawano, M. et al. "Chimeric SV40 Virus-Like Particles Induce Specific Cytotoxicity and Protective Immunity Against Influenza A Virus without the Need of Adjuvants." Virology, vol. 448, Jan. 5, 2014, pp. 159-167.
Lee, S-Y. et al. "Nucleoprotein Vaccine Induces Cross-Protective Cytotoxic T Lymphocytes Against both Lineages of Influenza B Virus." Clinical and Experimental Vaccine Research, vol. 8, No. 1, Jan. 2019, pp. 54-63.
Li, J. et al. "Exosomes Mediate the Cell-to-Cell Transmission of IFN-α-Induced Antiviral Activity." Nature Immunology, vol. 14, No. 8, Aug. 2013, pp. 793-803.
Li, Q. et al. "Early Transmission Dynamics in Wuhan, China, of Novel Coronavirus-Infected Pneumonia." The New England Journal of Medicine, vol. 382, No. 13, Mar. 26, 2020, pp. 1199-1207.
Liu, L. et al. "Anti-Spike IgG Causes Severe Acute Ling Injury by Skewing Macrophage Responses During Acute SARS-CoV Infection." JCI Insight, vol. 4, No. 4, Feb. 21, 2019, pp. 1-19.
Liu, W. et al. "Two-Year Prospective Study of the Humoral Immune Response of Patients with Severe Acute Respiratory Syndrome." The Journal of Infectious Diseases, vol. 193, No. 6, Mar. 15, 2006, pp. 792-795.
Liu, W. J. et al. "T-Cell Immunity of SARS-CoV: Implications for Vaccine Development Against MERS-CoV." Antiviral Research, vol. 137, Jan. 2017, pp. 82-92.
Mo, H. et al. "Longitudinal Profile of Antibodies Against SARS-Coronavirus in SARS Patients and Their Clinical Significance." Respirology, vol. 11, No. 1, Jan. 2006, pp. 49-53.
Muratori, C. et al. "Massive Secretion by T Cells is Caused by HIV Nef in Infected Cells and by Nef Transfer to Bystander Cells." Cell Host & Microbe, vol. 6, No. 3, Sep. 17, 2009, pp. 218-230.
Netland, J. et al. "CD8 and CD4 T Cells in West Nile Virus Immunity and Pathogenesis." Viruses, vol. 5, No. 10, Oct. 22, 2013, pp. 2573-2584.
Ng, O-W. et al. "Memory T Cell Response Targeting the SARS Coronavirus Persist up to 11 Years Post-Infection." Vaccine, vol. 34, No. 17, Apr. 12, 2016, pp. 2008-2014.
Ni, L. et al. "Detection of SARS-CoV-2-Specific Humoral and Cellular Immunity in COVID-19 Convalescent Individuals." Immunity, vol. 52, No. 6, Jun. 16, 2020, pp. 971-977.
Oh, H-L. J. et al. "Engineering T Cells Specific for a Dominant Severe Acute Respiratory Syndrome Coronavirus CD8 T Cell Epitope." Journals of Virology, vol. 85, No. 20, Oct. 2011, pp. 10464-10471.
Olinger, G. G. et al. "Protective Cytotoxic T-Cell Responses Induced by Venezuelan Equine Encephalitis Virus Replicons Expressing Ebola Virus Proteins." Journal of Virology, vol. 79, No. 22, Nov. 15, 2005, pp. 14189-14196.
Peng, H. et al. "Long-Lived Memory T Lymphocyte Responses Against SARS Coronavirus Nucleocapsid Protein in SARS-Recovered Patients." Virology, vol. 351, No. 2, Aug. 1, 2006, pp. 466-475.
Raney, A. et al. "Structural Constraints on Human Immunodeficiency Virus Type 1 Nef Function." Virology, vol. 368, No. 1, Nov. 10, 2007, pp. 7-16.
Rome, S. et al. "Skeletal Muscle-Released Extracellular Vesicles: State of the Art." Frontiers in Physiology, vol. 10, Article 929, Aug. 2019, pp. 1-13.
Sakabe, S. et al. "Analysis of $CD8^+$ T Cell Response During the 2013-2016 Ebola Epidemic in West Africa." PNAS, vol. 115, No. 32, Jul. 23, 2018, pp. E7578-E7586.
Schotsaert, M. et al. "Controlling Influenza by Cytotoxic T-Cells: Calling for Help from Destroyers." BioMed Research International, vol. 2010, Article ID 863985, May 24, 2010, pp. 1-13.
Shedlock, D. J. et al. "Induction of Broad Cytotoxic T Cells by Protective DNA Vaccination Against Marburg and Ebola." Molecular Therapy, vol. 21, No. 7, Jul. 1, 2013, pp. 1432-1444.
Sridhar, S. et al. "Effect of Dengue Serostatus on Dengue Vaccine Safety and Efficacy." The New England Journal of Medicine, vol. 379, No. 4, Jul. 26, 2018, pp. 327-340.
Sullivan, N. J. et al. "$CD8^+$ Cellular Immunity Mediates rAd5 Vaccine Protection Against Ebola Virus Infection of Nonhuman Primates." Nature Medicine, vol. 17, No. 9, Sep. 2011, pp. 1128-1131.
Tang, F. et al. "Lack of Peripheral Memory B Cell Responses in Recovered Patients with Severe Acute Respiratory Syndrome: A Six-Year Follow-Up Study." The Journal of Immunology, vol. 186, No. 12, Jun. 15, 2011, pp. 7264-7268.
Temperton, N. J. et al. "Longitudinally Profiling Neutralizing Antibody Response to SARS Coronavirus with Pseudotypes." Emerging Infectious Diseases, vol. 11, No. 3, Mar. 2005, pp. 411-416.
Théry, C. et al. "Indirect Activation of NaTve $CD4^+$ T Cells by Dendritic Cell-Derived Exosomes." Nature Immunology, vol. 3, No. 12, Dec. 2002, pp. 1156-1162.
Théry, C. et al. "Membrane Vesicles as Conveyors of Immune Responses." Nature Reviews Immunology, vol. 9, No. 8, Aug. 2009, pp. 581-593.
Trimble, et al. "A Phase I Trial of a Human Papillomavirus (HPV) DNA Vaccine for HPV16+ Cervical Intraepithelial Neoplasia 2/3." Clin Cancer Res. Author manuscript; available in PMC, May 7, 2010, pp. 1-15.
Valkenburg, S. A. et al. "Molecular Basis for Universal HLA-A*0201-Restricted $CD8^+$ T-Cell Immunity Against Influenza Virus." PNAS, vol. 113, No. 16, Apr. 19, 2016, pp. 4440-4445.
Van Niel, G. et al. "Shedding Light on the Cell Biology of Extracellular Vesicles." Nature Reviews Molecular Cell Biology, Jan. 17, 2018, pp. 213-228.
Weiskopf, D. et al. "Phenotype and Kinetics of SARS-CoV-2-Specific T Cells in COVID-19 Patients with Acute Respiratory Distress Syndrome." Science Immunology, vol. 5, No. 48, Jun. 26, 2020, pp. 1-10.
Wen, J. et al. "Dengue Virus-Reactive $CD8^+$ T Cells Mediate Cross-Protection Against Subsequent Zika Virus Challenge." Nature Communications, vol. 8, Article 1459, Nov. 13, 2017, pp. 1-11.
Wilson, J. A. et al. "Protection from Ebola Virus Mediated by Cytotoxic T Lymphocytes Specific for the Viral Nucleoprotein." Journal of Virology, vol. 75, No. 6, Mar. 15, 2001, pp. 2660-2664.
Woo, P. C. Y. et al. "Longitudinal Profile of Immunoglobulin G (IgG), IgM, and IgA Antibodies against the Severe Acute Respiratory Syndrome (SARS) Coronavirus Nucleocapsid Protein in Patients with Pneumonia Due to the SARS Coronavirus." Clinical and Vaccine Immunology, vol. 11, No. 4, Jul. 1, 2004, pp. 665-668.

(56) References Cited

OTHER PUBLICATIONS

Wu, L.-P. et al. "Duration of Antibody Responses after Severe Acute Respiratory Syndrome." Emerging Infectious Diseases, vol. 13, No. 10, Oct. 2007, pp. 1562-1564.

Wu, T. et al. "Lung-Resident Memory CD8 T Cells ($T_{RM}$) are Indispensable for Optimal Cross-Protection Against Pulmonary Virus Infection." Journal of Leukocyte Biology, vol. 95, No. 2, Feb. 2014, pp. 215-224.

Yip, M. S. et al. "Antibody-Dependent Infection of Human Macrophages by Severe Acute Respiratory Syndrome Coronavirus." Virology Journal, vol. 11, Article 82, May 6, 2014, pp. 1-11.

Yuchun, N. et al. "Neutralizing Antibodies in Patients with Severe Acute Respiratory Syndrome-Associated Coronavirus Infection." The Journal of Infectious Diseases, vol. 190, No. 6, Sep. 15, 2004, pp. 1119-1126.

Zhao, J. et al. "T Cell Responses are Required for Protection from Clinical Disease and for Virus Clearance in Severe Acute Respiratory Syndrome Coronavirus-Infected Mice." Journal of Virology, vol. 84, No. 18, Sep. 15, 2010, pp. 9318-9325.

Zheng, Y-H. et al. "Nef Increases the Synthesis of and Transports Cholesterol to Lipid Rafts and HIV-1 Progeny Virions." PNAS, vol. 100, No. 14, Jun. 24, 2003, pp. 8460-8465.

Zhi, Y. et al. "Identification of Murine CD8T Cell Epitopes in Codon-Optimized SARS-Associated Coronavirus Spike Protein." Virology, vol. 335, No. 1, Apr. 25, 2005, pp. 34-45.

Zhu, N. et al. "A Novel Coronavirus from Patients with Pneumonia in China, 2019." The New England Journal of Medicine, vol. 382, No. 8, Feb. 20, 2020, pp. 727-733.

\* cited by examiner

Vector

Nef$^{mut}$-GFP

Nef$_{G2A}$-GFP

SEQUENCE LISTING

```
<160> NUMBER OF SEQ ID NOS: 21

<210> SEQ ID NO 1
<211> LENGTH: 206
<212> TYPE: PRT
<213> ORGANISM: Human immunodeficiency virus type 1

<400> SEQUENCE: 1

Met Gly Cys Lys Trp Ser Lys Ser Ser Val Val Gly Trp Pro Ala Val
1               5                   10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Asp Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80
```

```
Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Pro
        115                 120                 125

Thr Gly Pro Gly Ile Arg Tyr Pro Leu Thr Phe Gly Trp Cys Tyr Lys
    130                 135                 140

Leu Val Pro Val Glu Pro Lys Leu Glu Glu Ala Asn Lys Gly Glu
145                 150                 155                 160

Asn Thr Ser Leu Leu His Pro Val Ser Leu His Gly Met Asp Asp Pro
                165                 170                 175

Gly Arg Glu Val Leu Glu Trp Arg Phe Asp Ser Arg Leu Ala Phe His
                180                 185                 190

His Val Ala Arg Glu Leu His Pro Glu Tyr Phe Lys Asn Cys
                195                 200                 205
```

<210> SEQ ID NO 2
<211> LENGTH: 621
<212> TYPE: DNA
<213> ORGANISM: Human immunodeficiency virus type 1

<400> SEQUENCE: 2

```
atgggttgca agtggtcaaa aagtagtgtg gttggatggc ctgctgtaag ggaaagaatg    60
agacgagctg agccagcagc agatggggtg ggagcagcat ctcgagacct agaaaaacat   120
ggagcaatca caagtagcaa tacagcagct accaatgctg attgtgcctg gctagaagca   180
caagaggagg aggaggtggg ttttccagtc acacctcagg tacctttaag accaatgact   240
tacaaggcag ctgtagatct tagccacttt ttaaaagaaa agggggggact ggaagggcta   300
attcactccc aacgaagaca agatatcctt gatctgtgga tctaccacac acaaggctac   360
ttccctgatt ggcagaacta cacaccagga ccaggggtta gatatccact gacctttgga   420
tggtgctaca agctagtacc agttgagcca gagaagttag aagaagccaa caaggagag   480
aacaccagct tgttacaccc tgtgagcctg catggaatgg atgacccggc gagagaagtg   540
ttagagtgga ggtttgacag ccgcctagca tttcatcacg tggcccgaga gctgcatccg   600
gagtacttca agaactgctg a                                              621
```

<210> SEQ ID NO 3
<211> LENGTH: 8
<212> TYPE: PRT
<213> ORGANISM: Human papillomavirus type 16

<400> SEQUENCE: 3

```
Asp Leu Tyr Cys Tyr Glu Gln Leu
1               5
```

<210> SEQ ID NO 4
<211> LENGTH: 9
<212> TYPE: PRT
<213> ORGANISM: Human papillomavirus type 16

<400> SEQUENCE: 4

```
Arg Ala His Tyr Asn Ile Val Thr Phe
1               5
```

<210> SEQ ID NO 5
<211> LENGTH: 9

```
<212> TYPE: PRT
<213> ORGANISM: Human immunodeficiency virus type 1

<400> SEQUENCE: 5

Thr Ala Ala Thr Asn Ala Asp Cys Ala
1               5

<210> SEQ ID NO 6
<211> LENGTH: 9
<212> TYPE: PRT
<213> ORGANISM: Human papillomavirus type 16

<400> SEQUENCE: 6

Lys Leu Pro Gln Leu Cys Thr Glu Leu
1               5

<210> SEQ ID NO 7
<211> LENGTH: 8
<212> TYPE: PRT
<213> ORGANISM: Human papillomavirus type 16

<400> SEQUENCE: 7

Tyr Asp Phe Ala Phe Arg Asp Leu
1               5

<210> SEQ ID NO 8
<211> LENGTH: 10
<212> TYPE: PRT
<213> ORGANISM: Ebola virus

<400> SEQUENCE: 8

Lys Phe Ile Asn Lys Leu Asp Ala Leu His
1               5                   10

<210> SEQ ID NO 9
<211> LENGTH: 9
<212> TYPE: PRT
<213> ORGANISM: Ebola virus

<400> SEQUENCE: 9

Asp Ala Val Leu Tyr Tyr His Met Met
1               5

<210> SEQ ID NO 10
<211> LENGTH: 16
<212> TYPE: PRT
<213> ORGANISM: Ebola virus

<400> SEQUENCE: 10

Leu Arg Ile Gly Asn Gln Ala Phe Leu Gln Glu Phe Val Leu Pro Pro
1               5                   10                  15

<210> SEQ ID NO 11
<211> LENGTH: 11
<212> TYPE: PRT
<213> ORGANISM: Ebola virus

<400> SEQUENCE: 11

Val Tyr Gln Val Asn Asn Leu Glu Glu Ile Cys
1               5                   10

<210> SEQ ID NO 12
<211> LENGTH: 9
<212> TYPE: PRT
<213> ORGANISM: Ebola virus
```

<400> SEQUENCE: 12

Asp Ala Val Leu Tyr Tyr His Met Met
1               5

<210> SEQ ID NO 13
<211> LENGTH: 8
<212> TYPE: PRT
<213> ORGANISM: Hepatitis C virus

<400> SEQUENCE: 13

Ile Thr Gln Met Tyr Thr Asn Val
1               5

<210> SEQ ID NO 14
<211> LENGTH: 11
<212> TYPE: PRT
<213> ORGANISM: Hepatitis C virus

<400> SEQUENCE: 14

Trp Tyr Glu Leu Thr Pro Ala Glu Thr Ser Val
1               5                   10

<210> SEQ ID NO 15
<211> LENGTH: 9
<212> TYPE: PRT
<213> ORGANISM: West Nile virus

<400> SEQUENCE: 15

Gly Tyr Ile Ser Thr Lys Val Glu Leu
1               5

<210> SEQ ID NO 16
<211> LENGTH: 15
<212> TYPE: PRT
<213> ORGANISM: West Nile virus

<400> SEQUENCE: 16

Asp Arg Arg Trp Cys Phe Asp Gly Pro Arg Thr Asn Thr Ile Leu
1               5                   10                  15

<210> SEQ ID NO 17
<211> LENGTH: 9
<212> TYPE: PRT
<213> ORGANISM: Influenza virus

<400> SEQUENCE: 17

Ala Ser Asn Glu Asn Met Glu Thr Met
1               5

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 18
ctagctagca cccaagtgtg taccggc                                           27

<210> SEQ ID NO 19
<211> LENGTH: 29
<212> TYPE: DNA
<213> ORGANISM: Artificial Sequence

```
-continued

<220> FEATURE:
<223> OTHER INFORMATION: Description of Artificial Sequence: Synthetic
      reverse primer

<400> SEQUENCE: 19
ccggaattct cagtgggtca gttgatggg                                        29

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      HLA-A.02-restricted MART-1 sequence

<400> SEQUENCE: 20

Ala Ala Gly Ile Gly Ile Leu Thr Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      HER2/neu sequence

<400> SEQUENCE: 21

Ile Leu His Asp Gly Ala Tyr Ser Leu
1               5
```

NUCLEOTIDE SEQUENCE EXPRESSING AN EXOSOME-ANCHORING PROTEIN FOR USE AS VACCINE

CROSS REFERENCE TO RELATED APPLICATIONS

This application is the National Stage of International Application No. PCT/IT2017/000223, filed Oct. 11, 2017, which claims the right of priority based on Italian application IT 102016000101794, filed Oct. 11, 2016, each of which is hereby incorporated by reference in its entirety.

SEQUENCE LISTING

The instant application contains a Sequence Listing which has been filed electronically in ASCII format and is hereby incorporated by reference in its entirety. Said ASCII copy, created on May 3, 2019, is named 43171US_CRF_sequencelisting.txt and is 6,478 bytes in size.

The present invention concerns a nucleotide sequence expressing an exosome-anchoring protein for use as vaccine. Particularly, the present invention concerns a nucleotide sequence expressing a fusion protein, said fusion protein comprising or consisting of an exosome-anchoring protein fused at its C-terminus with an antigen, or a DNA expression vector comprising said nucleotide sequence, for use as vaccine.

It is known that immune response protects from both external and internal health threats. In many cases, when the natural immunity cannot contain the development of the pathology, the immune response elicited by inoculation of immunogens can block the pathogenic process, as occurs, for instance, through the induction of neutralizing antibodies against several infective pathogens.

Differently, the identification, production, and marketing of CTL-based vaccines is much more restricted although there is a wide consensus about its potential usefulness against the development of chronic infections and tumor diseases.

Eliciting a strong and broad CTL immune response is expected to be of therapeutic relevance for the treatment of several pathologies. For instance, several lines of evidence suggest that cell-mediated immune responses are important in controlling HPV infection and, by consequence, the virus-associated neoplasia. In fact, either general immunosuppression, or poor anti-HPV CTL response associate with viral persistence and disease progression.

The most commonly used experimental techniques for the induction of antigen-specific CTL immunity are based on the use of viral vectors, peptides and inactivated pathogens. To date, however, no CTL immunogenic drug is available on the market.

DNA vaccination for the production of immunogenic proteins recognized successes. For instance, a DNA vaccine against Japanese encephalitis has been released in 2010 for human use (1). In addition, a veterinary DNA vaccine to protect horses from West Nile virus has been approved (2, 3). Also, a preliminary study in DNA vaccination against multiple sclerosis was reported as being effective (4). Altogether, these evidences support the idea that, in principle, DNA vaccination can have a perspective of applicability in humans. Among the advantages of DNA vaccination, ease of development and production, stability for storage, cost-effectiveness, and persistence of the immunogen should be mentioned. Theoretical disadvantages would be represented by the possible production of anti-DNA antibodies, and interference on the genetically-controlled mechanisms of cell growth. However, the major limitation is represented by the not adequate potency of the evoked immune response. For this reason, many vaccination protocols including the use of DNA for priming the immune response are followed by the inoculation of the immunogen under alternative formulations to boost the immunity.

Exosomes are vesicles of 50-100 nanometers released constitutively by all cell types. They are generated by the inward invagination of endosome membranes. These intraluminal vesicles form the multivesicular bodies (MVBs) which can traffic to the plasma membrane, to which they fuse thereby releasing their vesicular contents in the extra-cellular milieu. Nanovesicles showing both physical and biochemical features resembling exosomes but generated through direct extrusion of plasma membrane have been described in muscle cells (5, 6). While exosomes were previously thought to be exclusively devoted to secretion of waste cell material, it is now accepted that exosomes are part of the intercellular communication network. They incorporate messenger RNAs, microRNAs, DNA, and proteins which can be functional in target cells.

Their immunogenicity is basically a consequence of the amounts and quality of antigens they incorporate. Exosomes were investigated in terms of anti-tumor immunostimulatory agents, and in some cases they reach the approval for clinical trials (7-9). Exosomes spontaneously uploading tumor antigens, mainly trans-membrane proteins like gp100, TRP-1, Her2/neu, and CEA, have been found inducing activation of specific anti-tumor T cell immunity (10, 11). Clinical trials demonstrated both feasibility and good tolerance of exosomes as cell-free vaccines in tumor patients. However, their therapeutic efficacy appeared quite limited, posing the need of new methods to increase their immunogenicity. This issue has been faced by engineering foreign antigens to increase their display on the exosome membrane. In this regard, two strategies have been described so far. The first one exploits the binding of C1C2 domains of lactadherin to exosome lipids resulting in the association of the heterologous antigen with the external side of exosome membranes. The other one relies on coating exosomes with *Staphylococcus aureus* enterotoxin A tailed with a highly hydrophobic trans-membrane domain.

The budding of HIV requires the interaction with a number of cell factors also involved in exosome biogenesis, i.e., Alix, Tsg101, and several other components of the endosomal sorting complex required for transport (ESCRT). Also the envelope membranes of HIV and exosomes share many components, including lipid rafts, i.e., cell membrane microdomains enriched in cholesterol, phospholipids with saturated side chains, and sphingolipids. The convergence of exosome and HIV biogenesis implies the possibility that viral products incorporate in exosomes. It is the case of HIV-1 Nef which associates through anchoring its N-terminal myristoylation to lipid raft microdomains at the limiting membrane of MVB. Nef is a 27 kilodalton (kDa) protein lacking enzymatic activities, however acting as a scaffold/adaptor element in triggering activation of signal transducing molecules, in most cases upon association with lipid raft microdomains.

A $^{V}153^{L}$ $^{E}177^{G}$ Nef mutant incorporating at quite high levels in HIV-1 particles, HIV-1-based virus-like particles (VLPs) (12), and exosomes (13) has been previously identified. The efficiency of exosome incorporation still increases when this mutant was engineered with an N-terminal palmitoylation through $^{G}3^{C}$ mutation, expectedly consequence of an improved association with lipid rafts. This Nef mutant (referred to as $\text{Nef}^{mut}$) is defective for basically all Nef functions, and its efficiency of incorporation in nanovesicles does not change significantly when fused at its C-terminus with foreign proteins. Manipulating $\text{Nef}^{mut}$ allows the incorporation of high amounts of antigens of choice into exosomes which thus remain protected from external neutralization/degradation factors. It has been recently reported that $Nef^{mut}$-engineered exosomes produced in vitro induce an effective antigen-specific CTL response (14). Particularly, quite promising results using in vitro produced exosomes carrying HPV-E7 protein as immunogen (14) have been already obtained.

However, in view of a potential clinic application of these findings, this strategy would face with possible technical difficulties including standardization of industrial manufacturing, high cost-effectiveness, and storage of the immunogen. In addition, in vitro produced exosomes are expected to have a limited half-life upon injection, being also prone to clearance from the reticulum-endothelial system of the host through the recognition of the "non-self" molecules associated to the exosome membrane. On this subject, it has been documented that the half-life of either ex vivo isolated or in vitro produced exosomes lasts around 2 minutes after injection, showing a prompt accumulation in liver and spleen, and only small amounts of exosomes remain detectable after 4 hours.

In the light of above it is therefore apparent the need to provide for new immunotherapies able to overcome the disadvantages of the known therapies.

On this technical background, the present invention provides a new vaccine strategy based on the production of endogenous engineered exosomes which is able to overcome the disadvantages of known therapeutic strategies inducing CTL immune response for the treatment of infective and tumor diseases.

According to the present invention, it has been found that the administration of DNA vectors expressing $Nef^{mut}$-based fusion proteins into the host animal by intramuscular (i.m.) inoculation elicits a potent CTL immune response strongly inhibiting the growth of already implanted tumor cells. Several lines of evidence indicate that the production of endogenous engineered exosomes was on the basis of the observed anti-tumor effect.

Particularly, the results according to the present invention show: i) the ability of muscle cells to produce engineered exosomes after DNA transfection; ii) the reproducible induction of antigen-specific CTL immunity after inoculation of a vector expressing $Nef^{mut}$/E7 showing a strong anti-tumor effect in a therapeutic setting, and iii) the immunogenicity of exosomes isolated from plasma of DNA-inoculated mice reinfused in recipient mice.

In addition, whether and how efficiently the ectopic expression of $Nef^{mut}$ leads to the release of engineered exosomes have been investigated. Data obtained with $C_2C_{12}$ cells supported the idea that $Nef^{mut}$ accumulates into exosome-like nanovesicles released by murine muscle cells at levels similar to those detectable in human cells. The investigations did not include terminally differentiated muscle cells, i.e., the cell type most likely targeted by i.m. inoculation in mice. It has been assumed that in these cells the mechanisms underlying the vesicle intracellular trafficking do not change, at least qualitatively.

On this subject, the detection of engineered exosomes in plasma from mice inoculated i.m. with $Nef^{mut}$-based DNA vectors supported the idea that $Nef^{mut}$ can accumulate in exosomes released by differentiated muscle cells also. Theoretically, it cannot be excluded that at least part of injected DNA could target other cell types by means, for instance, of the diffusion of DNA in draining lymph nodes where it can be captured and internalized by dendritic cells (DCs). However, it is plausible that the DNA uptake by DCs was not relevant part of the mechanism of the here described $CD8^+$ T cell activation events considering that the sub-cute inoculation of $Nef^{mut}$/E7 expressing DNA, which is expected to preferentially target DCs, gave rise to a significantly fainter E7-specific $CD8^+$ T cell immune response (not shown).

The extents of $CD8^+$ T cell activation detected in DNA inoculated mice appeared much stronger that those which has been observed in mice injected with in vitro produced engineered exosomes (14). Even though direct comparative experiments cannot be run in view of the impossibility to compare the amounts of the two different immunogens, the DNA inoculation elicited an E7-specific $CD8^+$ T cell activation strong enough to be clearly detected without the in vitro stimulation/expansion of splenocytes, needed when mice were inoculated with exosomes produced in vitro by human cells (14). The apparently superior outcomes obtained with DNA injection was likely the consequence of the fact that cells expressing the inoculated DNA can establish a continuous source of immunogenic exosomes ready to be internalized by both local and distal APCs.

According to the present invention, several experimental evidences have been provided concerning the mechanism underlying the CTL immune response observed after DNA injection. In particular, the detection of fluorescent exosomes in plasma of mice inoculated with a vector expressing GFP fused with $Nef^{mut}$ proved that engineered exosomes were indeed produced upon DNA vector injection. In addition, $Nef^{mut}$ activities other than its accumulation in exosomes seemed unimportant for the $CD8^+$ T cell activation since it was detected in mice injected with vector expressing $Nef^{mut}$ but not with wild-type Nef. Consistently, it has been observed that the CTL response did not rely on the release of free antigens from DNA-targeted cells, as indicated by the lack of E7-specific $CD8^+$ T cell response in mice injected with E7-expressing vectors where the E7 extra-cellular shedding was witnessed by the anti-E7 antibody response. In addition, it has been proved that exosomes isolated from plasma of mice injected with vector expressing $Nef^{mut}$/E7, but not E7 alone, were immunogenic when injected in naïve, recipient mice.

Taken together, these experimental evidences were consistent with the idea that the production of immunogenic endogenous engineered exosomes was on the basis of the $CD8^+$ T cell activation. Notably, this immune response appeared both fast and strong enough to efficiently counteract the growth of syngeneic tumor cells implanted before the immunizations.

On the basis of the here presented experimental evidences, the most likely mechanism underlying the $CD8^+$ T cell activation induced by inoculation of DNA vectors expressing $Nef^{mut}$-based vectors can be summarized as reported on FIG. 1. Muscle cells expressing the injected DNA vector release engineered exosomes which are internalized by APCs. As previously demonstrated, the internalization of $Nef^{mut}$-based exosomes leads to cross-presentation of the associated antigens and, by consequence, priming of antigen-specific $CD8^+$ T cells. The boosting of the immune response ensured by the second DNA injection would be strengthened by the continuous production of exosomes from cells targeted by the inoculated DNA. Accordingly to what previously observed in mice inoculated with in vitro produced exosomes (14), neither anti-E7 nor anti-Nef antibodies were detected in plasma from inoculated mice, strongly suggesting that exosome-uploaded antigens basically elicit a TH-1 biased immune response.

Finally, in view of a possible application of this findings to human breast cancer, the following aspects were also investigated: i) whether the immunogenic stimulus induced by the engineered exosomes can break immune tolerance, and ii) their effectiveness when applied in human system. In particular, to test whether the immune activation induced by in vivo engineered exosomes can be strong enough to break tolerance, the widely investigated model of HER2/neu transgenic mice has been considered (15). Here, the rHER2/neu transgene is expressed in thymus, leading to a tolerance severely impairing the CD8$^+$ T branch, as proven by the fact that CD8$^+$ T lymphocytes escaping the tolerance are very poorly represented (16). Through IFN-$\gamma$ Elispot assay, we reproducibly assessed that two injections of DNA vector expressing Nef$^{mut}$ fused with the extra-cellular domain of HER2 (HER2-ECD) were sufficient to break the CD8$^+$ T tolerance towards HER2/neu. These results were relevant since a significant HER2/neu-specific CTL response was never found in these transgenic mice upon injection of HER2/neu-expressing DNA vectors (17-19).

Interestingly, it was found that this immune activation correlated with a delay in tumor development. This is the first time that a CTL-related but antibody-independent inhibition of tumor development has been observed in HER2/neu transgenic mice. On the other hand, the fact that the immunologic pressure generated by the HER2-ECD-specific CTL immune response was not sufficient to cure the tumor disease was not surprising for at least two reasons. First, in HER2/neu transgenic mice all mammary epithelial cells simultaneously express the oncogene, resulting in a synchronous development of multiple neoplastic lesions. Hence, the anti-tumor immunity can be overwhelmed by the multiplicity of transformation events. In addition, the intrinsic genetic instability of tumor cells can lead to escaping from the immune pressure through the so-called immune-editing mechanism summarized by the three "Es", i.e., elimination, equilibrium, and escape (20). In this way, the anti-tumor immune response selects for alterations in cancer cells able to evade the immune control. Of course, the effectiveness of such a mechanism is expected to increase with the number of concurrent tumor lesions.

To open the possibility to exploit the tool of the present invention in clinic, its effectiveness in human system was also demonstrated. To this end, experiments were set up using conditions reproducing the mechanism underlying the induction of antigen-specific CD8$^+$ T lymphocyte immune response previously described in mice (21). The outcome from a confocal microscope analysis was consistent with the idea that the product of DNA vector transfected in human primary muscle cells can be internalized by DCs through formation of engineered exosomes. Furthermore, data from cross-priming assays indicate that the production by transfected muscle cells of exosomes engineered for the incorporation of Nef$^{mut}$ or derivatives thereof is sufficient to generate a well-detectable antigen-specific CTL activity. The fact that the antigen-specific cross-priming was severely impaired when inhibitors of exosome biosynthesis were used was consistent with the idea that the delivery of engineered exosomes to DCs was a key step for the generation of the antigen-specific CTL activation. Overall, the results obtained with ex vivo cells indicate the absence of obvious restrictions in the use of the Nef$^{mut}$-based CTL vaccine platform in humans.

On the basis of the above, the CTL vaccine platform according to the present invention represents a novel therapy against solid tumors. Breaking tolerance towards tumor-associated self-antigens as well as improving the response against tumor-associated antigens represent the next frontier in terms of anti-tumor immunotherapy (22). CTL vaccine platform based on engineering endogenous exosomes according to the present invention has the potential to meet both end-points, hence representing a truly novel concept in terms of CTL immunization.

The here proposed strategy to induce CTL immunity based on engineered endogenous exosomes exploits the ease of production, storage, and delivery typical of DNA vaccines combined with the potent immunogenicity of antigens uploaded in exosomes upon fusion with Nef$^{mut}$ as well as its intrinsic great flexibility in terms of the choice of the immunogen.

According to the present invention, it has been provided a DNA vector called "Nef$^{mut}$ shuttle" conceived to easily insert and express the sequences of the antigen of choice.

From the structural point of view, the DNA vector according to the present invention may undergo improvements both in terms of transcriptional efficiency, for example by replacing the CMV-IE promoter with other promoters even more powerful, and/or inserting stabilizing sequences of the transcript (eg., Woodchuck Hepatitis Virus posttranscriptional Regulatory Elements, WPRE), and reducing to the minimum size the "exosome-anchoring protein" thus favoring the incorporation of the antigen fused to it.

Since according to the present invention, exosomes/nanovesicles can be engineered "in vivo" to incorporate large amounts of any antigen, the present biotechnology platform can be of therapeutic benefit against any disease susceptible to the attack of specific CTL.

The use for therapeutic purposes of vaccination based on DNA vectors expressing fusion products with the "exosome-anchoring protein" Nef$^{mut}$ according to the present invention is applicable to all pathologies that may benefit from an effective CTL immune response. Clearly, the number and origin of the antigens which can be engineered can be expanded in relation to the therapeutic strategies to deal with.

It is therefore specific object of the present invention a nucleotide sequence expressing a fusion protein, said fusion protein comprising or consisting of the exosome-anchoring protein of sequence SEQ ID NO:1 fused at its C-terminus with an antigen, or a DNA expression vector comprising said nucleotide sequence, for use in vaccine prevention and therapy, wherein SEQ ID NO:1 is the following sequence:

```
MGCKWSKSSV VGWPAVRERM RRAEPAADGV GAASRDLEKH

GAITSSNTAA TNADCAWLEA QEEEEVGFPV TPQVPLRPMT

YKAAVDLSHF LKEKGGLEGL IHSQRRQDIL DLWIYHTQGY

FPDWQNYPTG PGIRYPLTFG WCYKLVPVEP EKLEEANKGE

NTSLLHPVSL HGMDDPGREV LEWRFDSRLA FHHVARELHP

EYFKNC.
```

The nucleotide sequence or DNA expression vector according to the present invention can be administered preferably intramuscularly; other routes of administration can be aerosol administration (i.e. administration to the upper airway), intradermal, mucosal, sub-cute administration.

The antigen can be chosen from the group consisting of Human Papilloma virus antigen such as E6 and E7, HIV antigen such as Gag and Tat, Ebola virus antigen such as VP24, VP40, NP, and GP, West Nile virus antigen such as NS3, HBV antigen such as Core, HCV antigen such as Core, NS3, E1 and E2, Crimean-Congo virus antigen such as GP and NP, Influenza A virus antigen such as NP and M1, human melanoma antigen such as MAGE-A3 and MART-1, human tumor-associated antigens such as Her2/Neu, Hox B7.

As mentioned above, the nucleotide sequence expressing the exosome-anchoring protein of sequence SEQ ID NO:1 can be the following nucleotide sequence SEQ ID NO:2 (Nef$^{mut}$ nucleotide sequence):

```
atg ggt tgc aag tgg tca aaa agt agt gtg gtt gga tgg cct gct gta agg gaa aga atg aga cga gct gag cca gca gca gat ggg gtg gga gca gca tct cga gac cta gaa aaa cat gga gca atc aca agt agc aat aca gca gct acc aat gct gat tgt gcc tgg cta gaa gca caa gag gag gag gag gtg ggt ttt cca gtc aca cct cag gta cct tta aga cca atg act tac aag gca gct gta gat ctt agc cac ttt tta aaa gaa aag ggg gga ctg gaa ggg cta att cac tcc caa cga aga caa gat atc ctt gat ctg tgg atc tac cac aca caa ggc tac ttc cct gat tgg cag aac tac aca cca gga cca ggg gtt aga tat cca ctg acc ttt gga tgg tgc tac aag cta gta cca gtt gag cca gag aag tta gaa gaa gcc aac aaa gga gag aac acc agc ttg tta cac cct gtg agc ctg cat gga atg gat gac ccg gcg aga gaa gtg tta gag tgg agg ttt gac agc cgc cta gca ttt cat cac gtg gcc cga gag ctg cat ccg gag tac ttc aag aac tgc tga
```

The nucleotide sequence or DNA expression vector according to the present invention can be used for the prevention and treatment of diseases chosen from the group consisting of chronic infective diseases such as HBV, HCV and HIV, tuberculosis and malaria, acute infective diseases such as influenza, West Nile, Crimean-Congo hemorrhagic fever and Ebola diseases, tumors such as breast, pulmonary, prostate or bladder tumor.

The present invention concerns also a pharmaceutical composition comprising or consisting of a nucleotide sequence expressing a fusion protein, said fusion protein comprising or consisting of the exosome-anchoring protein of sequence SEQ ID NO:1 fused at its C-terminus with an antigen or a DNA expression vector comprising said nucleotide sequence, in association with one or more pharmaceutically acceptable excipients and/or adjuvants, such as an adjuvant of CD8+ T cells response (for instance Iscomatrix™ adjuvant), wherein SEQ ID NO:1 is the following sequence:

MGCKWSKSSV VGWPAVRERM RRAEPAADGV GAASRDLEKH

GAITSSNTAA TNADCAWLEA QEEEEVGFPV TPQVPLRPMT

YKAAVDLSHF LKEKGGLEGL IHSQRRQDIL DLWIYHTQGY

FPDWQNYPTG PGIRYPLTFG WCYKLVPVEP EKLEEANKGE

NTSLLHPVSL HGMDDPGREV LEWRFDSRLA FHHVARELHP

EYFKNC.

As mentioned above, the antigen can be chosen from the group consisting of Human Papilloma virus antigen such as E6 and E7, HIV antigen such as Gag and Tat, Ebola virus antigen such as VP24, VP40, NP and GP, West Nile virus antigen such as NS3, HBV antigen such as Core, HCV antigen such as Core, NS3, E1 and E2; Crimean-Congo virus antigen such as NP and GP; Influenza A virus antigen such as NP and M1; human melanoma antigen such as MAGE-A3 and MART-1; human tumor-associated antigens such as Her2/Neu, HoxB7.

According to an embodiment of the present invention, the nucleotide sequence expressing the exosome-anchoring protein of sequence SEQ ID NO:1 can be the following sequence SEQ ID NO:2:

```
atg ggt tgc aag tgg tca aaa agt agt gtg gtt gga tgg cct gct gta agg gaa aga atg aga cga gct gag cca gca gca gat ggg gtg gga gca gca tct cga gac cta gaa aaa cat gga gca atc aca agt agc aat aca gca gct acc aat gct gat tgt gcc tgg cta gaa gca caa gag gag gag gag gtg ggt ttt cca gtc aca cct cag gta cct tta aga cca atg act tac aag gca gct gta gat ctt agc cac ttt tta aaa gaa aag ggg gga ctg gaa ggg cta att cac tcc caa cga aga caa gat atc ctt gat ctg tgg atc tac cac aca caa ggc tac ttc cct gat tgg cag aac tac aca cca gga cca ggg gtt aga tat cca ctg acc ttt gga tgg tgc tac aag cta gta cca gtt gag cca gag aag tta gaa gaa gcc aac aaa gga gag aac acc agc ttg tta cac cct gtg agc ctg cat gga atg gat gac ccg gcg aga gaa gtg tta gag tgg agg ttt gac agc cgc cta gca ttt cat cac gtg gcc cga gag ctg cat ccg gag tac ttc aag aac tgc tga
```

The pharmaceutical composition can be administered preferably by intramuscular administration; other routes of administration can be aerosol administration (i.e. administration to the upper airway), intradermal, mucosal, sub-cute administration.

In addition, the present invention concerns a pharmaceutical composition as mentioned above for use in vaccine prevention and therapy for instance in the prevention and treatment of diseases chosen from the group consisting of chronic infective diseases such as HCV and HIV, tuberculosis and malaria, acute infective diseases such as influenza, West Nile, Crimean-Congo hemorrhagic fever and Ebola diseases, tumors such as breast, pulmonary, prostate or bladder tumor.

The nucleotide sequence, the DNA expression vector or the pharmaceutical composition comprising the same according to the present invention can be used in medical field as well as in veterinary field.

The present invention now will be described by an illustrative, but not limitative way, according to preferred embodiments thereof, with particular reference to enclosed drawings, wherein:

FIG. 1 shows the scheme of the mechanism underlying the CTL activation induced by the inoculation of $Nef^{mut}$-based DNA vectors. After injection with DNA vector expressing an antigen fused to $Nef^{mut}$, transfected muscle cells release both unmodified and engineered exosomes. The contents of these latter, once internalized by APC and cross-presented, induce the priming/activation of CD8$^+$ T lymphocytes specific for the antigens uploaded in endogenous engineered exosomes.

FIG. 2 shows the detection of engineered exosomes in supernatants of transfected murine muscle cells. A. FACS analysis of both human 293T and murine $C_2C_{12}$ muscle cells two days after transfection with either $Nef^{mut}$/GFP or $Nef_{G2A}$/GFP expressing vectors. M1 marks the range of positivity as established by the analysis of mock-transfected cells. Percentages of positive cells are reported. B. Quantification in terms of AchE activity of exosomes recovered by differential centrifugations of supernatants from the same number (i.e., 5×10$^6$) of both 293T and $C_2C_{12}$ transfected cells. C. Western blot analysis of exosomes from both 293T and $C_2C_{12}$ transfected cells. Nef-based products were detected in both cell lysates and exosomes, while β-actin and Alix served as markers for cell lysates and exosomes, respectively. Arrows sign the relevant protein products. Molecular markers are given in kDa. D. FACS analysis of exosomes from $C_2C_{12}$ transfected cells. 10 mU of exosomes from $C_2C_{12}$ cells transfected with either $Nef^{mut}$-GFP- or $Nef_{G2A}$-GFP-expressing vectors were analyzed by FACS in terms of both forward/side scatter (upper panels) and GFP fluorescence (lower panels). Quadrants indicate either the dimension of the detected particulate (upper panels), or the range of positivity as calculated by the analysis of exosomes from mock-transfected cells. Results are representative of two independent experiments.

FIG. 3 shows the detection of fluorescent nanovesicles in plasma from mice inoculated with a $Nef^{mut}$-GFP expressing DNA vector. A. Analysis of the expression of GFP-related products in muscle tissues from mice inoculated with the indicated DNA vectors. Magnification: 40×. B. C57 Bl/6 mice were inoculated i.m. with DNA vectors expressing the indicated products, and after 3 and 9 days exosomes were isolated from plasma by differential centrifugations. Then, equivalent amounts (i.e., 1 mU) of exosomes were bound to surfactant-free white aldehyde/sulfate latex beads, and finally assayed for their fluorescence. As control, 10 μU of exosomes isolated from the supernatants of 293T cells transiently transfected with $Nef^{mut}$-GFP vector were used (Ctrl+). Quadrants were set on the basis of the fluorescence of untreated beads. Percentages of positive events are indicated. Results are representative of two assays.

FIG. 4 shows the inoculation of $Nef^{mut}$/E7 DNA vector inducing an E7-specific CD8$^+$ T cell immune response in the absence of antibody production. CD8$^+$ T cell immune response in mice inoculated with DNA vectors expressing either E7 or $Nef^{mut}$/E7, or with empty vector. C57 Bl/6 mice (six mice per group) were inoculated two times with the different DNA vectors. Splenocytes recovered from mice were incubated with or without 5 μg/ml of either unrelated (not shown), E7, or Nef specific nonamers. Cell activation extents were evaluated by IFN-γ Elispot assay carried out in triplicate with 10$^5$ cells/well. As control, untreated cells were also incubated with 5 ng/ml of PMA and 500 ng/ml of ionomycin. Shown are the number of IFN-γ spot-forming cells (SFU)/10$^5$ cells from triplicate wells seeded with splenocytes from each inoculated mice. Intergroup means+SD of SFU were also reported. The results are representative of three independent experiments. *p<0.05. B. CTL assay carried out with CD8$^+$ T cells from mice inoculated with the indicated vectors. CD8$^+$ T cells isolated from splenocytes from different inoculated mice were pooled and cultured for 6 hours at different cell ratios (i.e., from 20:1 to 5:1) with EL-4 cells previously labeled with CFSE and pre-treated with either unrelated or E7 peptides for 16 h. Six h later, the EL-4 cell mortality levels were scored by FACS analysis upon 7-AAD labeling. Shown are the results representative of four independent experiments. C. Anti-E7 antibody detection in plasma from mice inoculated with the indicated DNA vectors. As internal positive control standard (Ctrl+), 1:10,000 dilutions of plasma from mice injected with 10 μg of either recombinant E7 or Nef proteins plus adjuvant were used. Shown are the mean absorbance values +SD of triplicates of plasma pooled from six mice per group.

Figure 5:
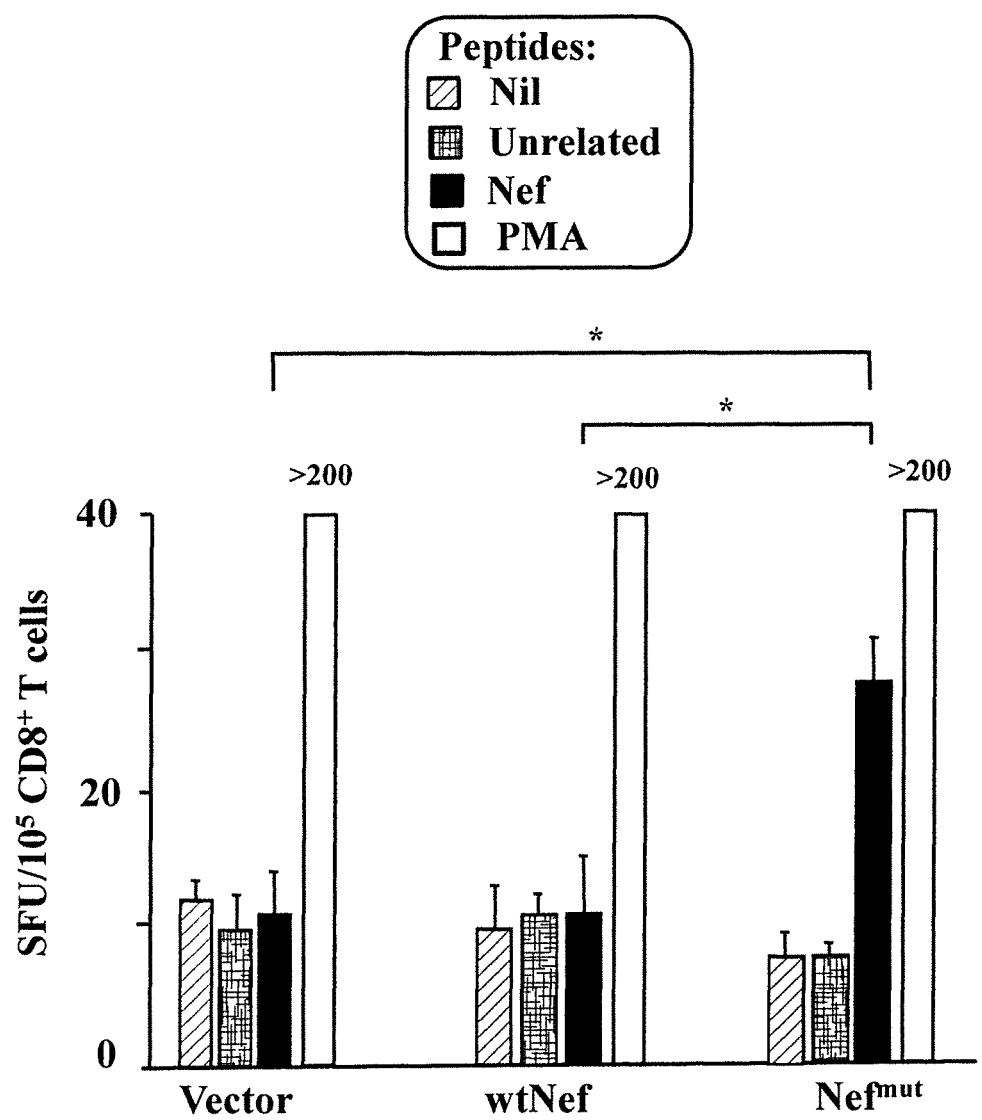

FIG. 5 shows that the injection of wtNef-expressing DNA vector fails to elicit Nef-specific CD8$^+$ T cell immune response in mice. Nef-specific CD8$^+$ T cell immune response in mice inoculated with DNA vectors expressing wtNef, $Nef^{mut}$, or with empty vector. C57 Bl/6 mice (four per group) were inoculated i.m. two times with the DNA vectors, and ten days after the last immunization, mice were sacrificed and splenocytes cultured in IFN-γ Elispot microwells for 16 hours in the absence or presence of either unrelated or Nef-specific nonamers. As control, untreated cells were also incubated with 5 ng/ml of PMA and 500 ng/ml of ionomycin. Shown are the mean+SD number of SFU/10$^5$ cells. The results are representative of two independent experiments. *p<0.05.

Figure 6:
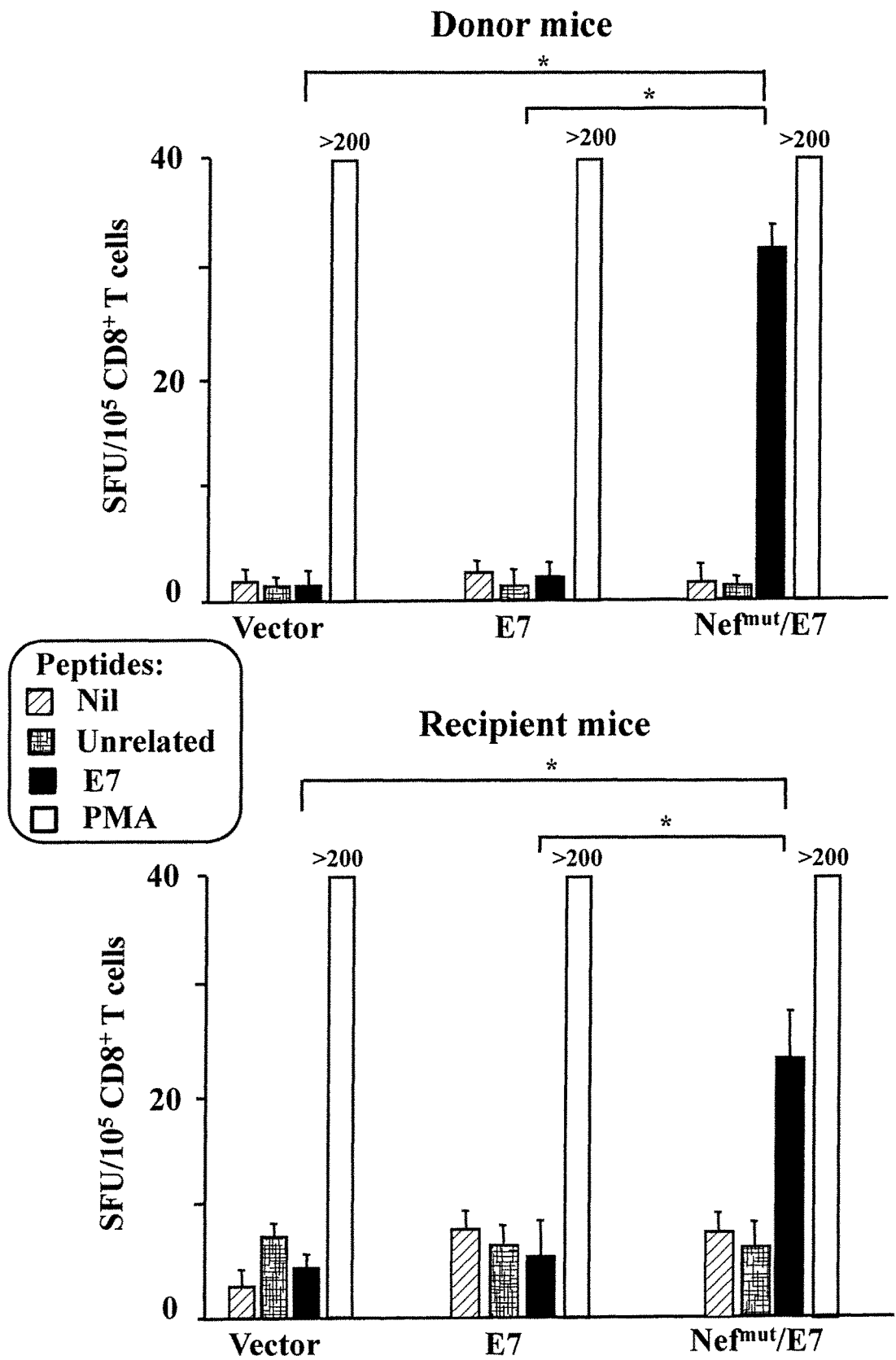

FIG. 6 shows E7-specific CD8$^+$ T cell immunity induced in mice injected with exosomes from mice inoculated with $Nef^{mut}$/E7 DNA vector. CD8$^+$ T cell immune response in mice inoculated with exosomes isolated from plasma of syngeneic mice previously injected with vectors expressing E7, $Nef^{mut}$/E7, or empty vector. C57 Bl/6 mice (8 for group, donor mice) were inoculated two times with the indicated DNA vectors, and ten days after the last inoculation, PBMCs were recovered from retro orbital bleeding and tested in IFN-γ Elispot assay for the presence of E7-specific CD8$^+$ T cell response (upper panels). Two days later, the mice were sacrificed, and exosomes isolated from plasma by differential centrifugations. Equivalent amounts of these exosomes were then used to inoculate syngeneic mice (3 per group) three times. Ten days after the last inoculation, the splenocytes were recovered and the CD8$^+$ T cell activation extents evaluated by IFN-γ Elispot assay carried out in triplicate (lower panel).

In all IFN-γ Elispot assays, cells were also incubated with 5 ng/ml of PMA and 500 ng/ml of ionomycin. Shown are the mean+SD number of SFU/10$^5$ cells. Results are representative of two independent experiments. *p<0.05.

FIG. 7 shows the therapeutic anti-tumor effect induced by i.m. inoculation of $Nef^{mut}$/E7 DNA vector. C57 Bl/6 mice were challenged with 2×10$^5$ TC-1 cells and 4 days later, when tumor masses were detectable by palpation, were inoculated with DNA vector expressing $Nef^{mut}$/E7 (seven mice) or, as control, $Nef^{mut}$, empty vector, or vehicle (four mice per group). The DNA inoculations were repeated at day 11 after tumor cell implantation, and the growth of tumor mass was followed over time. A. E7-specific CD8$^+$ T cell response by IFN-γ Elispot assay in PBMCs recovered from retro orbital bleeding 7 days after the last immunization, and cultivated for 16 hours in the presence of either unrelated or E7 peptides. As control, PBMCs were also incubated with 5 ng/ml of PMA and 500 ng/ml of ionomycin. Shown are the number of SFU/10$^5$ cells from triplicate wells seeded with splenocytes from each inoculated mice B. Determination of the tumor size during the 30-day observation time. C. Weight measure of tumors from mice injected with either Nef$^{mut}$ or Nef$^{mut}$/E7 DNA vectors at the time of sacrifice.

Shown are the values detected for each inoculated mouse. Results are representative of two independent experiments.

Figure 8:
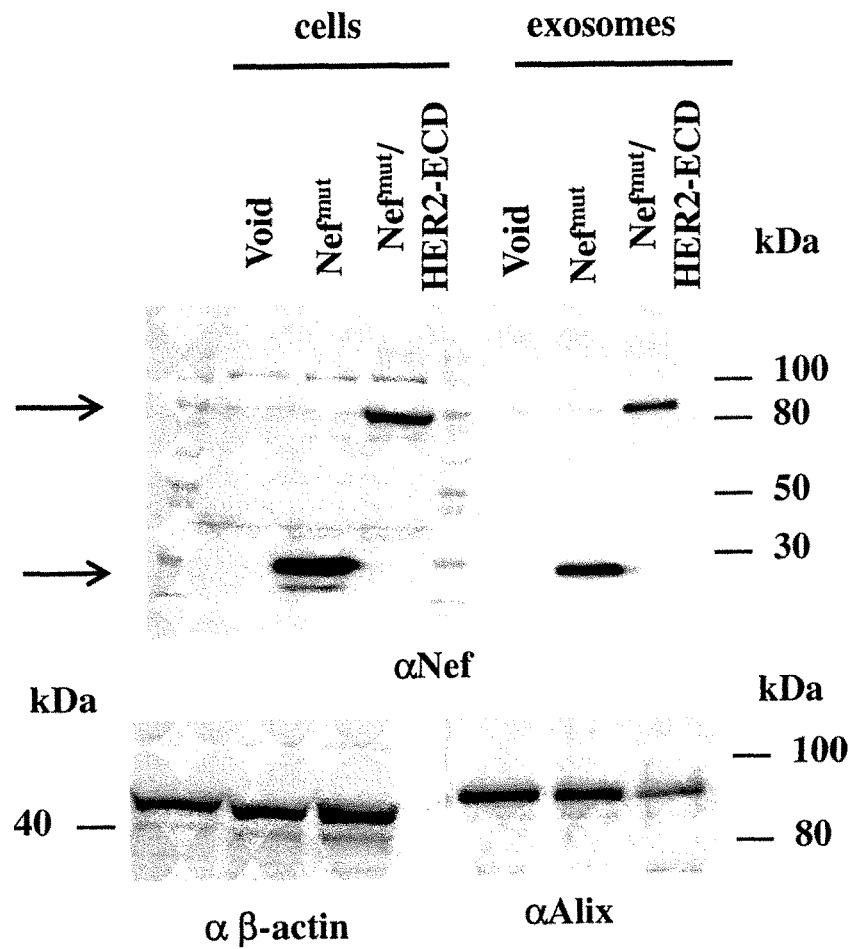

FIG. 8 shows the detection of exosomes engineered with HER2/neu ECD in supernatants of transfected cells. Western blot analysis of lysates of both cells and exosomes from cultures of 293T cells transfected with vector expressing either Nef$^{mut}$, Nef$^{mut}$/HER2 ECD, or the void vector. Nef-based products were detected in both cells and exosomes, while β-actin and Alix served as markers for cell lysates and exosomes, respectively. Arrows sign the relevant protein products. Molecular markers are given in kDa. Results are representative of five independent experiments.

Figure 9:
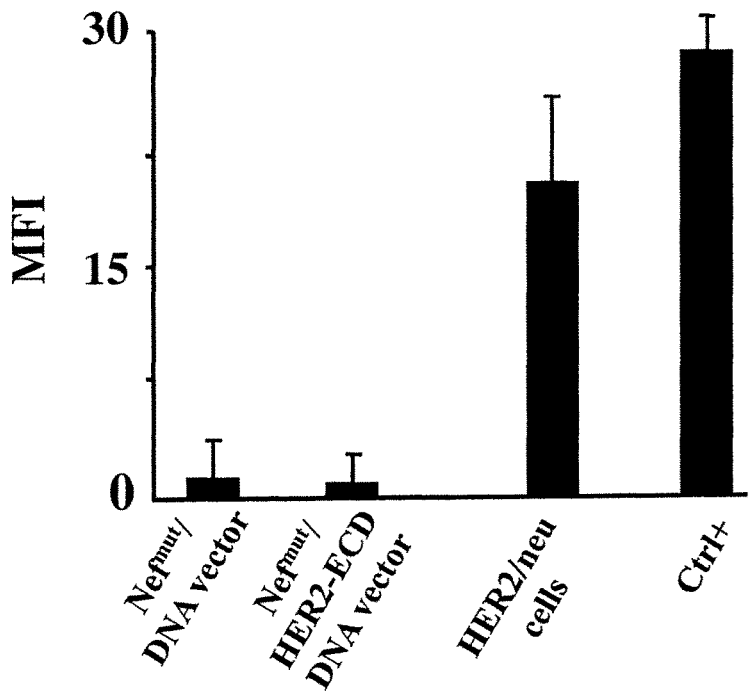

FIG. 9 shows the detection of anti-HER2/neu antibodies in plasma from inoculated mice. Plasma for mice injected with vectors expressing either Nef$^{mut}$ or Nef$^{mut}$/HER2-ECD were incubated with 293T cells transfected two days before with an HER2/neu expressing vector. After incubation with secondary Abs, the cells were fixed and FACS analyzed. As positive controls, both plasma from mice injected with lysates of 676-1-25 tumor cells constitutively over-expressing HER2/neu (HER2/neu cells), and an anti-HER2/neu mAb (Ctrl+) were used. Results are presented as mean values +SD of the mean fluorescent intensities (MFI) detected by FACS using plasma from each injected mouse, and are representative of two assays.

Figure 10:
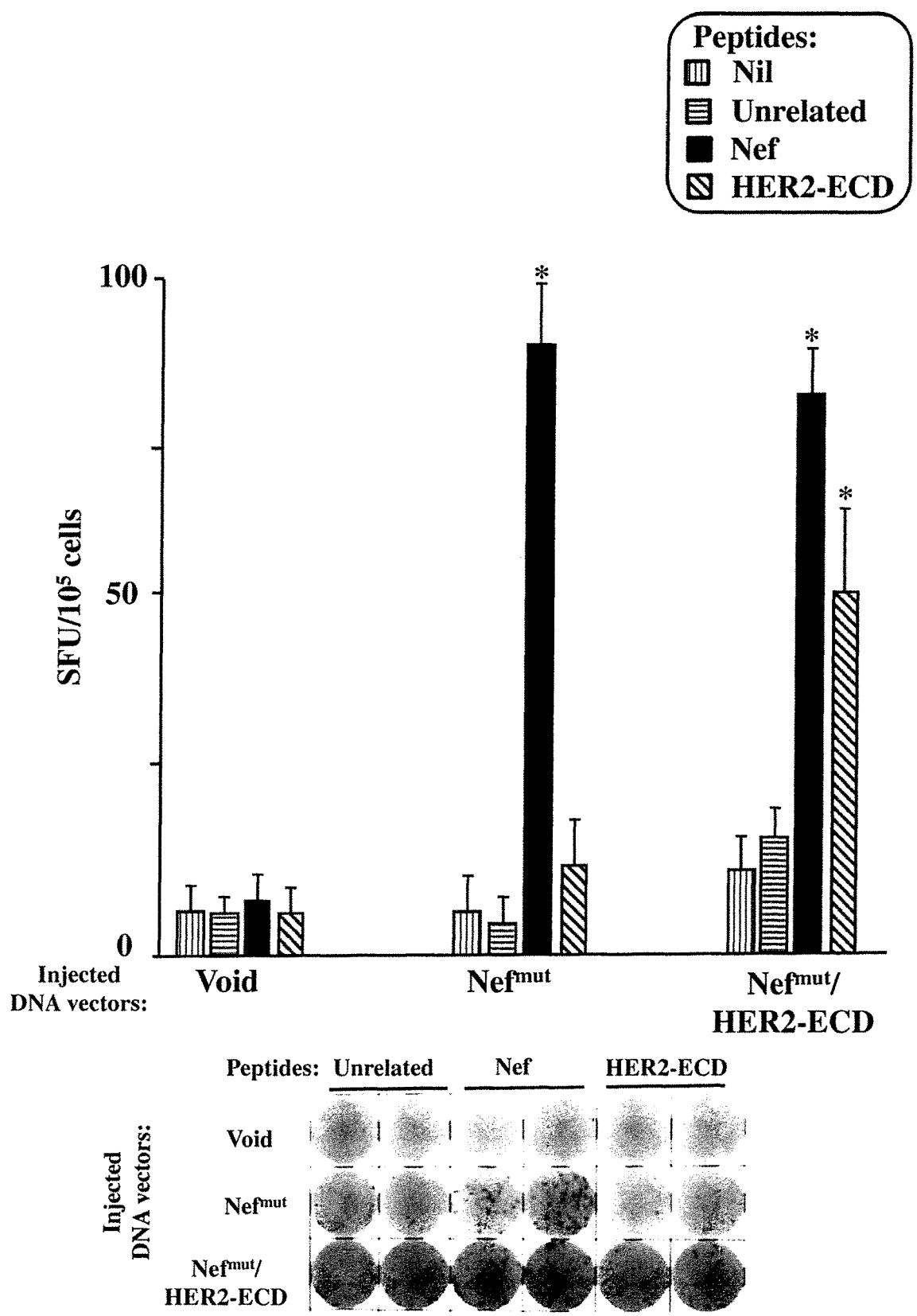

FIG. 10 shows the detection of HER2/neu-specific CD8$^+$ T cell immunity induced in mice upon injection of DNA vector expressing Nef$^{mut}$/HER2-ECD. CD8$^+$ T cell immune response in mice inoculated with DNA vectors expressing either Nef$^{mut}$ or Nef$^{mut}$/HER2-ECD, or with empty vector (Void). 129Sv-Neu T mice (five per group) were i.m. inoculated two times with the different DNA vectors. At the time of sacrifice, 10$^5$ splenocytes were incubated o.n. with or without 5 μg/ml of either unrelated, Nef-, or HER2-ECD-specific nonamers in either duplicate or triplicate IFN-γ Elispot microwells. As control, cells were also incubated in the absence of peptides (Nil). Shown are the mean number of IFN-γ spot-forming units (SFU)/10$^5$+SD. The results are representative of three independent experiments. *p<0.05. On the bottom, a developed IFN-γ Elispot plate from a representative assay is shown.

Figure 11A:
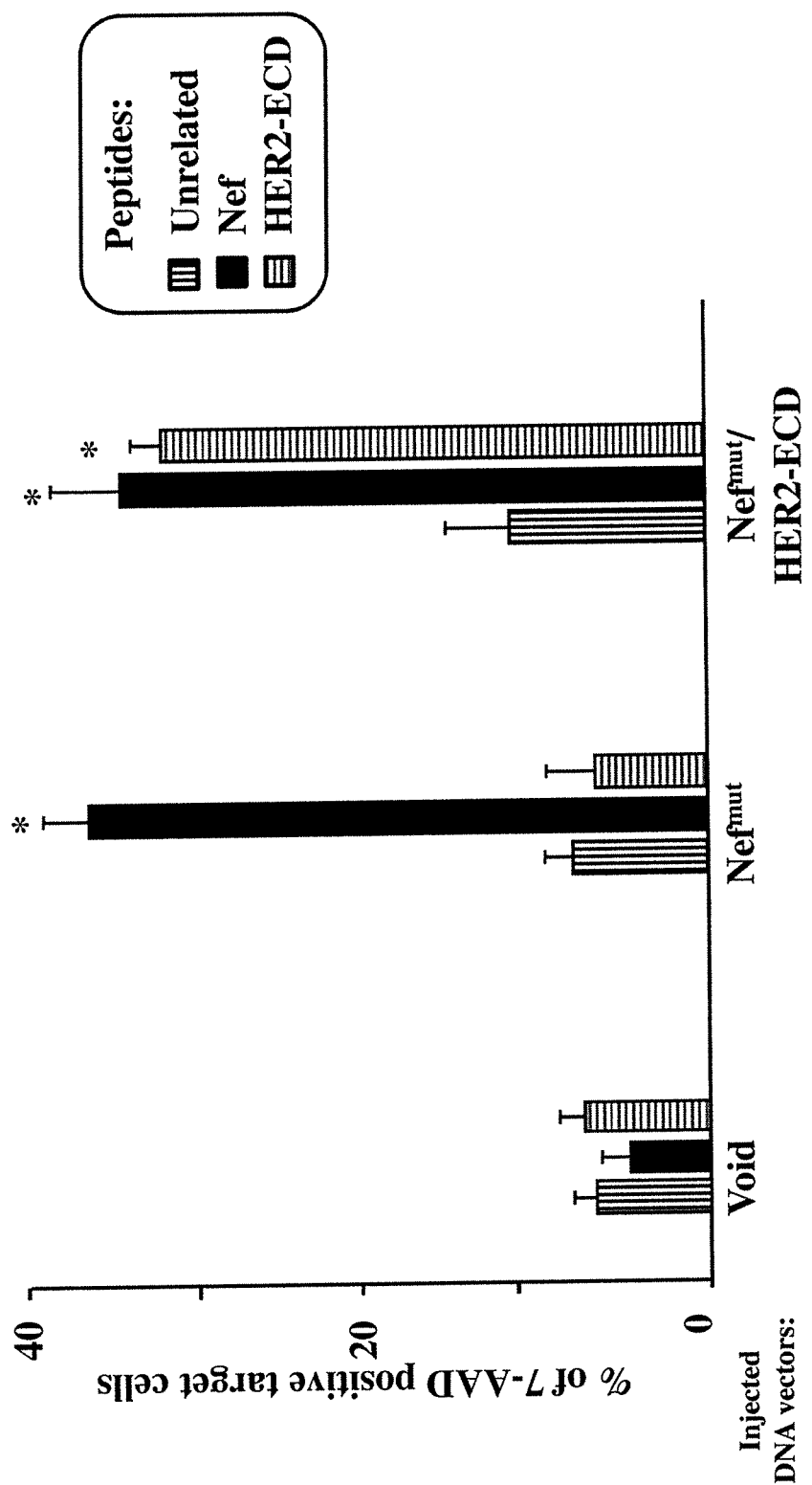
Figure 11B:
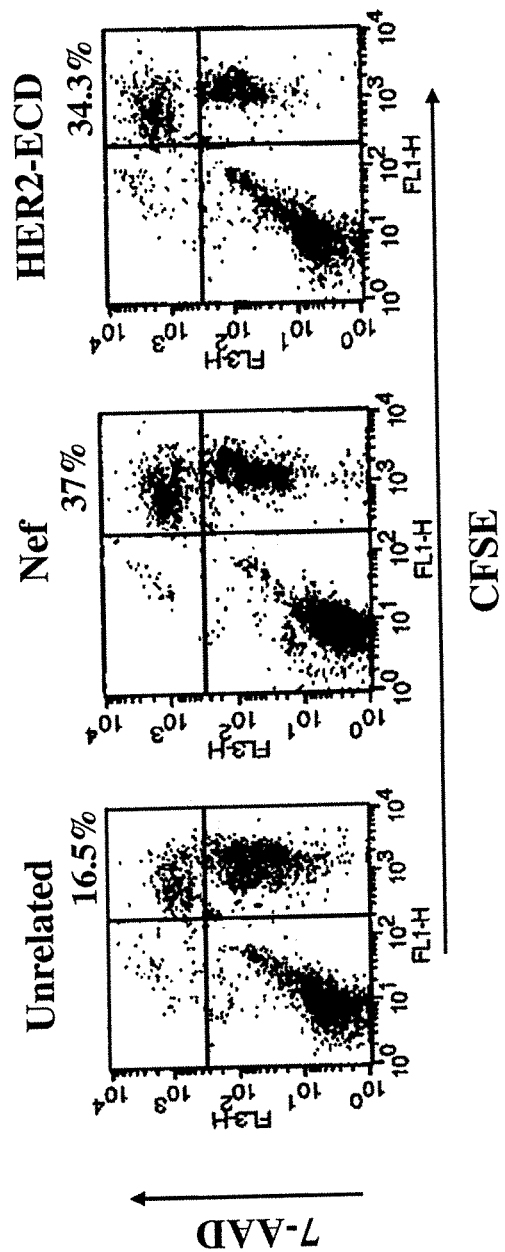

FIG. 11 shows the detection of the HER2/neu-specific CD8$^+$ T cell immunity induced in DNA injected mice couples with an antigen-specific CTL activity. CTL assay carried out with CD8$^+$ T cells from mice inoculated with the indicated vectors. CD8$^+$ T cells were isolated from pooled splenocytes, cultured in duplicate for 6 hours at 10:1 cell ratio with TC-1 cells previously labeled with CFSE, and treated for 16 h with either unrelated, Nef-, or HER2-ECD-specific peptides. Six h later, TC-1 cell mortality was scored by FACS analysis upon 7-AAD labeling. Shown are the mean values +SD calculated from three independent experiments. *p<0.05. Mean value of background conditions (i.e., co-culture of CD8$^+$ T lymphocytes from naïve mice with untreated TC-1 cells): 8.1±3.5. On the bottom, representative dot plots from FACS analysis of the co-cultures are shown. The percentages of double-fluorescent over the total of CFSE-positive cells are indicated.

Figure 12A:
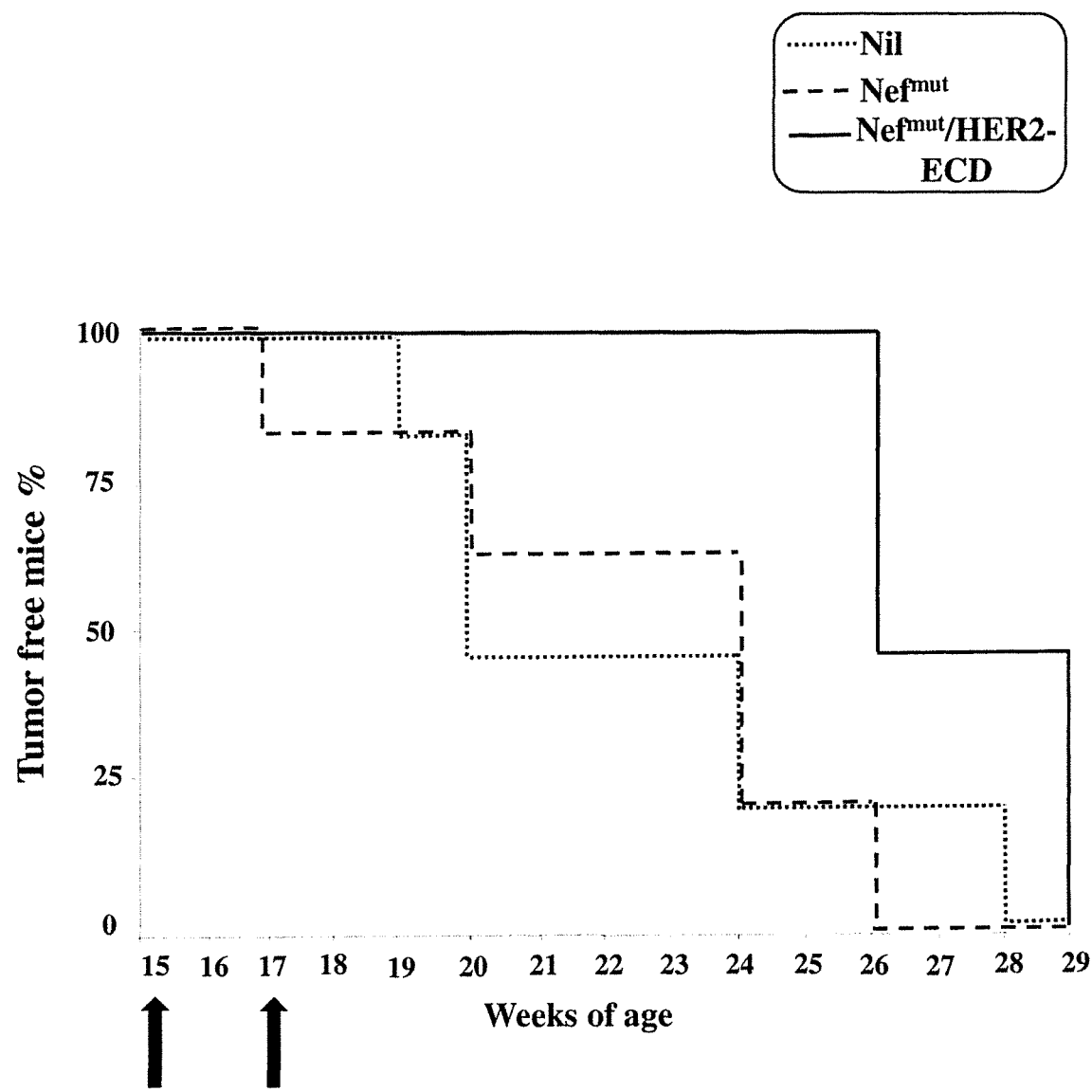
Figure 12B:
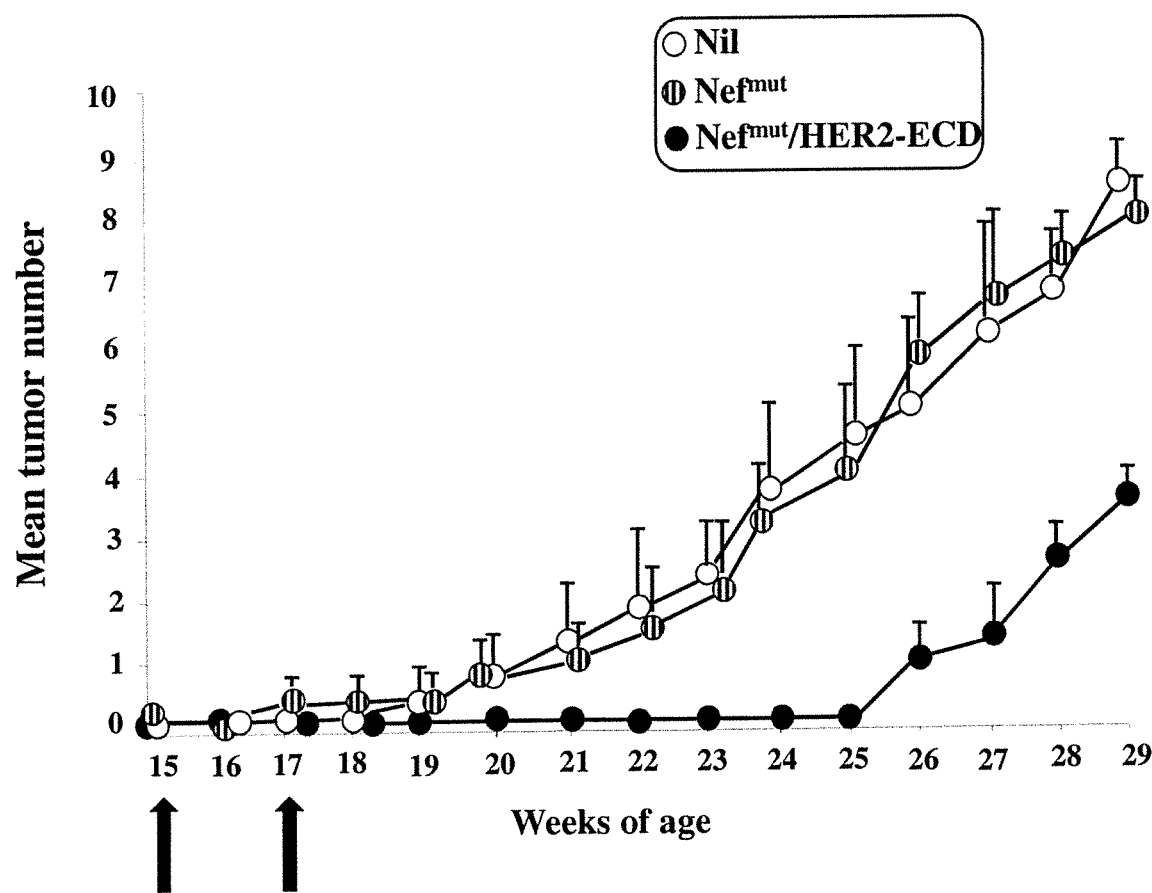

FIG. 12 shows the Anti-tumor effect induced by inoculation of Nef$^{mut}$/HER2-ECD DNA vector. 129Sv-NeuT mice (5 for group) were inoculated two times with either the indicated DNA vectors or the vehicle (Nil) at both 15 and 17 weeks of age. A. Tumor incidence, expressed as the number of mice with at least one tumor >1 mm in diameter. B. Tumor multiplicity, calculated as the cumulative number of tumors/total number of mice +SD. Data are representative of three independent experiments.

FIG. 13 shows the Internalization in iDCs of exosomes released by human primary skeletal muscle cells. A. FACS analysis of SKMC 2 days after transfection with vectors expressing either GFP, Nef$^{mut}$/GFP, or empty vector. Shown are GFP fluorescence levels as detected in a representative of five independent experiments. The percentages of GFP positive cells are indicated. M1: range of positivity. B. Confocal microscope analysis of co-cultures comprising iDCs and SKMC transfected with DNA vectors expressing either GFP or Nef$^{mut}$/GFP, the latter carried out in the presence or not of both GW4869 and spiroepoxide. Slides were stained with both DAPI (blue fluorescence) and anti-CD45 mAb (red fluorescence) before analysis. For co-cultures comprising Nef$^{mut}$/GFP-transfected SKMC, two sections of the same field are reported, the first one highlighting CD45 positive cells (top panel, black arrows), whereas in the image at the bottom, both Nef$^{mut}$/GFP-expressing SKMC (greenblack arrow) and regions of fluorescence accumulation into iDCs (white arrows) are indicated.

FIG. 14 shows the Nef-specific CTL activity elicited by human DCs co-cultivated with muscle cells expressing Nef$^{mut}$-based DNA vectors. A. Scheme of the cross-priming assays. SKMC were transfected and, 48 hours later, put in co-culture with iDCs which, after additional 24 hours, were isolated and matured. Autologous PBLs were then added to mDCs, and the co-cultivation was carried out for 7 days. Afterwards, the PBL stimulation was repeated, and after additional 7 days, CD8$^+$ T lymphocytes were isolated and tested in CTL assays through co-cultivation with syngeneic target cells. B. Western blot analysis of cell lysates from either parental or Nef$^{mut}$ stably transfected MCF-7 cells. Filters were incubated with either anti-Nef or anti-β-actin Abs. Arrow signs the relevant protein product. Molecular markers are given in kDa. C. CTL assay carried out by co-cultivating primed CD8$^+$ T lymphocytes with MCF-7 cells expressing or not Nef$^{mut}$ in a 10:1 cell ratio. Results were presented as mean values +SD calculated from triplicate conditions of three independent experiments. *p<0.05. Mean value of background conditions (i.e., co-culture of naïve CD8$^+$ T lymphocytes with MCF-7): 11.9±5.

Figure 15:
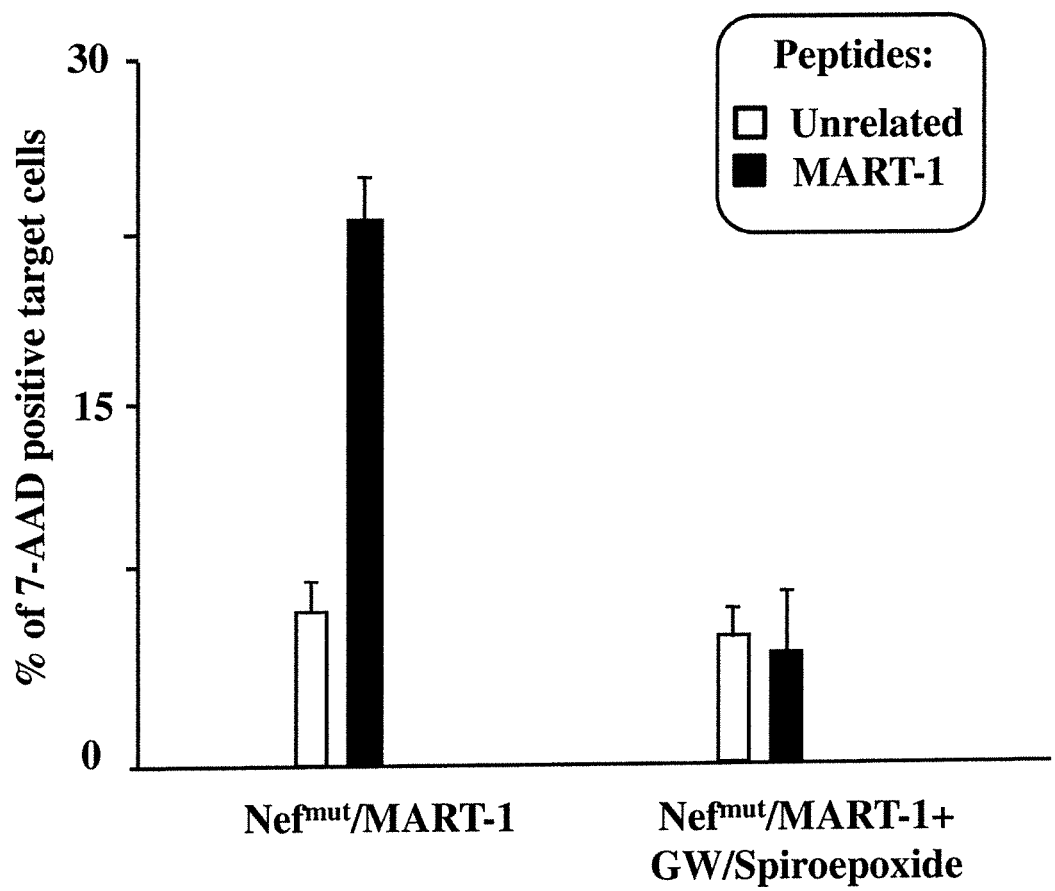

FIG. 15 shows that the treatment with inhibitors of exosome synthesis blocks the cross-priming induced by DCs isolated from co-cultures with transfected SKMC. SKMC were transfected with a DNA vector expressing the Nef$^{mut}$/MART-1 fusion product and, after 2 days, put in co-culture with iDCs in the presence or not of both GW4869 and spiroepoxide. After 16 hours, iDCs were isolated, matured, and put in co-culture with autologous PBLs. After two cycles of stimulation, CD8$^+$ T lymphocytes were isolated and challenged in a CTL assay by 10:1 co-cultivations with CFSE-labeled, syngeneic B-LCLs previously treated with either unrelated or MART-1 specific peptides. Shown are the mean percentages of target cell mortality +SD calculated from triplicate conditions of three independent experiments.

Mean value of background conditions (i.e., co-culture of naïve CD8+ T lymphocytes with untreated syngeneic B-LCLs): 7.3±2.1

EXAMPLE 1

Study of Anti-Tumor HPV E7-specific CTL Activity Elicited by In Vivo Engineered Exosomes Produced Through DNA Inoculation Materials and Methods Molecular Constructs and Cell Cultures All molecular constructs were based on IE-CMV-promoted vectors. The constructions of vectors expressing $Nef^{mut}$ (13), $Nef^{mut}$-GFP (13), $Nef_{G2A}$-GFP (23), wtNef (24), and HPV-E7 (25), have been already described. 293T, murine muscle $C_2C_{12}$, and HPV-E7 expressing TC-1 tumor cells were grown in Dulbecco's modified Eagle's medium plus 10% heat-inactivated fetal calf serum (FCS). Transfection assays were carried out using the Lipofectamine 2000-based method, which in the case of $C_2C_{12}$ cells was modified by adding liposomes on freshly trypsinized cells. Both mouse splenocytes and EL-4 cells, i.e., murine thymic lymphoma CD4+ T cells originally obtained from C57 Bl/6 mice upon treatment with 9,10-dimethyl-1,2-benzanthracene, were cultivated in RPMI medium supplemented with 10% FCS.

Exosome Isolation, Detection, and Characterization

Exosomes were isolated from cell supernatants through differential centrifugations. In detail, supernatants were centrifuged at 500×g for 10 min. Then, supernatants underwent differential centrifugations consisting in a first ultracentrifugation at 10,000×g for 30 min. Supernatants were then harvested, filtered with 0.22 µM pore size, and ultracentrifuged at 70,000×g for 1 h. Pelleted vesicles were resuspended in 1×PBS, and ultracentrifuged again at 70,000×g for 1 h. Afterwards, pellets were resuspended in 1:100 of the initial volume of 1×PBS. The recovery of exosomes from plasma of inoculated mice was carried out in a similar way except that samples were 5-fold diluted before starting centrifugations whose running times were doubled. The amounts of recovered exosomes were evaluated by measuring the activity of acetylcholinesterase (AchE), i.e., a classical exosome marker, through the Amplex Red kit (Molecular Probes) following the manufacturer's recommendations. The AchE activity was measured as mU/mL, where 1 mU is defined as the amount of enzyme which hydrolyzes 1 pmole of acetylcholine to choline and acetate per minute at pH 8.0 at 37° C.

Fluorescent exosomes from transfected cell cultures were either directly detected by FACS (Gallios, Beckman Coulter), or, in the case of exosomes isolated from plasma, analyzed upon binding with aldehyde/sulfate latex beads (Invitrogen Molecular Probes). To this end, samples were incubated with 5 µl of beads overnight at r.t. on a rotating plate, and then washed, resuspended in 1×PBS-2% v/v formaldehyde, and FACS analyzed.

For western blot analysis of exosomes, equivalent amounts of nanovesicles were lysed in PBS, 1% Triton X-100 in the presence of anti-proteolytic agents, and then separated by 10% SDS-PAGE. Meanwhile, western blot analysis was carried out also on lysates of transfected cells by washing cells twice with 1×PBS (pH 7.4) and lysing them for 20 min on ice with lysis buffer (20 mM HEPES pH 7.9, 50 mM NaCl, 10 mM EDTA, 2 mM EGTA, 0.5% nonionic detergent IGEPAL CA-630, supplemented with anti-proteolytic agents. Whole cell lysates were centrifuged at 6,000×g for 10 min at 4° C. Protein concentration of cell extracts was determined by the Lowry protein quantitation assay. Aliquots of 30 to 50 µg of total proteins were resolved by 10% SDS-PAGE. Proteins were transferred by electroblotting on a 0.45 µm pore size nitrocellulose membrane (Amersham) overnight using a Bio-Rad Trans-Blot. Filters were revealed using 1:1000 diluted sheep anti-Nef antiserum ARP 444 (a generous gift of M. Harris, University of Leeds, Leeds, UK), and both 1:250 diluted anti-β actin AC-74 mAb from Sigma, and anti-Alix H-270 polyclonal Abs from Santa Cruz.

Mice Immunization and Detection of IFN-γ Producing CD8+ T Lymphocytes

All studies with animals here described have been approved by the Ethical Committee of the Istituto Superiore di Sanità, Rome, Italy (protocol n. 555/SA/2012) according to Legislative Decree 116/92 which has implemented in Italy the European Directive 86/609/EEC on laboratory animal protection. Animals used in the research have been housed and treated according to the guidelines inserted in here above mentioned Legislative Decree. C57 Bl/6 mice were purchased from Charles River Laboratories, and inoculated i.m. two times at ten day intervals with 50 µg each back leg of plasmid DNA purified with endotoxin-free Qiagen kit. Mice were also inoculated subcutaneously (s.c.) with 6 mU equivalents of AchE activity of exosomes purified from plasma of mice injected with DNA vectors for three times at ten day intervals, and sacrificed ten days after the last immunization. To detect both E7- and Nef-specific CD8+ T cell immune responses, splenocytes were put in culture in IFN-γ Elispot microwells (Millipore) in the presence of 5 µg/ml of either HPV-E7 or HIV-1 Nef 8- or 9-mer peptides already identified to efficiently bind the H-2 $K^b$ complex of C57 Bl/6 mice, i.e., DLYCYEQL (aa 21-28) (SEQ ID NO: 3) and RAHYNIVTF (aa 49-57) (SEQ ID NO: 4) for E7 (HPV-16 Gene Bank accession n. AAD33252.1), and TAATNADCA (aa 48-56) (SEQ ID NO: 5) for Nef (HIV-1, F12 strain, accession number EMBL Z11530). H-2 $K^b$ binding HPV E6-specific KLPQLCTEL (aa. 18-26) (SEQ ID NO: 6) and YDFAFRDL (aa 50-57) (SEQ ID NO: 7) peptides (HPV-16 Gene Bank accession n. AAD33253.1) were used as unrelated peptides. After o.n. incubation, IFN-γ Elispot plates were developed (Mabtech AB), and spot-forming cells were analyzed and counted using an Elispot reader (A.EL.VIS. Elispot reader and Analysis software GmbH).

Fluorescence Microscope Analysis

For analysis by fluorescence microscope, 7 µM slices from quadriceps of inoculated mice were prepared by cryostat (Leika CM 3050) sectioning and placed to slides. The slices were then incubated with 4',6'-diamidino-2-phenylindole (DAPI, Vector Laboratories) together with an antifade mounting medium. Finally, coverslips were mounted to slides which were then observed with a Zeiss Axioskop 2 Plus fluorescence microscope.

CTL Assay

CD8+ T cells were isolated from splenocytes of inoculated mice by positive immunomagnetic selection (Miltenyi Biotec). They were put in co-culture for 6 hours in RPMI 10% FCS with EL-4 cells previously labeled with carboxyfluorescein succinimidyl ester (CFSE, Invitrogen), and treated overnight with either E7 or unrelated peptides. The co-cultures were run at different cell ratios (i.e., from 20:1 to 5:1 effector/target cells) in 200 µl of RPMI 20% in U-bottom 96 well plates. Afterwards, EL-4 cell mortality was scored by FACS analysis soon after addition of 7-AAD at final concentration of 1 µg/ml.

Detection of Anti-E7 and Anti-Nef Antibodies in Plasma

Plasma from inoculated mice were pooled, and two-fold serial dilutions starting from 1:10 were assayed for the presence of anti-E7 Abs. The end-point dilution corresponded to a <0.1 OD absorbance at 450 nm. Each plasma was assayed in triplicate, and the mean of the absorbance value was taken as final readout. Both recombinant E7 and Nef were used for the assay. The proteins were adsorbed overnight at 4° C. in carbonate buffer (pH 9.4) into Maxisorp microtiter plates (NUNC) at the concentrations of 0.25 µg/well. After a blocking step of 2 h of at 37° C. in PBS containing 3% non-fat dry milk (NFDM), plates were incubated at 37° C. for 1 h with 100 µL of serially diluted plasma in 1% NFDM-PBS. Specific antigen-antibody complexes were detected by a peroxidase-conjugated goat anti-mouse IgG (GE Healthcare Ltd) using tetramethyl benzidine as substrate. After 30 min at room temperature, the enzymatic reaction was stopped by adding 50 µl of 1 M sulphuric acid/well. Washing steps were done with 200 µl/well of PBS containing 0.05% Tween-20 in an automatic washer.

Anti-Tumor Effects of $Nef^{mut}/E7$ Exosomes

The anti-tumor activity induced by the inoculation of $Nef^{mut}$/E7-expressing vector was evaluated in mice previously challenged with $2\times10^5$ TC-1 cells. DNA inoculations were performed 4 and 11 days after tumor cell challenge following the above reported protocol, and only in mice which developed palpable tumors. Tumor growth was monitored by visual inspection, palpation, and measurement of tumor nodule diameter calculated as (length×width$^2$)/2. At the end of the observation time, tumors were explanted and weighted.

Statistical Analysis

When appropriate, data are presented as mean+standard deviation (SD). In some instances, the paired Student's t-Test was used and confirmed using the non-parametric Wilcoxon rank sum test. $p<0.05$ was considered significant.

Results

Detection of Engineered Exosomes Released by DNA Transfected Murine Muscle Cells Muscle cells represent the ideal target for a both efficient and stable expression of ectopic DNA upon in vivo administration. The aim was to express $Nef^{mut}$-based DNA vectors in vivo to engineer the exosomes constitutively released by cells expressing the inoculated DNA. These endogenous exosomes were expected to show characteristics at least similar to those produced in tissue cultures in terms of induction of antigen-specific CTL immune responses.

As already assessed in human cell types of different origin, whether the internalization of a $Nef^{mut}$-expressing DNA vector in murine muscle cells was sufficient for the production of engineered exosomes has been preliminarily investigated. Notably, murine muscle cells release nanovesicles with exosome-like characteristics whose biogenesis, however, differ from that of MVB-generated exosomes. For the sake of clarity, exosome-like nanovesicles released by murine muscle cells are here defined exosomes.

Figure 2A:
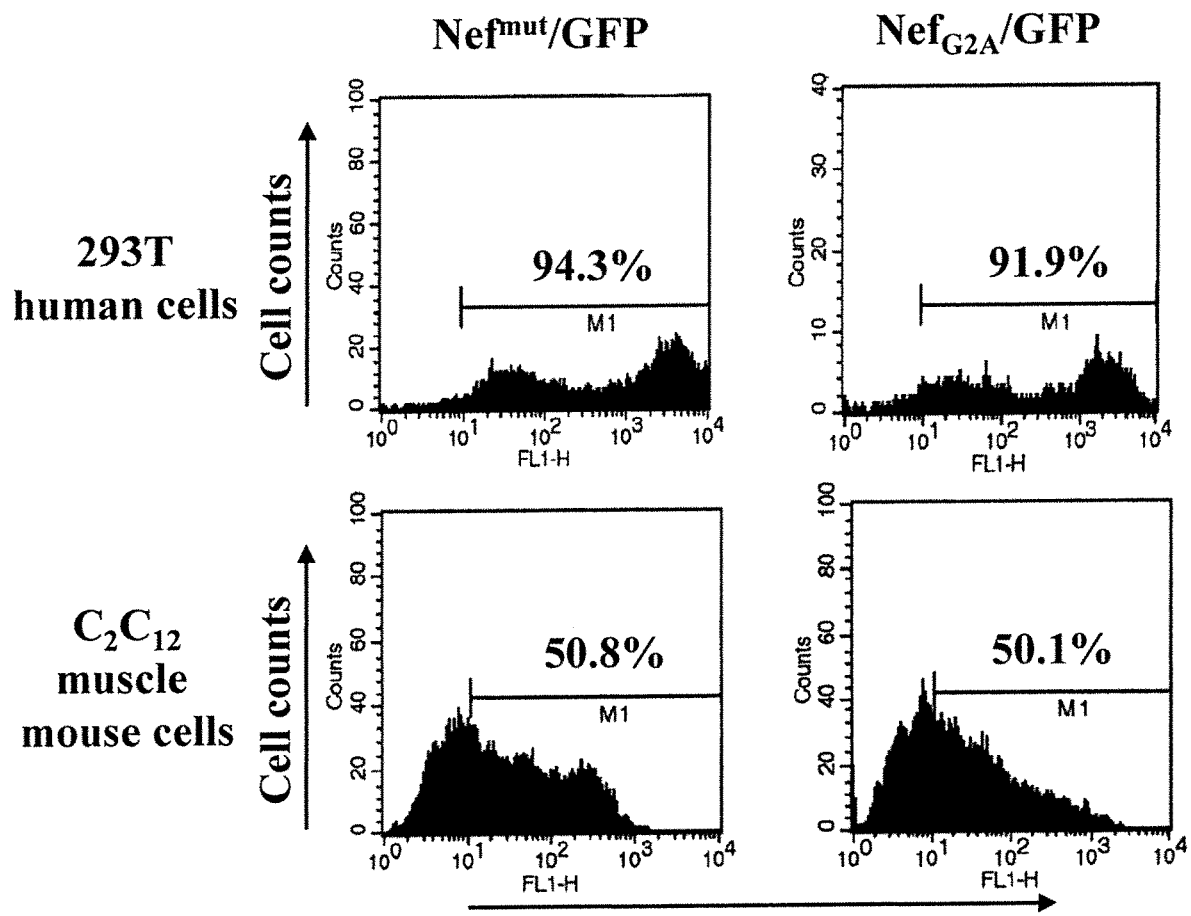
Figure 2B:
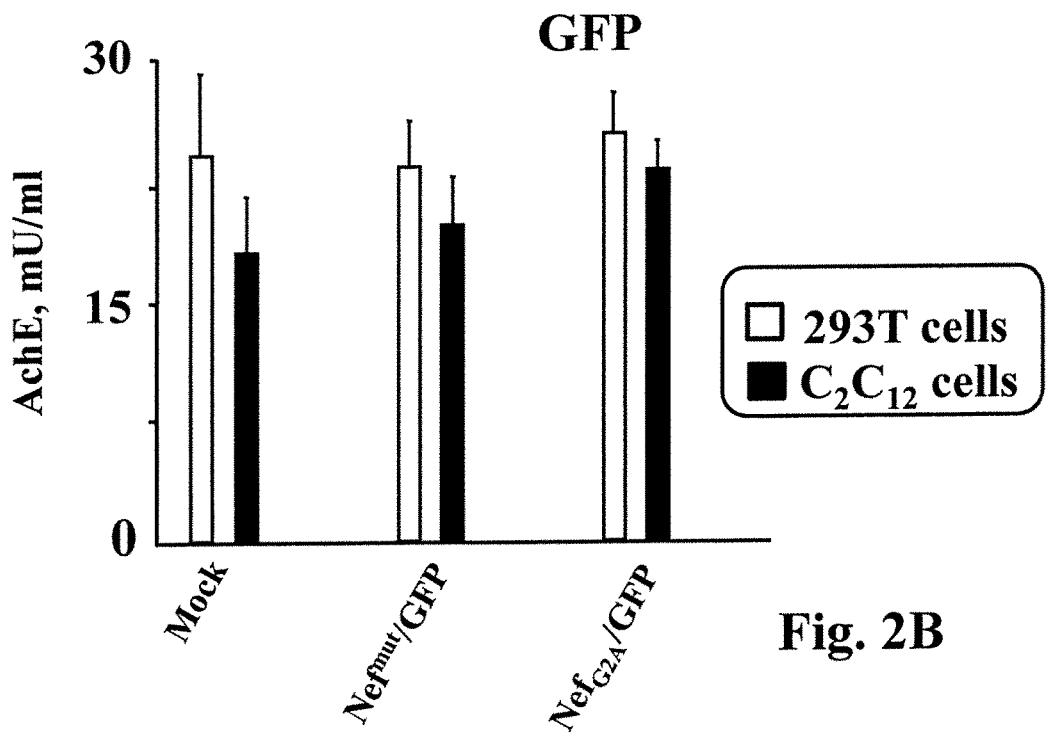
Figure 2C:
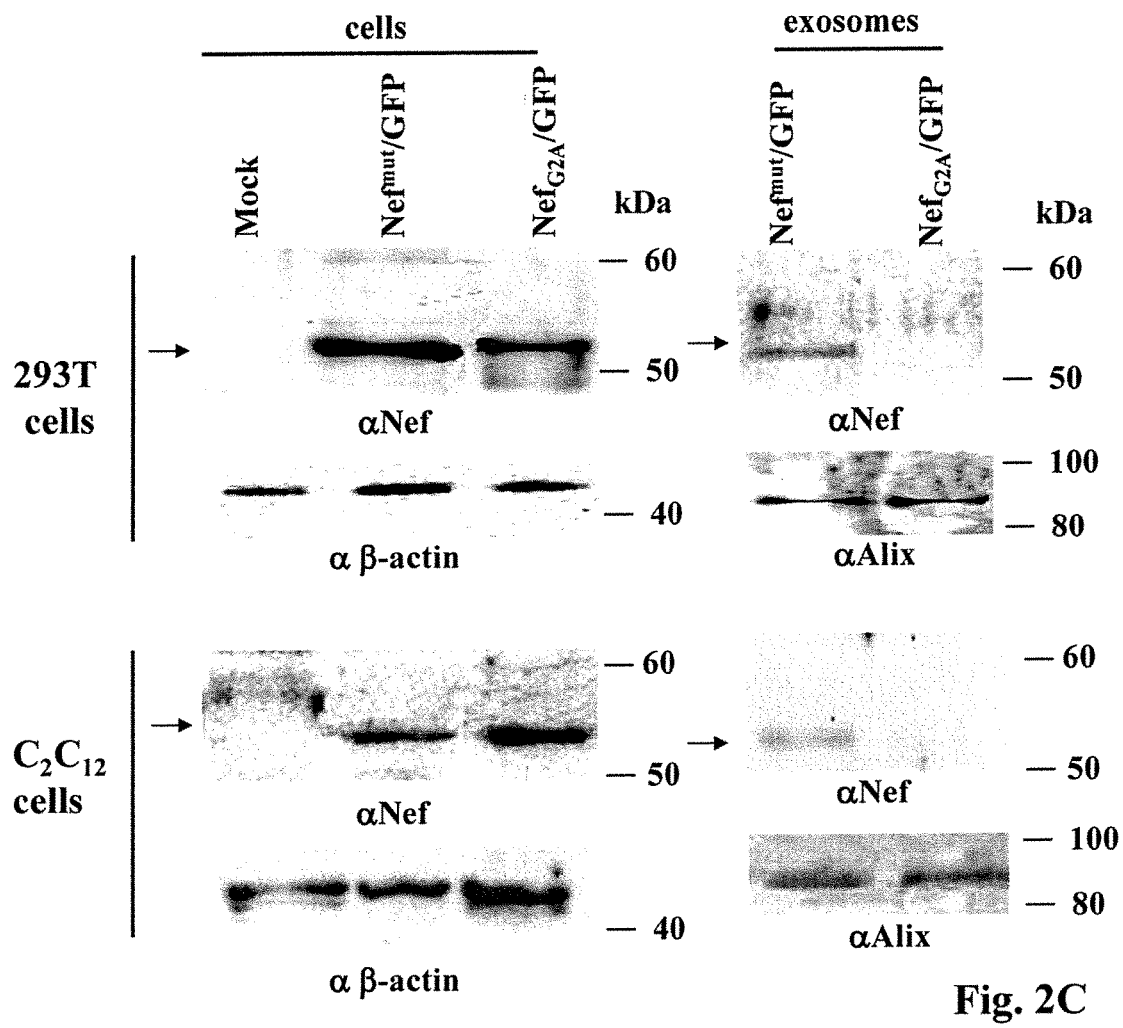
Figure 2D:
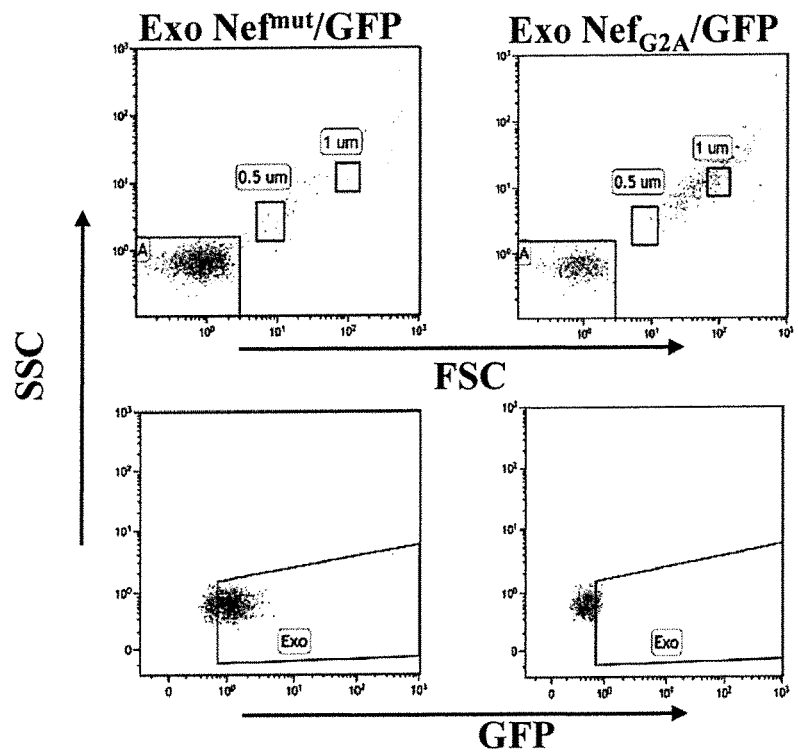

Murine $C_2C_{12}$ muscle cells and, as control, human 293T cells were transfected with vector expressing GFP fused at the C-terminus of either $Nef^{mut}$ or a Nef isotype (i.e., $Nef_{G2A}$) already characterized for its inefficiency to associate with exosomes (26). Transfected cell cultures were monitored for the respective efficiency of transfection (FIG. 2A) which in muscle cells appeared to be over 50% of that detected in 293T cells. The supernatants were collected, and exosomes isolated through differential centrifugations. Exosome preparations were then titrated in terms of AchE activity (FIG. 2B). The two cell types produced apparently similar levels of AchE positive nanovesicles whatever the transfection conditions. The western blot analysis of equal amounts of exosomes shown the presence of Nef-derived molecules in exosomes from both 293T and $C_2C_{12}$ cells transfected with $Nef^{mut}$-GFP but not $Nef_{G2A}$-GFP vectors (FIG. 2C). The FACS analysis of exosome preparations confirmed the association of fluorescence with the nanovesicles recovered from $C_2C_{12}$ cells transfected with $Nef^{mut}$-GFP but not $Nef_{G2A}$-GFP (FIG. 2D).

In sum, it has been proved that exosome-like nanovesicles released by murine muscle cells can be engineered by $Nef^{mut}$-derivatives as previously proven in epithelial-like, transformed human 293T cells.

Figure 3A:
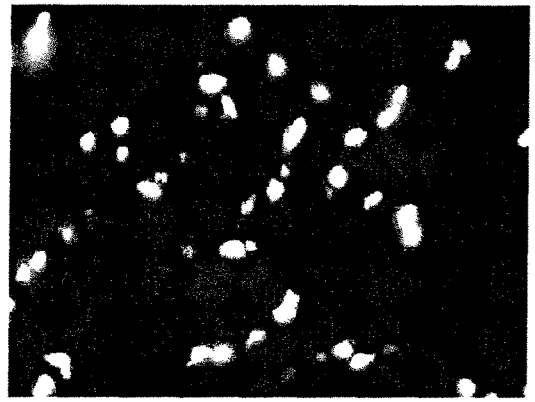
Figure 3A:
Figure 3A:
Figure 3B:
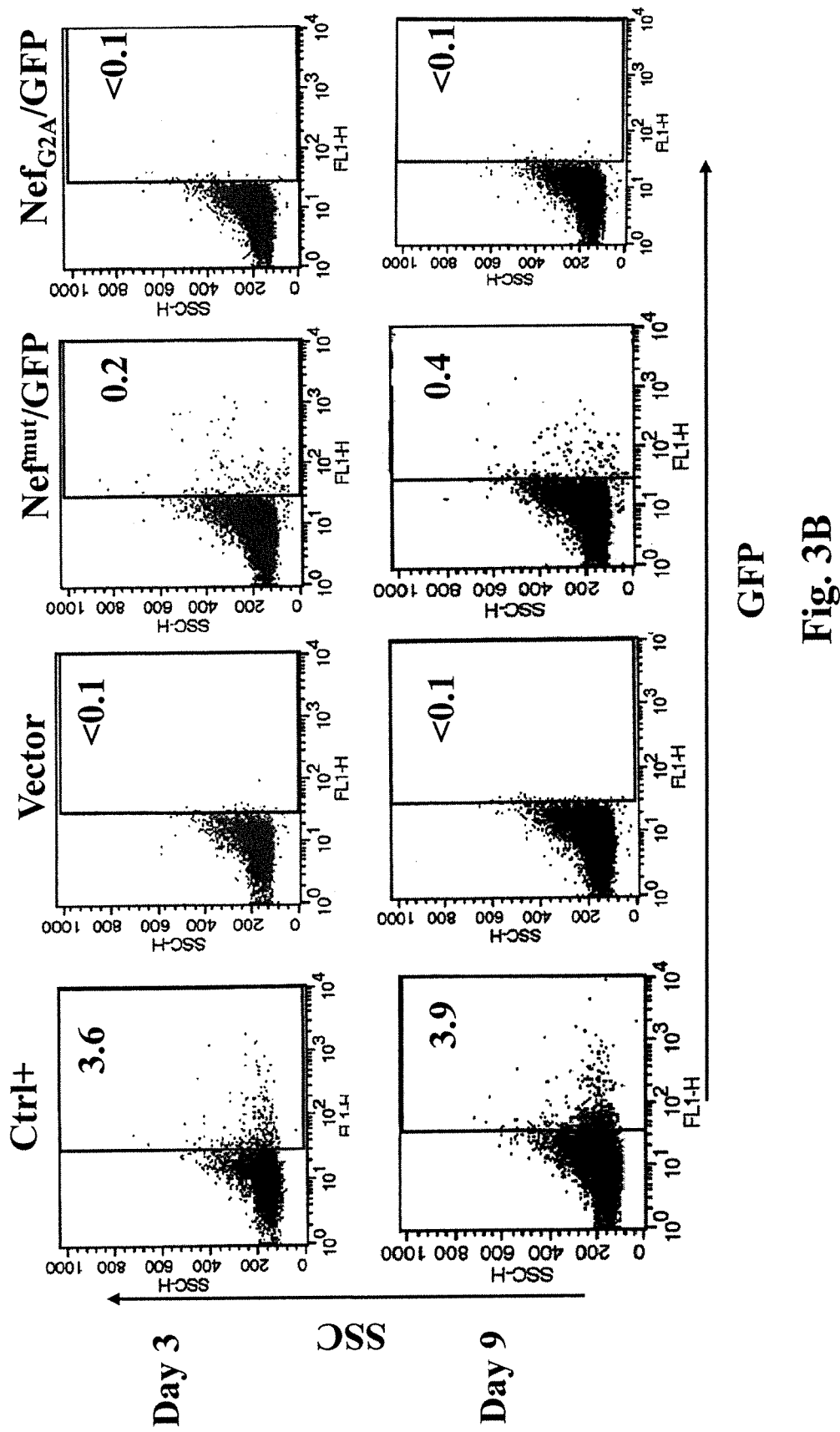

$Nef^{mut}$-Derived Products Can Be Detected in Exosomes from Plasma of DNA Inoculated Mice On the basis of the in vitro results which were obtained with murine muscle cells, the expression of the $Nef^{mut}$-based vector in vivo has been attempted. To this aim, 50 µg of either $Nef^{mut}$-GFP, $Nef_{G2A}$-GFP, or empty vector were inoculated in each quadriceps of C57 Bl/6 mice. Three days later, a number of inoculated mice was sacrificed and their legs cryopreserved. Then, slices obtained from the zones of inoculation were analyzed for the expression of GFP-related products. Consistently with the already described features of Nef and its mutants/derivatives, $Nef^{mut}$ apparently accumulated at the plasma membrane meanwhile disposing also in an intracellular punctate pattern. Differently, the $Nef_{G2A}$ mutant, as consequence of the lack of N-terminal myristoylation, disposed in a more diffuse intracytoplasmic distribution (FIG. 3A). Three and nine days after inoculation, plasma were recovered from the remainder inoculated mice, and the exosomes isolated by differential centrifugations. Exosome preparations were then titrated in terms of AchE activity, and the same amounts of exosomes were bound to white aldehyde/sulphate latex beads. Through this method, even rare fluorescent nanovesicles were expected to be detectable by FACS analysis. Positive signals were scored in samples comprising exosomes isolated from plasma of mice both 3 and 9 days after injection with $Nef^{mut}$-GFP but not $Nef_{G2A}$-GFP vector (FIG. 3B). These results suggested that the inoculation in mice of vectors expressing $Nef^{mut}$-derivatives can lead to generation of engineered exosomes.

Figure 4A:
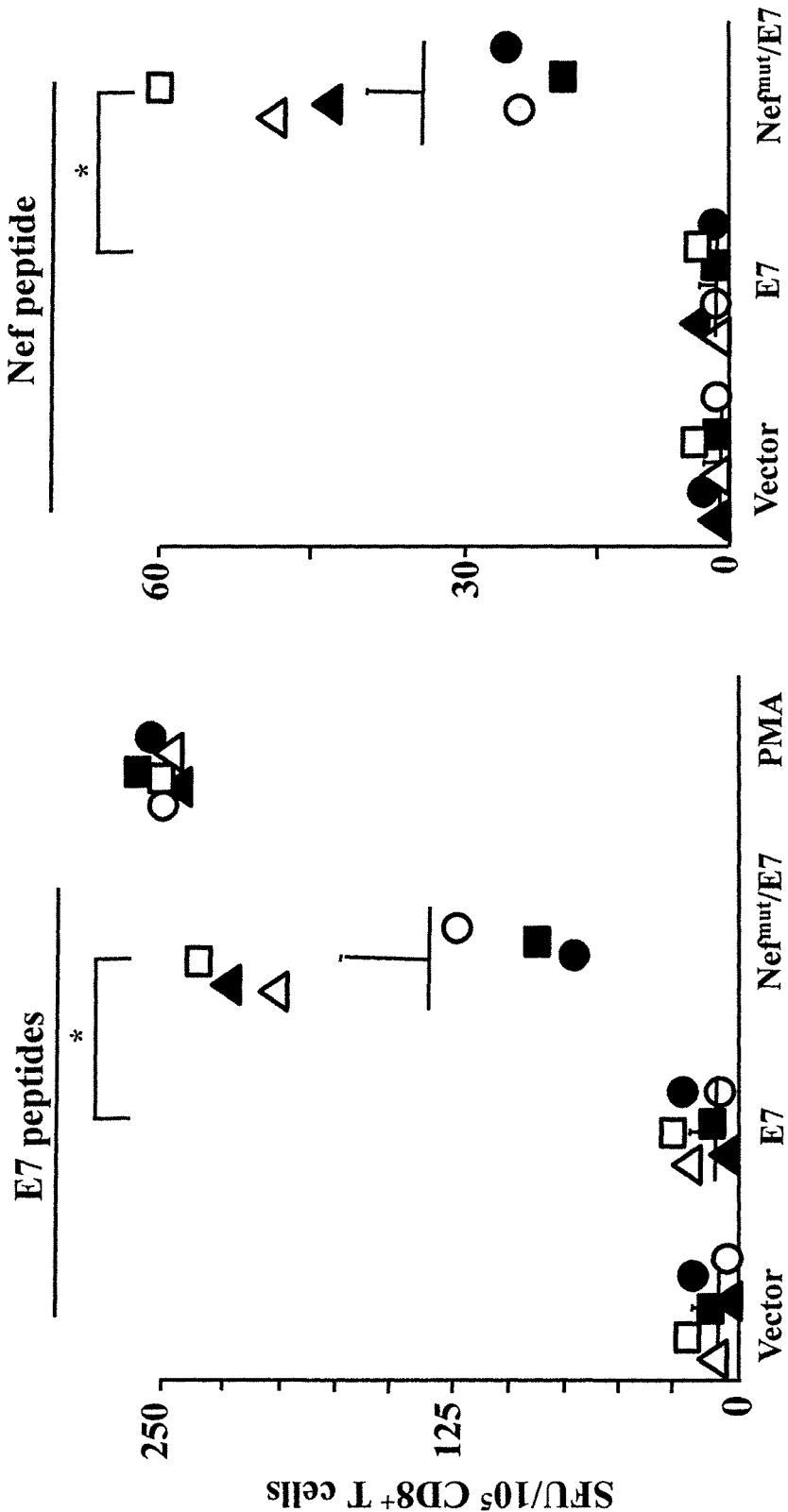

HPV-E7 Specific CTL Response Upon i.m. Inoculation of a $Nef^{mut}$/E7 Expressing DNA Vector Next, the immunogenicity of the antigens uploaded in engineered exosomes generated by the inoculation of DNA vectors expressing $Nef^{mut}$-derivatives was evaluated. To this aim, C57 Bl/6 mice (six per group) were inoculated i.m. in each back lag with 50 µg of vectors expressing either $Nef^{mut}$/E7 or E7 alone, or with empty vector. Of note, the analysis of the immune response after injection of a vector expressing E7 alone was instrumental to evaluate the benefit of the $Nef^{mut}$-fusion in terms of CD3$^+$ T cell immunogenicity. The inoculations were repeated 10 days later, and after additional 10 days the mice were sacrificed, and the splenocytes cultured o.n. in IFN-γ Elispot microwells in the presence of unrelated, Nef- or E7-specific H-2 K$^b$ nonamers. The levels of CD8$^+$ T cell activation observed in cultures with unrelated peptides remained at background levels and similar to those detected in splenocytes cultured in the absence of peptides (not shown). On the other hand, cell activation was clearly detectable in splenocytes from mice inoculated with the $Nef^{mut}$/E7 expressing vector after incubation with either E7 or Nef nonamers (FIG. 4A). Conversely, no CD8$^+$ T cell response was detected in cultures of splenocytes from mice receiving either E7-expressing or empty vector, whatever the peptide used.

Figure 4B:
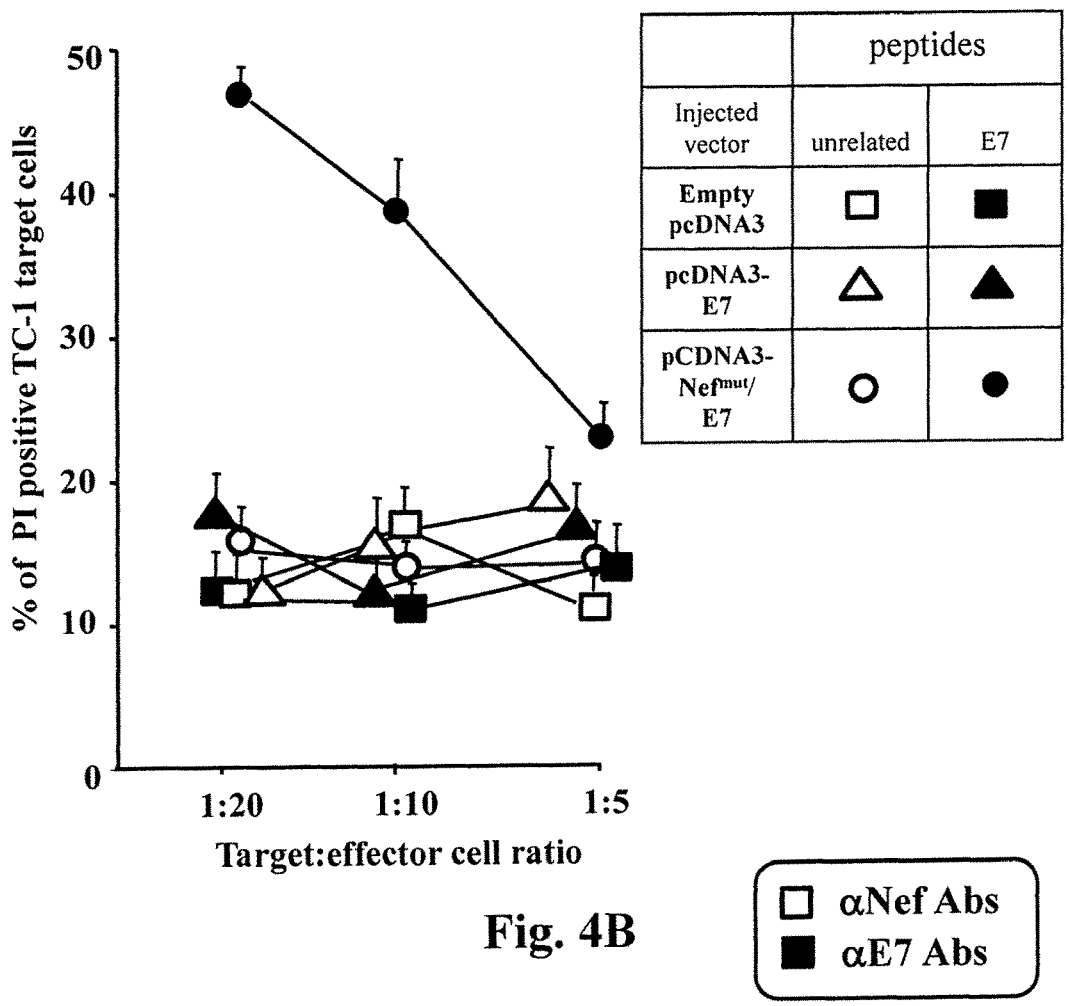
Figure 4C:
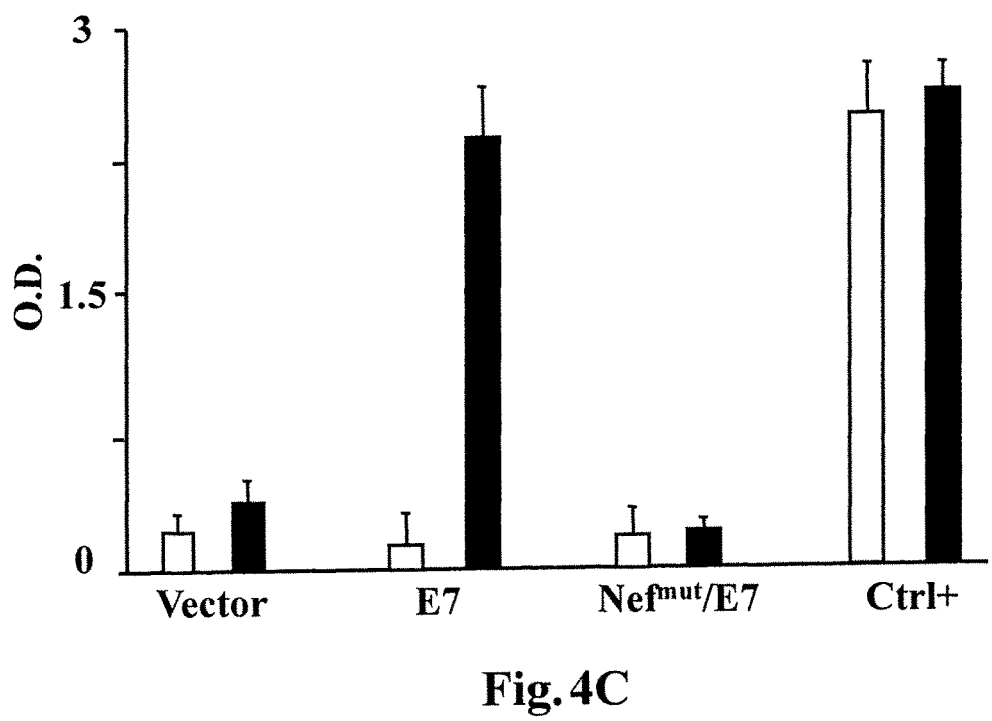

To evaluate whether the CD8+ T cell response associated with a measurable CTL activity, CD8+ T cells were isolated from pools of splenocytes, and then put in co-culture for 6 h at different cell ratios (i.e., from 20:1 to 5:1) with CFSE-labelled EL-4 cells pre-treated o.n. with either unrelated or E7 nonamers. Afterwards, the co-cultures were labelled with 7-AAD, and the mortality levels of target cells scored by FACS analysis. The results reported in FIG. 4B show a clear increase of target cell mortality in both 20:1 and 10:1 co-cultures comprising CD8+ T lymphocytes only from mice inoculated with the Nef$^{mut}$/E7-expressing vector with EL-4 pre-treated with E7-specific nonamers. This result demonstrated that activated CD8+ T lymphocytes detected in mice inoculated with the Nef$^{mut}$/E7-expressing vector by IFN-γ Elispot assay possessed E7-specific cytotoxic activity. Notably, anti-E7 antibodies were detected only in plasma from mice inoculated with the vector expressing E7 alone (FIG. 4C).

Taken together, these data indicated that the i.m. inoculation of a vector expressing an heterologous antigen fused with Nef$^{mut}$ leads to the induction of a strong antigen-specific CTL response in the absence of antibody production.

The Inoculation of DNA Vector Expressing the Wild-Type Nef Isoform Does Not Elicit Nef-Specific CD8+ T Cell Activation The results provide evidence that the i.m. injection of DNA vectors expressing Nef$^{mut}$-derivatives leads to the production of exosomes uploading Nef$^{mut}$ products correlating with the induction of a CTL response against the foreign antigen incorporated into the exosomes. To support the idea that the high levels of Nef$^{mut}$ incorporation in exosomes were mandatory to elicit the antigen specific CD8+ T cell response, the immunogenicity experiments were reproduced however by inoculating mice with vectors expressing the wild-type isoform of Nef which incorporates in exosomes at much lower extents compared to Nef$^{mut}$ (13).

To this end, C57 Bl/6 mice (four per group) were injected i.m. in each back lag with 50 μg of a vector expressing either wtNef or Nef$^{mut}$, or with the empty vector. The inoculations were repeated 10 days later, and after additional 10 days the mice were sacrificed. Splenocytes were then isolated and cultured o.n. in IFN-γ Elispot microwells in the presence of either unrelated or Nef-specific nonamers. As shown in FIG. 5, mice inoculated with the vector expressing wtNef, differently to those receiving the Nef$^{mut}$-vector, failed to mount a detectable CD8+ T Nef-specific response.

These results indicate that the efficiency of antigen uploading in exosomes is critical for the induction of the immune response, also suggesting that the functions of wtNef were not per se involved in the CD8+ T cell activation we observed.

Exosomes Isolated From Plasma of Mice Immunized With a DNA Vector Expressing Nef$^{mut}$/E7 Induce an E7-Specific CD8+ T Cell Response in Syngeneic Mice.

To enforce the hypothesis that the CD8+ T cell immune response detected upon inoculation of Nef$^{mut}$-expressing vectors relies on the in vivo production of engineered exosomes, whether exosomes purified from the plasma of inoculated mice were immunogenic in recipient naïve mice was assessed. To this aim, eight mice were inoculated with vectors expressing E7, Nef$^{mut}$/E7 or the empty vector following the here above detailed schedule. Eight day after the last immunization, PBMCs were recovered through retro orbital bleeding, and put in IFN-γ Elispot microwells to check the E7-specific CD8+ T cell response. As already observed, the injection of the Nef$^{mut}$/E7 expressing vector, but not that expressing E7 alone, gave rise to a well detectable E7-specific CD8+ T cell response (FIG. 6A). Plasma from homogeneous groups were pooled, and exosomes isolated by differential centrifugations. Afterwards, exosomes were titrated in terms of AchE activity, and the equivalent of 6 mU of AchE activity of exosomes were injected s.c. in syngeneic mice three times with ten day intervals. Finally, mice were sacrificed, and splenocytes tested for the E7-specific CD8+ T cell responses. Interestingly, by o.n. culture in IFN-γ Elispot microwells we noticed a E7-specific cell activation only in splenocyte cultures from mice inoculated with exosomes purified from mice injected with the Nef$^{mut}$/E7 expressing vector (FIG. 6B).

These results indicate that the i.m. injection of DNA expressing Nef$^{mut}$/E7 leads to the production of immunogenic exosomes, hence further supporting the idea that the DNA-directed production of endogenous, engineered exosomes was on the basis of the observed strong E7-specific CD8+ T cell immune response.

Figure 7A:
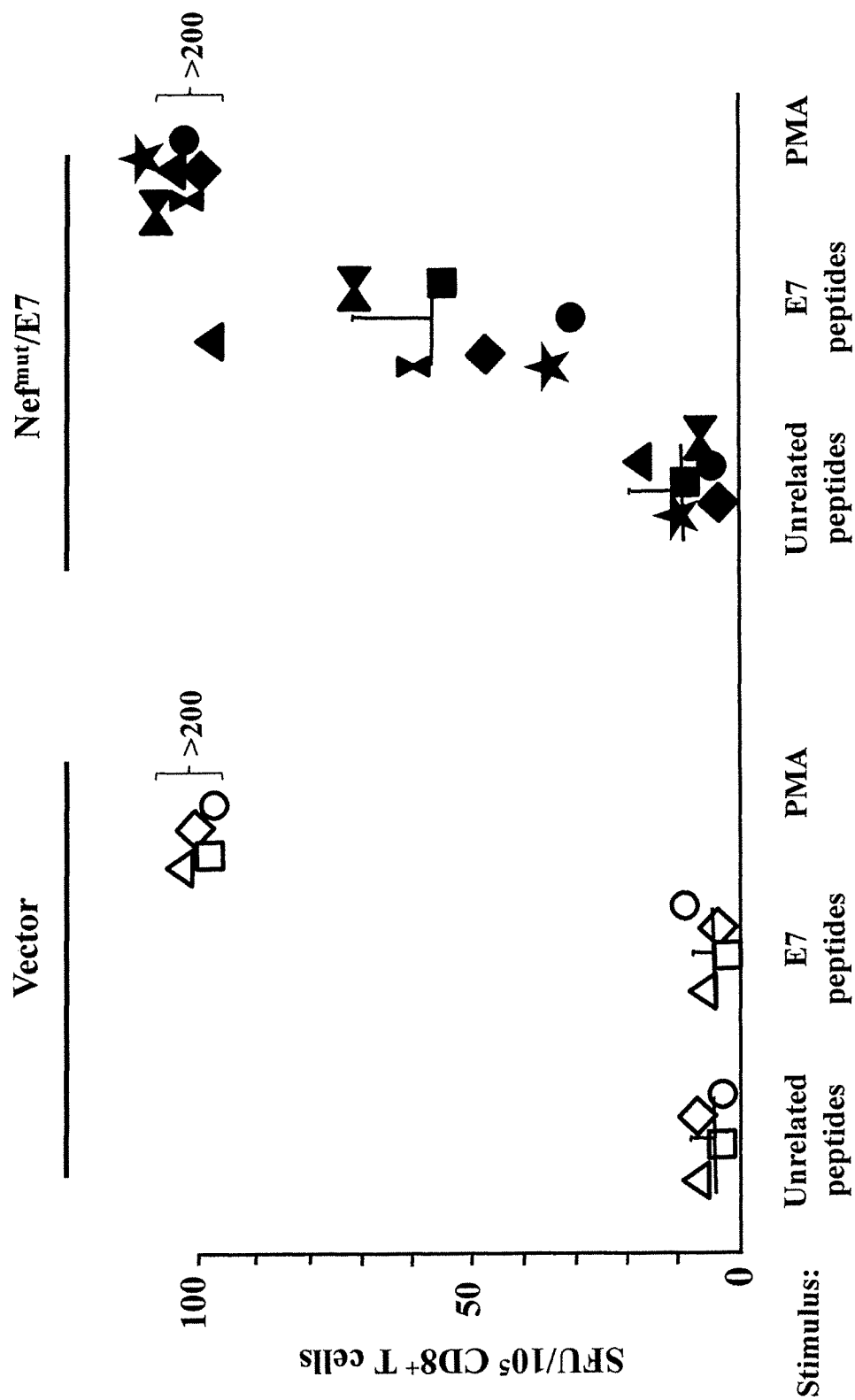
Figure 7B:
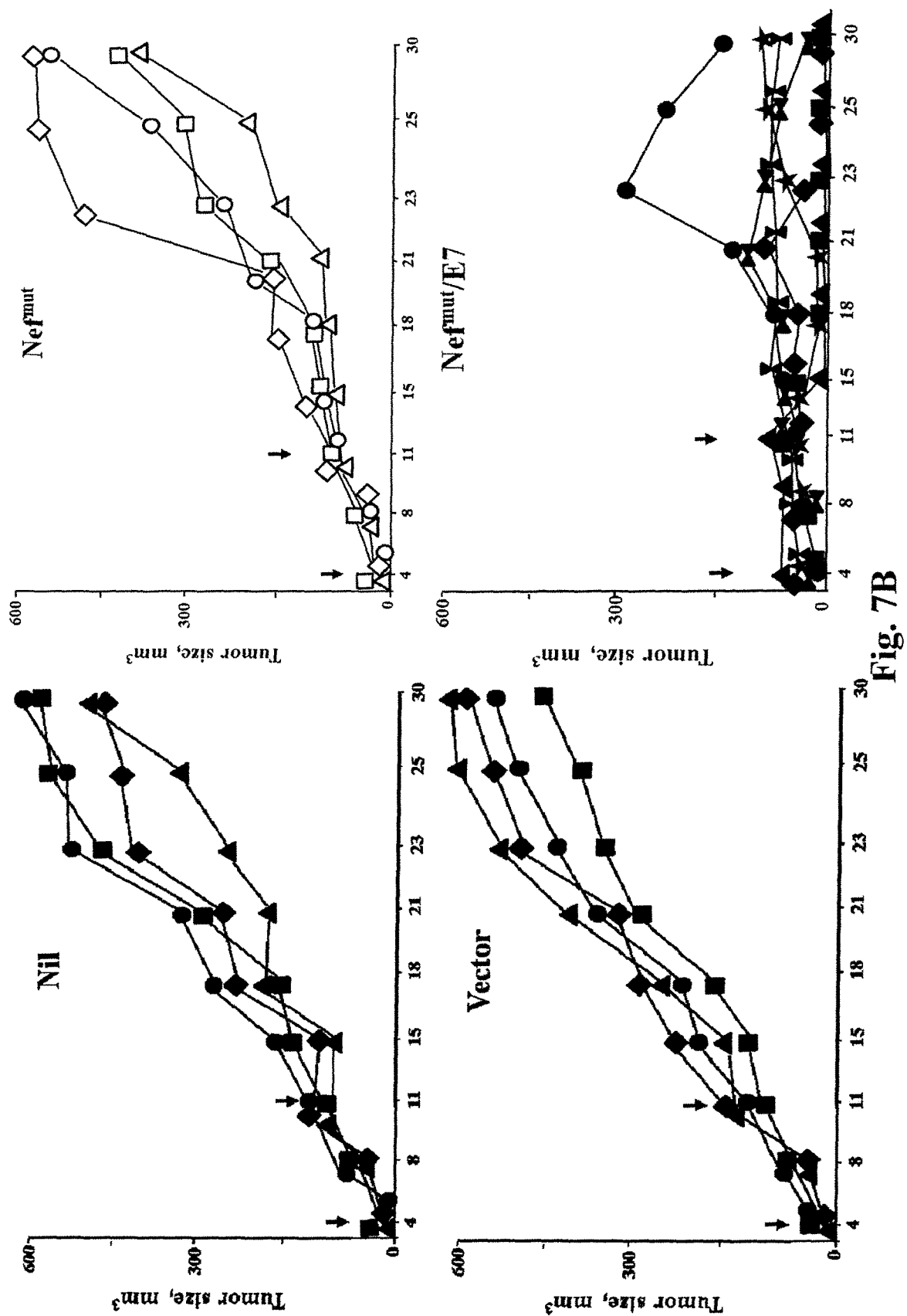
Figure 7C:
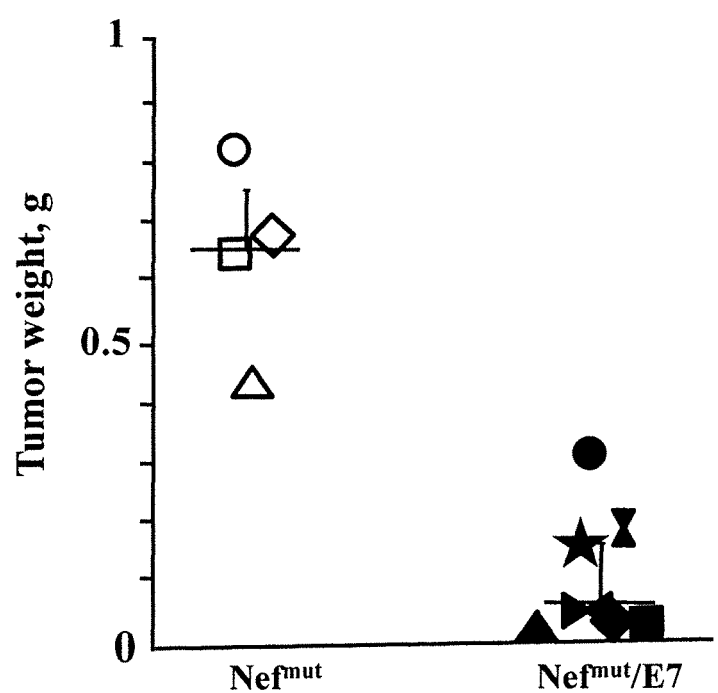

Therapeutic Anti-Tumor Effect of the HPV-E7-Specific CTL Response Induced by i.m. Inoculation of Nef$^{mut}$/E7-Expressing DNA Vector Finally, the potency of the CD8+ T cell immune response evoked by injection of Nef$^{mut}$/E7 expressing vector in terms of anti-tumor effect has been evaluated. To this end, therapeutic immunization assays on C57 Bl/6 mice inoculated s.c. with $2 \times 10^5$ TC-1 cells have been set up. Mice developing a tumor mass detectable by palpation, i.e., of about 2 mm of diameter, were then inoculated with 50 μg/back leg of vectors expressing either empty vector, Nef$^{mut}$ (4 mice per each group) or Nef$^{mut}$/E7 (six mice) at both days 4 and 11 after cell implantation. As control, 4 tumor-implanted mice were injected with the vehicle alone. At day 21, retro orbital bleeding carried out on mice injected with Nef$^{mut}$- or Nef$^{mut}$/E7-expressing vectors served to assess the induction of E7-specific CD8+ T cell immune response (FIG. 7A). The growth of tumors was monitored over 30 days, and thereafter mice were sacrificed, tumors explanted, and weighted. FIG. 7B clearly shows that, whereas the injection of control DNA vectors did not influence the growth of implanted tumor cells, their expansion was severely impaired in mice inoculated with Nef$^{mut}$/E7 vector, being tumor cells still apparently cleared in 3 mice, as confirmed by the tumor weight evaluation (FIG. 7C).

From these data it can be concluded that the inoculation of Nef$^{mut}$/E7-expressing DNA vector elicits a CD8+ T cell immune response also in the presence of tumor cells. Most important, this immune response was both strong and rapid enough to strongly inhibit the growth of previously implanted syngeneic tumor cells.

Taken together, these results represent a relevant milestone towards possible therapeutic applications of immunization strategies based on Nef$^{mut}$-based endogenous exosomes.

EXAMPLE 2

Study on CD8+ T Cell Immunity Elicited by In Vivo Inoculation of Vectors Expressing Antigens Fused with Nef$^{mut}$ The strategy of immunization based on inoculation of DNA vectors expressing an antigen fused to the C-terminus of Nef$^{mut}$ has been successfully applied also to a variety of additional viral antigens (see Tab. 1). In detail, vectors expressing such antigens fused with Nef$^{mut}$ have been injected in either C57 Bl/6 or Balb/c mice following the here above described schedule. From 10 to 15 days after the last inoculation, IFNγ ELISPOT assays were carried out with splenocytes from the injected mice using the peptides listed in Table 1.

TABLE 1

Antigen-specific CD8$^+$ T cell immunity induced in mice inoculated with vectors expressing different antigens fused with Nef$^{mut\,a}$

| Antigen | Spot-forming units/$10^6$ cells | Peptides for detecting CD8$^+$ T cell immunity | Sequence accession number |
|---|---|---|---|
| EboV VP24 | 310 ± 35 | KFINKLDALH (SEQ ID NO: 8) DAVLYYHMM (SEQ ID NO: 9) | AY142960 |
| EboV VP40 | 285 ± 18 | LRIGNQAFLQEFVLPP (SEQ ID NO: 10) | L11365 |
| EboV NP | 409 ± 21 | VYQVNNLEEIC (SEQ ID NO: 11) DAVLYYHMM (SEQ ID NO: 12) | AY142960 |
| HCV NS3 | 190 ± 57 | ITQMYTNV (SEQ ID NO: 13) WYELTPAETSV (SEQ ID NO: 14) | AFN53788.1 |
| WNV NS3 | 210 ± 17 | GYISTKVEL (SEQ ID NO: 15) DRRWCFDGPRTNTIL (SEQ ID NO: 16) | ABG67747.1 |
| Flu NP | 232 ± 44 | ASNENMETM (SEQ ID NO: 17) | ACX46208.1 |

$^a$Shown are the mean values ±SD subtracted background values as calculated from data obtained with splenocytes from four inoculated mice each tested in triplicate wells.

The results support the idea that the injection of DNA expressing antigens fused to Nef$^{mut}$ is instrumental to induce CTL immunity against a wide range of full-length antigens.

EXAMPLE 3

Study of the CTL Activity Elicited by In Vivo Engineered Exosomes According to the Present Invention in Breast Cancer Materials and Methods
Molecular Constructs DNA coding for the extra-cellular domain (ECD) of activated rHER2/neu was recovered by RT-PCR carried out on total RNA extracted from N202.1A cells, i.e., a cell line derived from FVB mice transgenic for rHER-2/neu (27). The following primers comprising the Nhe I and Eco RI restriction sites at the respective 5' end were used: forward (just downstream to the signal peptide) 5' CTAGCTAGCACCCAAGTGTGTACCGGC 3'(SEQ ID NO:18); reverse: 5'CCGGAATTCTCAGTGGGT CA GTTGATGGG 3'(SEQ ID NO:19). To obtain the vector expressing the Nef$^{mut}$/HER2-ECD fusion product, the PCR product was Nhe I/Eco RI cut, and inserted in frame at the 3' terminus of an Nhe I/Eco RI digested pcDNA3-based vector expressing Nef$^{mut}$. Through this strategy, both rat and mouse HER2-ECD sequences were expected to be fused with Nef$^{mut}$ in the resulting molecular constructs. The selection was made on the basis of the presence of rHER2/neu sequence. Vectors expressing Nef$^{mut}$, Nef$^{mut}$/GFP, and Nef$^{mut}$/MART-1 have been already described (13). The IE-CMV-promoted vector expressing the rHER2/neu was kindly provided by A. Amici, University of Urbino, Italy.

Cell Cultures and Transfections

293T, MCF-7, murine muscle $C_2C_{12}$ (all obtained from American Type Culture Collection), and TC-1 cells (28) were grown in Dulbecco's modified Eagle's medium plus 10% heat-inactivated fetal calf serum (FCS). Transfection assays were carried out by Lipofectamine 2000-based method (Invitrogen, Thermo Fisher Scientific), which in the case of $C_2C_{12}$ cells was modified by adding liposomes on freshly trypsinized cells. HLA-A.02 B-LCLs (29), murine splenocytes, and CD8$^+$ T lymphocytes were cultivated in RPMI medium plus 10% FCS. Human primary skeletal muscle cells (SKMC) were obtained from Lonza, and cultivated with the recommended medium.

Human PBMCs were isolated from healthy donors by Fycoll-Hypaque density gradients. Monocytes were isolated from PBMCs using an immunomagnetic monocyte selection kit (Miltenyi). Purity of recovered cell populations was assayed by FACS analysis using PE-conjugated anti-CD14 mAb (Becton Dickinson). Monocytes were differentiated to iDCs upon 4-5 days of culture in RPMI medium supplemented with 20% FCS, 30 ng/mL granulocyte-macrophage colony-stimulating factor (GM-CSF) (Serotec Ltd), and 500 units/mL IL-4 (R&D Systems). DC maturation was obtained through o.n. treatment with 10 ng/mL of lipopolysaccharide (LPS).

Exosome Preparation and Purification

Exosomes were isolated through differential centrifugations as previously described (30) starting from supernatants of 293T cells 48 to 72 hours after transfection. The amounts of recovered exosomes were evaluated by measuring the activity of acetylcholinesterase (AchE, i.e., a classical exosome marker) (31) through Amplex Red kit (Molecular Probes, Thermo Fisher) following the manufacturer's recommendations.

Western Blot

Western blot analyses of both cell lysates and exosomes were carried out as described (13). Filters were revealed using 1:1000 diluted sheep anti-Nef antiserum ARP 444 (MRC), 1:250 diluted anti-β actin AC-74 mAb from Sigma, and 1:100 diluted anti-Alix H-270 polyclonal Abs from Santa Cruz.

Mouse Model

All studies with animals here described have been approved by the Ethical Committee of the ISS (protocol n. 107/2016-PR) according to Legislative Decree 116/92 which has implemented in Italy the European Directive 86/609/EEC on laboratory animal protection. Animals used in our research have been housed and treated according to the guidelines inserted in here above mentioned Legislative Decree. A colony of 129Sv-NeuT transgenic mice generated and bred in the ISS animal facility (32) was used. In these mice, the activated rHER-2/neu gene is promoted by MMLV LTR and virgin females spontaneously develop mammary carcinomas becoming palpable at 15-20 weeks of age. The presence of the rHER2/neu transgene was routinely checked by PCR as described (32). Mice were inoculated i.m. two times at 15 and 17 weeks of age with 50 µg for each quadriceps of plasmid DNA purified with endotoxin-free Qiagen kit. The mammary glands were inspected once a week for tumor monitoring. Mice bearing tumors exceeding 30 mm of diameter were euthanized.

Antibody Detection

Plasma from inoculated mice were 1:20 diluted and tested for the presence of anti-HER2/neu antibodies on 293T cells transfected two days before with a HER2/neu expressing vector. After 2 hours of incubation at 4° C., cells were washed and incubated with FITC-conjugated anti-mouse IgGs, and FACS analyzed 1 hour later. As a positive control, 1:20 diluted anti HER2/neu mAb clone 7.16.4 (Sigma) was used.

ELISPOT Assay

To detect both HER2/neu- and Nef-specific CD8$^+$ T cell immune responses, splenocytes were put in IFN-$\gamma$ Elispot microwells (Millipore) in the presence of 5 µg/ml of either HER2/neu or HIV-1 Nef 9-mer peptides binding the H-2 K$^b$ complex of 129Sv transgenic mice, i.e., ILHDGAYSL (aa 436-444) (33) (SEQ ID NO: 21) and TAATNADCA (aa 48-56) (34) (SEQ ID NO: 5), respectively. H-2 K$^b$ binding heterologous peptides (35) were used as control. After o.n. incubation, IFN-$\gamma$ Elispot plates were developed (Mabtech), and spot-forming units (SFUs) counted.

Cross-Priming Assay

A total of $10^6$ SKMC was transfected with 10 µg of either Nef$^{mut}$-based or control vectors. After 48 hours, the cells were put in co-culture with iDCs in a 1:5 cell ratio, and, in some instances, in the presence of 2 µM of the inhibitors of exosome biosynthesis GW4869 and spiroepoxide (36-41). After an overnight incubation, iDCs were isolated and matured by LPS treatment for 24 hours. Thereafter, iDCs were washed, and put in co-culture with autologous peripheral blood lymphocytes (PBLs) in a 1:10 cell ratio. A week later, the stimulation procedure was repeated, and, after an additional week, CD8$^+$ T cells were recovered for CTL assays.

CTL Assays

CTL assays with murine cells were performed by isolating CD8$^+$ T cells from splenocytes by positive immunomagnetic selection (Miltenyi). They were put in co-culture for 6 hours in RPMI 10% FCS with TC-1 cells previously labeled with carboxyfluorescein succinimidyl ester (CFSE, Invitrogen, Thermo Fisher) following the manufacturer's recommendations, and treated overnight with either HER2/neu, Nef, or unrelated peptides. The co-cultures were run at 10:1 effector/target cell ratio in 200 µL of RPMI 20% in U-bottom 96 well plates. Afterwards, TC-1 cell mortality was scored by FACS analysis soon after addition of 7-AAD at final concentration of 1 CTL assays in human cells were carried out in a similar way except that either MCF-7 or B-LCLs were used as target cells.

Confocal Microscope Analysis

Overnight co-cultures comprising iDCs and SKMC transfected two days before with vectors expressing either GFP or Nef$^{mut}$/GFP, were carried out in a 1:5 cell ratio in the presence or not of GW4869 and spiroepoxide. Thereafter, cells were stained first with anti-CD45 (i.e., a marker of iDCs) for 1 hour at 4° C., and then with Alexa-Fluor 610-conjugated secondary Abs. Finally, co-cultures were labelled with 4',6' diamino-2-phenylindole (DAPI, Vector Laboratories), and fixed in buffered formaldehyde (2% v/v). Phase contrast and fluorescence images were recorded with an Olympus IX-81 device.

Statistical Analysis

When appropriate, data are presented as mean+standard deviation (SD). In some instances, the paired Student's t-Test was used and confirmed using the non-parametric Wilcoxon rank sum test. $p<0.05$ was considered significant.

Results

The Extra-Cellular Domain of rHER2/neu is Efficiently Uploaded in Exosomes Upon Fusion With Nef$^{mut}$.

ECD of rHER2/neu deprived of the signal peptide was fused at the C-terminus of Nef$^{mut}$ in the context of a IE-CMV-promoted eukaryotic vector. To check both stability and exosome incorporation of the fusion product, 293T cells were transiently transfected with vectors expressing either Nef$^{mut}$ or Nef$^{mut}$/HER2-ECD, or with void vector. After 48 hours, cells were lysed and supernatants underwent differential centrifugations to isolate exosomes. Both cell and exosome lysates were analyzed by western blot (FIG. 8). The fusion product appeared stable and uploaded at valuable extents in exosomes. Similar results were obtained by transfecting $C_2C_{12}$ murine muscle cells (not shown).

The Injection in rHER2/neu Transgenic Mice of a DNA Vector Expressing Nef$^{mut}$/HER2-ECD Induces a Specific CD8$^+$ T Lymphocyte Activation in the Absence of Antibody Response It has been assumed that, as already proven for other Nef$^{mut}$-based fusion products (21), i.m. injection in mice of the Nef$^{mut}$/HER2-ECD expressing vector leads to production of immunogenic endogenously engineered exosomes incorporating the Nef$^{mut}$/HER2-ECD fusion product. The question was whether the expected CD8$^+$ T lymphocyte immunogenicity of these exosomes was strong enough to break the tolerance towards HER2/neu.

The induction of anti-HER2/neu antibodies, i.e., an effect already described in mice injected with rHER2/neu DNA vectors (42, 43) has been tested first( ). To this end, HER2/neu transgenic mice were injected with DNA vectors expressing either Nef$^{mut}$ or Nef$^{mut}$/HER2-ECD (3 per group). Fifteen days after the second injection, plasma were recovered and tested for the presence of anti-HER2/neu Abs using as indicator cells 293T transiently transfected with a DNA vector expressing HER2/neu. As reported in FIG. 9, no HER2/neu-specific antibodies were detectable in plasma from mice injected with DNA vector expressing Nef$^{mut}$/HER2-ECD. Differently, the Abs were detectable in plasma from mice injected with lysates of rHER2/neu expressing cells, as previously described (32). These results appeared fully consistent with what we previously reported about the lack of antibody response against the products incorporated into engineered exosomes (14, 21).

Next, the antigen-specific CD8$^+$ T lymphocyte response testing splenocytes from injected mice through IFN-$\gamma$ Elispot assays carried out upon stimulation with H2$^b$-restricted Nef and HER2-ECD nonamers was analyzed. As shown in FIG. 10, lymphocyte activation was detected when splenocytes from mice injected with Nef$^{mut}$-expressing DNA were stimulated with the Nef peptide, but not with the HER2-ECD one. On the other hand, both Nef and HER2-ECD peptides induced lymphocyte activation in splenocyte cultures from mice injected with Nef$^{mut}$/HER2-ECD. Similar results were obtained testing PBMCs recovered by retro-orbital bleeding (not shown).

These data demonstrate the induction of both Nef and HER/neu specific CD8$^+$ T lymphocyte responses in mice injected with Nef$^{mut}$/HER2-ECD DNA vector.

Induction of Antigen-Specific CTL Activity in rHER2/neu Transgenic mice injected with Nef$^{mut}$/HER2-ECD-expressing DNA vector.

Next, the aim of the study was to assess whether the injection of Nef$^{mut}$/HER2-ECD-expressing DNA vector can induce an HER2/neu-specific CTL activity. To this end, CD8$^+$ T lymphocytes were isolated from splenocytes of HER2/neu transgenic mice inoculated with void vector or with vectors expressing either Nef$^{mut}$ or Nef$^{mut}$/HER2-ECD. The CD8$^+$ T lymphocytes were then put in co-culture with syngeneic, CFSE-labeled TC-1 cells pre-treated with the appropriate peptides. After 5 hours, the co-cultures were stopped, labeled with 7-AAD, and analyzed by FACS to evaluate percentages of dead TC-1 target cells. As shown in FIG. 11, an increase of target cell mortality was detectable when CD8$^+$ T lymphocytes from mice injected with Nef$^{mut}$ DNA vector were co-cultured with TC-1 pre-treated with the Nef peptide. More important, a CTL activity was evident also when CD8$^+$ T lymphocytes from mice injected with Nef$^{mut}$/HER2-ECD DNA vector were co-cultured with TC-1 pre-treated with either Nef- or HER2-specific, H2$^b$-restricted peptides.

These results established a link between the i.m. delivery of Nef$^{mut}$/HER2-ECD DNA vector and the induction of HER2/neu-specific CTL activity.

The Break of HER2/neu Tolerance Associates With an Anti-Tumor Activity

Next, the aim of the study was to assess whether the HER2-ECD-specific CTL activity coupled with a detectable anti-tumor activity. Fifteen weeks old 129Sv-Neu T transgenic mice still free from palpable lesions were injected with either vehicle or DNA vectors expressing Nef$^{mut}$ and Nef$^{mut}$/HER2-ECD. The injections were repeated two weeks later, and the appearance of palpable tumors was monitored weekly. As reported in FIG. 12, the injection of Nef$^{mut}$/HER2-ECD expressing DNA associated with a significant delay in the development of tumors. The monitoring was stopped at the time of first sacrifices needed for ethical reasons.

These data highlight a direct relationship between the HER2-ECD-specific CTL activity induced by DNA i.m. injection and anti-tumor activity.

Figure 13A:
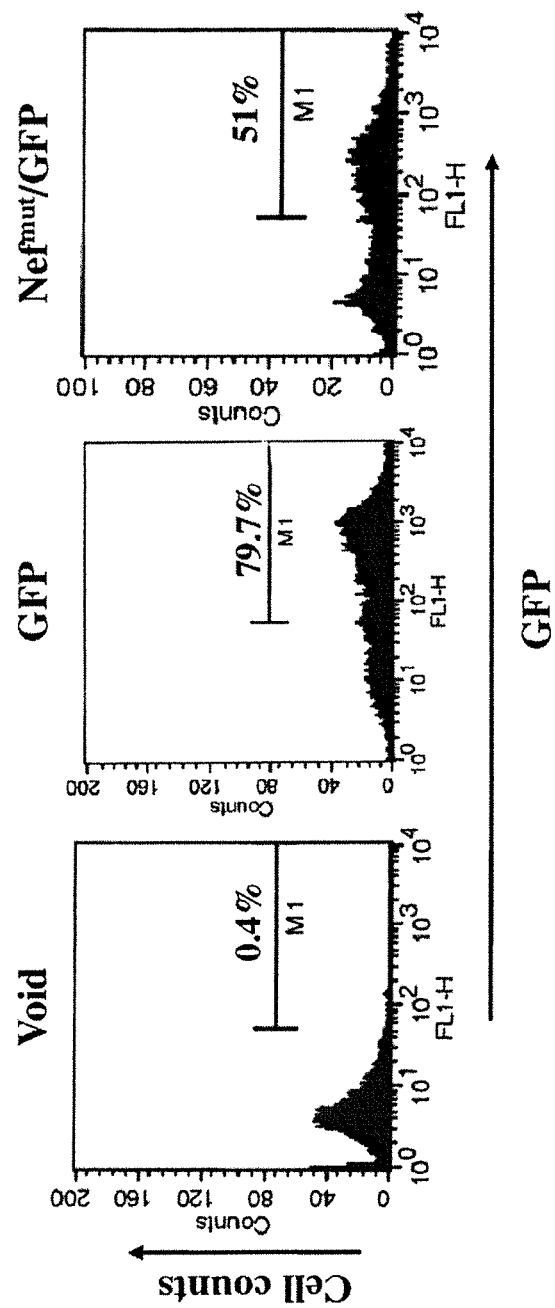
Figure 13B:
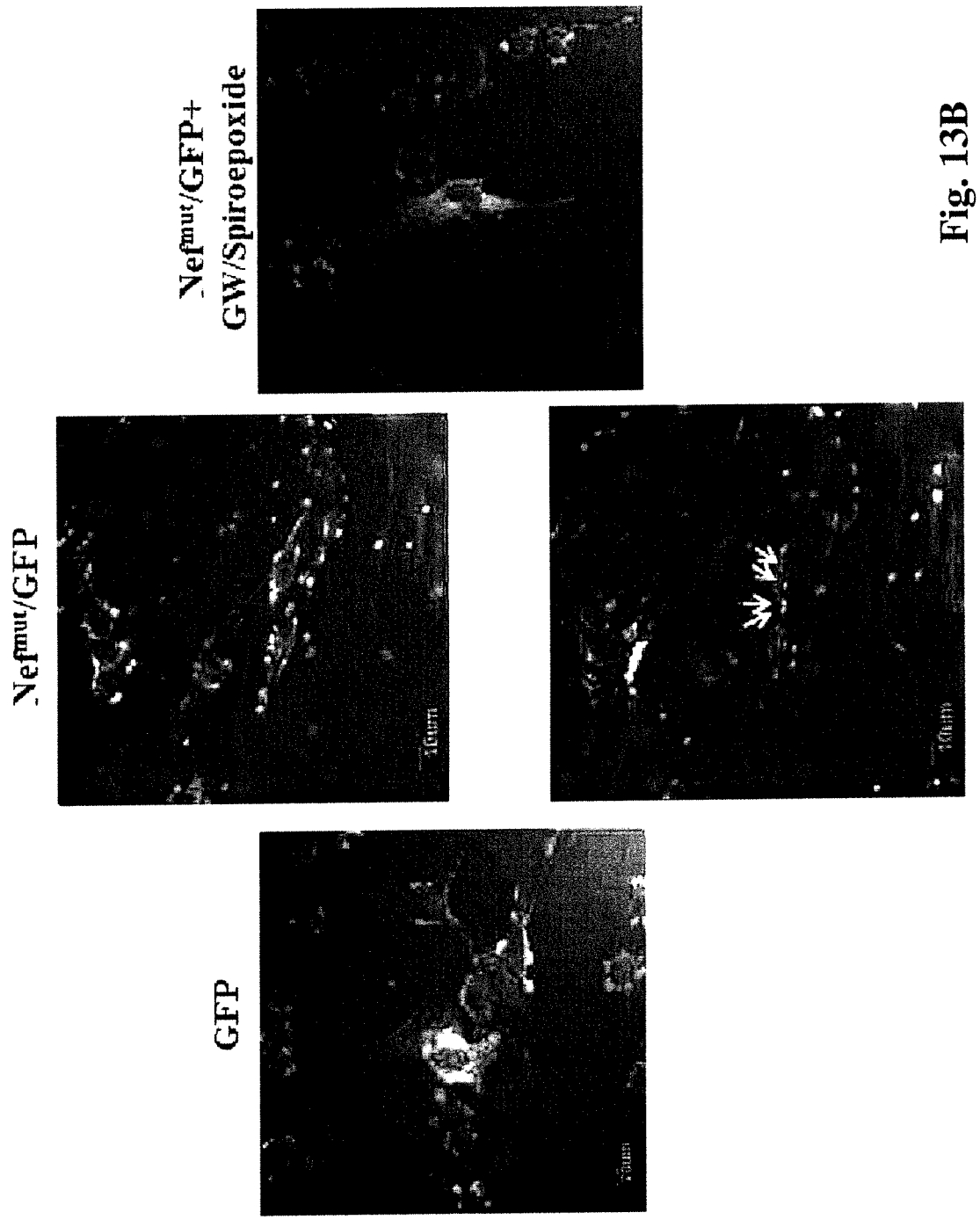

Translating the CTL Vaccine Platform to Humans: Induction of Antigen-Specific CTL Activity by Engineered Exosomes To open the possibility to exploit our CTL vaccine platform in clinic, demonstrating its effectiveness in human system is mandatory. To this end, experiments using conditions at least in part reproducing the mechanism underlying the induction of antigen-specific CD8$^+$ T lymphocyte immune response previously described in mice injected with Nef$^{mut}$-expressing DNA vectors were set up (1). The transfer of exosomes from transfected muscle cells to iDCs was first documented. SKMC were transfected with either GFP or Nef$^{mut}$/GFP DNA vectors, and the transfection efficiency was checked by FACS analysis (FIG. 13A). On this subject, it has been previously documented that the expression of Nef$^{mut}$/GFP leads to production of fluorescent exosomes (13). After co-cultivation of transfected SKMC with iDCs, the presence of fluorescent aggregates into iDCs was documented by confocal microscope analysis upon labeling recipient iDCs with anti-CD45 mAb (FIG. 13B, middle panels). Meanwhile, no GFP fluorescence was detected within the CD45$^+$ cell population when GFP-transfected SKMC were used, as well as when the co-cultures were treated with the inhibitors of exosome biosynthesis GW4869 and spiroepoxide (FIG. 13B, left and right panels, respectively). This result supports the idea that the entry of Nef$^{mut}$/GFP molecules in iDCs was mediated by intercellular transmission of exosomes.

Figure 14A:
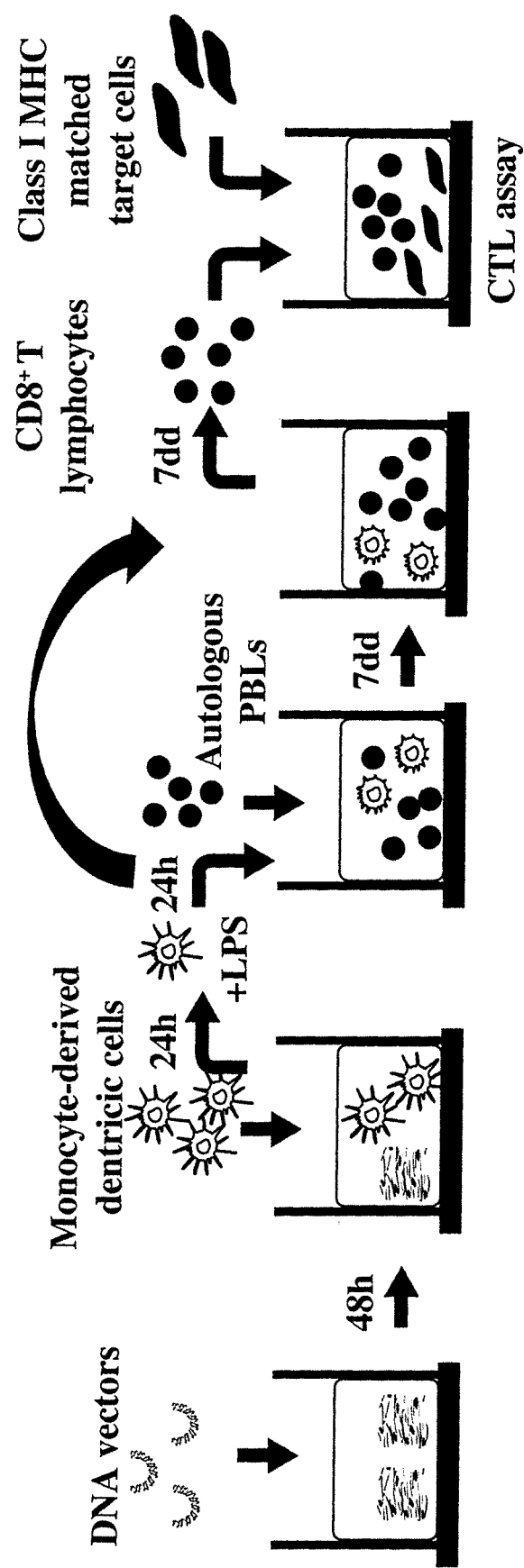
Figure 14C:
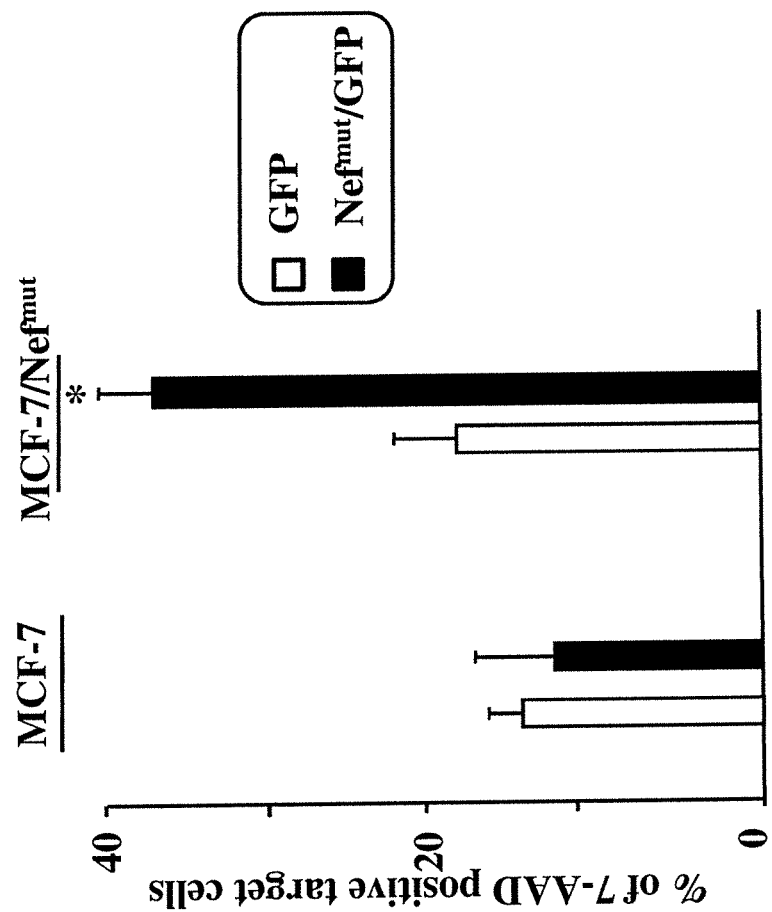
Figure 14B:
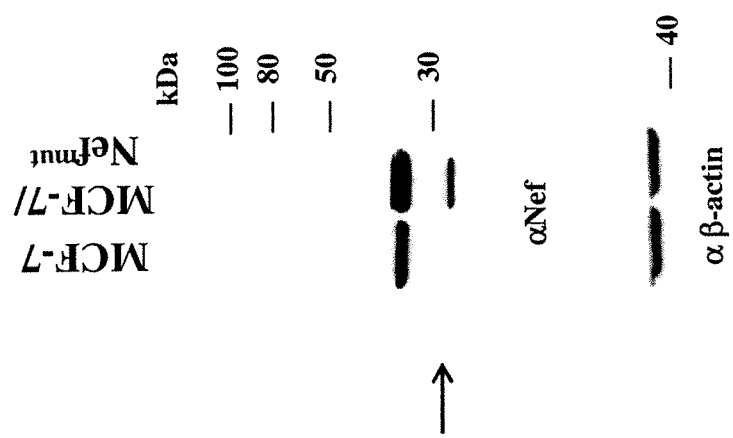

Next, cross-priming assays aimed at evaluating the induction of antigen-specific CTL activity were performed as summarized on FIG. 14A. In detail, SKMC were transfected with DNA vectors expressing Nef$^{mut}$-derivatives, and then co-cultivated with HLA-A.02 iDCs. Twenty-four hours later, iDC were isolated, LPS-matured, and then put in co-culture with autologous PBLs. The mature (m)DC-PBLs co-cultures were carried out for seven days, and, thereafter, the lymphocytes were isolated and subjected to a second stimulation cycle by adding fresh mDC previously co-cultivated with transfected SKMC. After additional seven days, lymphocytes were recovered from the co-cultures, the CD8$^+$ T fraction isolated, and put in co-culture in the context of a CTL assay with HLA-A.02 MCF-7 cells either parental or engineered for stable expression of Nef$^{mut}$ (FIG. 14B). The results from CTL assays (FIG. 14C) showed a mortality of MCF-7/Nef$^{mut}$ target cells appearing higher when they were challenged with CD8$^+$ T cells stimulated by DCs co-cultivated with Nef$^{mut}$ expressing SKMC compared to that detected in co-cultures with CD8$^+$ T cells stimulated by DCs from co-cultures with SKMC transfected with control vector. On the other hand, no antigen-specific CTL activity was detectable throughout using parental MCF-7 as target cells.

Next, these investigations were extended towards antigens fused with Nef$^{mut}$. In addition, whether the production of engineered exosomes was indeed on the basis of the induction of the antigen-specific CTL activity was verified. To this aim, cross-priming assays were reproduced using a DNA vector expressing Nef$^{mut}$ fused with MART-1, i.e., a human melanoma-associated antigen (44), and following the procedures depicted in FIG. 14A, except that SKMC-iDC co-cultures were carried out in the presence or not of the inhibitors of exosome biosynthesis GW4869 and spiroepoxide. CTL assays were finally performed by co-cultivating the CD8$^+$ T lymphocytes with HLA-A.02 B-LCLs previously treated with either HLA-A.02-restricted MART-1 (i.e., AAGIGILTV (SEQ ID NO:20), aa 27-35) (45) or unrelated peptides. As reported in FIG. 15, stimulated CD8$^+$ T lymphocytes showed MART-1 specific CTL activity. It, however, was no more detectable when CD8$^+$ T lymphocytes stimulated by DCs from co-cultures with SKMC carried out in the presence of the exosome inhibitors were used.

These data indicate that the production by transfected muscle cells of exosomes engineered for the incorporation of Nef$^{mut}$ or derivatives thereof are part of the mechanism underlying the induction of the antigen-specific CTL activity we observed with human cells. Hence, these findings support the idea that the CTL vaccine platform has the potential to be applied in humans against tumor antigens.

REFERENCES

1. Halstead S. B., S. J. Thomas. 2011. New Japanese encephalitis vaccines: alternatives to production in mouse brain. *Expert Rev. Vaccines.* 10: 355-64. doi:10.1586/erv.11.7.

2. Ng T., D. Hathaway, N. Jennings, D. Champ, Y. W. Chiang, H. J. Chu. 2013. Equine vaccine for West Nile virus. *Dev. Biol.;* 114: 221-7.

3. El Garch H., J. M. Minke, J. Rehder, S. Richard, C. Edlund Toulemonde, S. Dinic, C. Andreoni, J. C. Audonnet, R. Nordgren, V. Juillard. 2008. A West Nile virus (WNV) recombinant canarypox to virus vaccine elicits WNV-specific neutralizing antibodies and cell-mediated immune responses in the horse. *Vet. Immunol. Immunopathol.* 123: 230-9.

4. Stüve O., T. N. Eagar, E. M. Frohman, P. D. Cravens. 2007. DNA plasmid vaccination for multiple sclerosis. *Arch. Neurol.* 64: 1385-6.

5. Guescini M., D. Guidolin, L. Vallorani, L. Casadei, A. M. Gioacchini, P. Tibollo, M. Battistelli, E. Falcieri, L. Battistin, L. F. Agnati, V. Stocchi. 2010. C2C12 myoblasts release micro-vesicles containing mtDNA and proteins involved in signal transduction. *Exp Cell Res.* 16: 1977-84. doi:10.1016/j.yexcr.2010.04.006.

6. Romancino D. P., G. Paterniti, Y. Campos, A. De Luca, V. Di Felice, A. d'Azzo, A. Bongiovanni. 2013. Identification and characterization of the nano-sized vesicles released by muscle cells. *FEBS Lett.* 587: 1379-84. doi: 10.1016/j.febslet.2013.03.012.

7. Morse M. A., J. Garst, T. Osada, S. Khan, A. Hobeika, T. M. Clay, N. Valente, R. Shreeniwas, M. A. Sutton, A. Delcayre, D. H. Hsu, J. B. Le Pecq, H. K. Lyerly. 2005. A phase I study of dexosome immunotherapy in patients with advanced non-small cell lung cancer. *J. Transl Med.* 3:9.

8. Escudier B., T. Dorval, N. Chaput, T. André, M. P. Caby, S. Novault, C. Flament, C. Leboulaire, C. Borg, S. Amigorena, C. Boccaccio, C. Bonnerot, O. Dhellin, M. Movassagh, S. Piperno, C. Robert, V. Serra, N. Valente, J. B. Le Pecq, A. Spatz, C O. Lantz, T. Tursz, E. Angevin, L. Zitvogel. 2005. Vaccination of metastatic melanoma patients with autologous dendritic cell (DC) derived-exosomes: results of the first phase I clinical trial. *J. Transl Med.* 3:10.

9. Dai S., D. Wei, Z. Wu, X. Zhou, X. Wei, H. Huang, G. Li. 2008. Phase I clinical trial of autologous ascites-derived exosomes combined with GM-CSF for colorectal cancer. *Mol Ther.* 16: 782-90. doi: 10.1038/mt.2008.1.

10. Tan A., H. De La Peña, A. M. Seifalian. 2010. The application of exosomes as a nanoscale cancer vaccine. *Int J Nanomedicine.* 5: 889-900. doi:10.2147/IJN.S13402.

11. Chaput N., C. Théry. 2011 Exosomes: immune properties and potential clinical implementations. *Semin Immunopathol.* 33:419-40. doi:10.1007/s00281.

12. Peretti S., I. Schiavoni, K. Pugliese, M. Federico. 2005. Cell death induced by the herpes simplex virus-1 thymidine kinase delivered by human immunodeficiency virus-1-based virus-like particles. *Mol Ther.* 12: 1185-96.

13. Lattanzi L., M. Federico. 2012. A strategy of antigen incorporation into exosomes: comparing cross-presentation levels of antigens delivered by engineered exosomes and by lentiviral virus-like particles. *Vaccine.* 30: 7229-37. doi: 10.1016/j.vaccine.2012.10.010.

14. Di Bonito P., B. Ridolfi, S. Columba-Cabezas, A. Giovannelli, C. Chiozzini, F. Manfredi, S. Anticoli, C. Arenaccio, M. Federico. 2015. HPV-E7 delivered by engineered exosomes elicits a protective CD8$^+$ T cell-mediated immune response. *Viruses.* 7: 1079-99. doi: 10.3390/v7031079.

15. Fry E A, Taneja P, Inoue K. 2016. Clinical applications of mouse models for breast cancer engaging HER2/neu. *Integr Cancer Sci Ther* 3(5):593-603.

16. Rolla S, Nicolóo C, Malinarich S, Orsini M, Forni G, Cavallo F, Ria F. 2006. Distinct and non-overlapping T cell receptor repertoires expanded by DNA vaccination in wild-type and HER-2 transgenic BALB/c mice. *J Immunol* 177(11):7626-7633.

17. Rovero S, Amici A, Di Carlo E, Bei R, Nanni P, Quaglino E, Porcedda P, Boggio K, Smorlesi A, Lollini P L, Landuzzi L, Colombo M P, Giovarelli M, Musiani P, Forni G. 2000. DNA vaccination against rat her-2/Neu p185 more effectively inhibits carcinogenesis than transplantable carcinomas in transgenic BALB/c mice. *J. Immunol* 165(9):5133-5142.

18. Quaglino E, Iezzi M, Mastini C, Amici A, Pericle F, Di Carlo E, Pupa S M, De Giovanni C, Spadaro M, Curcio C, Lollini P L, Musiani P, Forni G, Cavallo F. 2004. Electroporated DNA vaccine clears away multifocal mammary carcinomas in her-2/neu transgenic mice. *Cancer Res* 64(8):2858-2864.

19. Quaglino E, Mastini C, Iezzi M, Forni G, Musiani P, Klapper L N, Hardy B, Cavallo F. 2005. The adjuvant activity of BAT antibody enables DNA vaccination to inhibit the progression of established autochthonous Her-2/neu carcinomas in BALB/c mice. *Vaccine* 23(25):3280-3287.

20. Schreiber R D, Old L J, Smyth M J. 2011. Cancer immunoediting: integrating immunity's roles in cancer suppression and promotion. *Science* 331(6024):1565-1570.

21. Di Bonito P, Chiozzini C, Arenaccio C, Anticoli S, Manfredi F, Olivetta E, Ferrantelli F, Falcone E, Ruggieri A, Federico M. 2017. Antitumor HPV E7-specific CTL activity elicited by in vivo engineered exosomes produced through DNA inoculation. *Int J Nanomedicine* 12:4579-4591.

22. van der Burg S H, Arens R, Ossendorp F, van Hall T, Melief C J. 2016. Vaccines for established cancer: overcoming the challenges posed by immune evasion. *Nat Rev Cancer* 16(4):219-233.

23. Keppler O. T., I. Allespach, L. Schüller, D. Fenard, W. C. Greene, O. T. Fackler. 2005. Rodent cells support key functions of the human immunodeficiency virus type 1 pathogenicity factor Nef. *J. Virol.* 79: 1655-65.

24. D'Aloja P., E. Olivetta, R. Bona, F. Nappi, D. Pedacchia, K. Pugliese, G. Ferrari, P. Verani, M. Federico. 1998. gag, vif, and nef genes contribute to the homologous viral interference induced by a nonproducer human immunodeficiency virus type 1 (HIV-1) variant: identification of novel HIV 1-inhibiting viral protein mutants. *J. Virol.* 72: 4308-19.

25. Massa S., P. Simeone, A. Muller, E. Benvenuto, A. Venuti, R. Franconi. 2008. Antitumor activity of DNA vaccines based on the human papillomavirus-16 E7 protein genetically fused to a plant virus coat protein. *Hum. Gene Ther.* 19: 354-64. doi: 10.1089/hum.2007.122.

26. Arenaccio C., C. Chiozzini, S. Columba-Cabezas, F. Manfredi, M. Federico. 2014. Cell activation and HIV-1 replication in unstimulated CD4$^+$ T lymphocytes ingesting exosomes from cells expressing defective HIV-1. *Retrovirology.* 11: 46. doi: 10.1186/1742-4690-11-46.

27. Nanni P, Nicoletti G, De Giovanni C, Landuzzi L, Di Carlo E, Cavallo F, Pupa S M, Rossi I, Colombo M P, Ricci C, Astolfi A, Musiani P, Forni G, Lollini P L. 2001. Combined allogeneic tumor cell vaccination and systemic 28. Halbert C L, Demers G W, Galloway D A. 1991. The E7 gene of human papillomavirus type 16 is sufficient for immortalization of human epithelial cells. *J. Virol* 65: 473-478.
29. Di Bonito P, Grasso F, Mochi S, Petrone L, Fanales-Belasio E, Mei A, Cesolini A, Laconi G, Conrad H, Bernhard H, Dembek C J, Cosma A, Santini S M, Lapenta C, Donati S, Muratori C, Giorgi C, Federico M. 2009. Anti-tumor CD8+ T cell immunity elicited by HIV-1-based virus-like particles incorporating HPV-16 E7 protein. *Virology* 395:45-55.
30. Théry C, Amigorena S, Raposo G, Clayton A. 2006. Isolation and characterization of exosomes from cell culture supernatants and biological fluids. *Curr Prot Cell Biol* 3. doi: 10.1002/0471143030.cb0322s30.
31. Rieu S, Géminard C, Rabesandratana H, Sainte-Marie J, Vidal M. 2000. Exosomes released during reticulocyte maturation bind to fibronectin via integrin alpha4beta1. *Eur J Biochem;* 267:583-590.
32. Aricò E, Sestili P, Carpinelli G, Canese R, Cecchetti S, Schiavoni G, D'Urso M T, Belardelli F, Proietti E. 2016. Chemo-immunotherapy induces tumor regression in a mouse model of spontaneous mammary carcinogenesis. *Oncotarget* 7(37):59754-59765.
33. Gritzapis A D, Mahaira L G, Perez S A, Cacoullos N T, Papamichail M, Baxevanis C N. 2006. Vaccination with human HER-2/neu (435-443) CTL peptide induces effective antitumor immunity against HER-2/neu-expressing tumor cells in vivo. *Cancer Res* 66(10):5452-5460.
34. Liang X, Fu T M, Xie X, Emini E A, Shiver J W. 2002. Development of HIV-1 Nef vaccine components: immunogenicity study of Nef mutants lacking myristoylation and dileucine motif in mice. *Vaccine* 20:413-421.
35. Bauer S, Heeg K, Wagner H, Lipford G B. 1995. Identification of H-2 Kb binding and immunogenic peptides from human papilloma virus tumour antigens E6 and E7. *Scand J Immunol* 42:317-323.
36. Chairoungdua A, Smith D L, Pochard P, Hull M, Caplan M J. 2010. Exosome release of beta-catenin: a novel mechanism that antagonizes Wnt signaling. *J Cell Biol* 190:1079-1091.
37. Kogure T, Lin W L, Yan I K, Braconi C, Patel T. 2011. Intercellular nanovesicle-mediated microRNA transfer: a mechanism of environmental modulation of hepatocellular cancer cell growth. *Hepatology* 54:1237-1248.
38. Kosaka N, Iguchi H, Yoshioka Y, Takeshita F, Matsuki Y, Ochiya T. 2010. Secretory mechanisms and intercellular transfer of microRNAs in living cells. *J Biol Chem* 285: 17442-17452.
39. Kosaka N, Iguchi H, Yoshioka Y, Hagiwara K, Takeshita F, Ochiya T. 2012. Competitive interactions of cancer cells and normal cells via secretory microRNAs. *J Biol Chem* 287:1397-1405.
40. Trajkovic K, Hsu C, Chiantia S, Rajendran L, Wenzel D, Wieland F, Schwille P, Brugger B, Simons M. 2008. Ceramide triggers budding of exosome vesicles into multivesicular endosomes. *Science* 319:1244-1247.
41. Yuyama K, Sun H, Mitsutake S, Igarashi Y. 2012. Sphingolipid-modulated exosome secretion promotes clearance of amyloid-beta by microglia. *J Biol Chem* 287:10977-10989.
42. Nanni P, Landuzzi L, Nicoletti G, De Giovanni C, Rossi I, Croci S, Astolfi A, Iezzi M, Di Carlo E, Musiani P, Forni G, Lollini P L. 2004. Immunoprevention of mammary carcinoma in HER-2/neu transgenic mice is IFN-gamma and B cell dependent. *J Immunol* 173(4):2288-2296.
43. Rolla S, Marchini C, Malinarich S, Quaglino E, Lanzardo S, Montani M, Iezzi M, Angeletti M, Ramadori G, Forni G, Cavallo F, Amici A. 2008. Protective immunity against neu-positive carcinomas elicited by electroporation of plasmids encoding decreasing fragments of rat neu extracellular domain. *Hum Gene Ther* 19(3):229-240.
44. Busam K J, Jungbluth A A. 1996. Melan-A, a new melanocytic differentiation marker. *Adv Anat Pathol* 6: 12-18.
45. Rivoltini L, Kawakami Y, Sakaguchi K, Southwood S, Sette A, Robbins P F, Marincola F M, Salgaller M L, Yannelli Y R, Appella E, Rosenberg S A. 1995. Induction of tumor-reactive CTL from peripheral blood and tumor-infiltrating lymphocytes of melanoma patients by in vitro stimulation with an immunodominant peptide of the human melanoma antigen MART-1. *J Immunol* 154: 2257-2265.

---

The invention claimed is:

1. A method of inducing a therapeutically effective cytotoxic lymphocyte (CTL) immune response in a subject, the method comprising:
   administering to the muscle of a subject a nucleic acid vaccine comprising:
   a) a nucleic acid expression vector, wherein the expression vector comprises a polynucleotide encoding a fusion protein, wherein said fusion protein comprises:
      (i) human HIV-1 Nef protein with mutations 3C, 153L and 177G, fused at its C-terminus to
      (ii) an immunogenic antigen; and
   b) one or more of a pharmaceutically acceptable excipient and/or adjuvant;
   wherein the administration of the nucleic acid vaccine induces a therapeutically effective CTL immune response.

2. The method of inducing a CTL immune response according to claim 1, wherein the antigen is selected from the group consisting of a Human Papilloma virus antigen, an HIV antigen, an Ebola virus antigen, a West Nile virus antigen, an HBV antigen, an HCV antigen, a Crimean-Congo virus antigen, an Influenza A virus antigen, a human melanoma antigen, and a human tumor-associated antigen.

3. The method of inducing a CTL immune response according to claim 2, wherein the antigen is Human Papilloma virus E6 or E7.

4. The method of inducing a CTL immune response according to claim 2, wherein the antigen is HIV Gag or Tat.

5. The method of inducing a CTL immune response according to claim 2, wherein the antigen is Ebola virus VP24, VP40, NP, or GP.

6. The method of inducing a CTL immune response according to claim 2, wherein the antigen is West Nile virus NS3.

7. The method of inducing a CTL immune response according to claim 2, wherein the antigen is HBV Core antigen.

8. The method of inducing a CTL immune response according to claim 2, wherein the antigen is HCV Core antigen, NS3, E1 or E2.

9. The method of inducing a CTL immune response according to claim 2, wherein the antigen is Crimean-Congo virus GP or NP.

10. The method of inducing a CTL immune response according to claim 2, wherein the antigen is Influenza virus A NP or M1.

11. The method of inducing a CTL immune response according to claim 2, wherein the human melanoma antigen is MAGE-A3 or MART-1.

12. The method of inducing a CTL immune response according to claim 2, wherein the human tumor-associated antigen is Her2/Neu or Hox B7.

13. The method of inducing a CTL immune response according to claim 1, wherein the adjuvant is an adjuvant of $CD8^+$ T cell response.

14. The method of inducing a CTL immune response according to claim 1, wherein the fusion protein consists of (i) human HIV-1 Nef protein with mutations 3C, 153L and 177G, fused at its C-terminus to (ii) an immunogenic antigen.

* * * * *